US 8,979,822 B2

(12) United States Patent
Vogelbaum et al.

(10) Patent No.: US 8,979,822 B2
(45) Date of Patent: *Mar. 17, 2015

(54) CATHETER ASSEMBLY

(75) Inventors: Michael A. Vogelbaum, Moreland Hills, OH (US); Ji-Feng Chen, Lakewood, OH (US); Shengqiang Gao, Beachwood, OH (US); Michael Collinson, Camarillo, CA (US); Robert B. Guthrie, Ventura, CA (US)

(73) Assignee: The Cleveland Clinic Foundation, Cleveland, OH (US)

( * ) Notice: Subject to any disclaimer, the term of this patent is extended or adjusted under 35 U.S.C. 154(b) by 48 days.

This patent is subject to a terminal disclaimer.

(21) Appl. No.: 13/487,395

(22) Filed: Jun. 4, 2012

(65) Prior Publication Data
US 2012/0323175 A1    Dec. 20, 2012

Related U.S. Application Data

(60) Provisional application No. 61/493,777, filed on Jun. 6, 2011.

(51) Int. Cl.
*A61M 25/00* (2006.01)
*A61M 25/01* (2006.01)
*A61M 25/10* (2013.01)

(52) U.S. Cl.
CPC ....... *A61M 25/0102* (2013.01); *A61M 25/0054* (2013.01); *A61M 25/003* (2013.01); *A61M 25/0082* (2013.01); *A61M 25/1002* (2013.01); *A61M 2025/0024* (2013.01); *A61M 2025/0039* (2013.01); *A61M 2025/0057* (2013.01);
(Continued)

(58) Field of Classification Search
CPC ................ A61M 25/0067; A61M 25/0074; A61M 25/0082; A61M 25/0084; A61M 25/0087; A61M 25/0054; A61M 25/0063
USPC ..................... 604/264, 95.04, 525
See application file for complete search history.

(56) References Cited

U.S. PATENT DOCUMENTS 5,354,279 A    10/1994  Hofling
5,419,777 A    5/1995   Hofling
(Continued)

FOREIGN PATENT DOCUMENTS

WO    WO 2008/020967 A2    2/2008
WO    WO 2008/115566 A2    9/2008
(Continued)

OTHER PUBLICATIONS

Partial PCT International Search Report and Written Opinion dated Sep. 13, 2012, pp. 1-6.

*Primary Examiner* — Laura Bouchelle
(74) *Attorney, Agent, or Firm* — Tarolli, Sundheim, Covell & Tummino LLP

(57) ABSTRACT

A catheter assembly comprises a first catheter including a wall with an inner surface at least partially defining a lumen. A second catheter is connected to the wall of the first catheter and is disposed outward of the inner surface of the wall. The second catheter is at least partially covered by a sheath portion of the first catheter. A first portion of the wall of the first catheter is made of a relatively low durometer elastomeric material and is relatively extensible. A second portion of the wall is formed of a relatively high durometer elastomeric material and is relatively inextensible.

81 Claims, 14 Drawing Sheets

(52) U.S. Cl.
CPC .............. *A61M2025/0096* (2013.01); *A61M 2025/0175* (2013.01); *A61M 2025/105* (2013.01); *A61M 2025/1086* (2013.01); *A61M 2025/1093* (2013.01); *A61M 2210/0693* (2013.01)
USPC .................. 604/525; 604/528; 604/95.04

(56) References Cited

U.S. PATENT DOCUMENTS

| | | | |
|---|---|---|---|
| 5,464,395 | A | 11/1995 | Faxon et al. |
| 6,394,976 | B1 | 5/2002 | Winston et al. |
| 6,458,098 | B1 | 10/2002 | Kanesaka |
| 6,881,209 | B2 * | 4/2005 | Boatman et al. .............. 604/525 |
| 7,566,316 | B2 * | 7/2009 | McGuckin et al. .......... 604/6.16 |
| 7,691,080 | B2 | 4/2010 | Seward et al. |
| 7,883,492 | B2 | 2/2011 | Mittermeyer et al. |
| 2003/0167031 | A1 | 9/2003 | Odland |
| 2005/0049607 | A1 | 3/2005 | Hart et al. |
| 2006/0116636 | A1 | 6/2006 | Murphy et al. |
| 2008/0294096 | A1 | 11/2008 | Uber, III et al. |
| 2008/0319387 | A1 | 12/2008 | Amisar et al. |
| 2011/0224607 | A1 * | 9/2011 | Vogelbaum et al. ....... 604/96.01 |

FOREIGN PATENT DOCUMENTS

| | | |
|---|---|---|
| WO | WO 2010/141837 A1 | 12/2010 |
| WO | WO 2011/112800 A2 | 9/2011 |

* cited by examiner

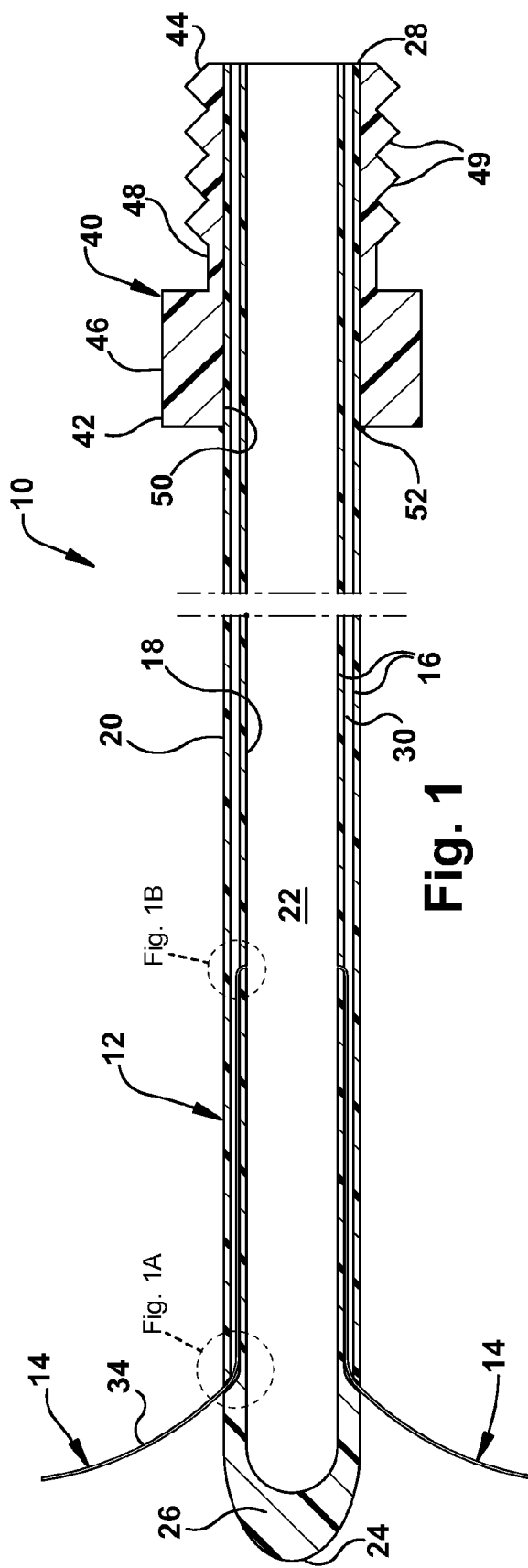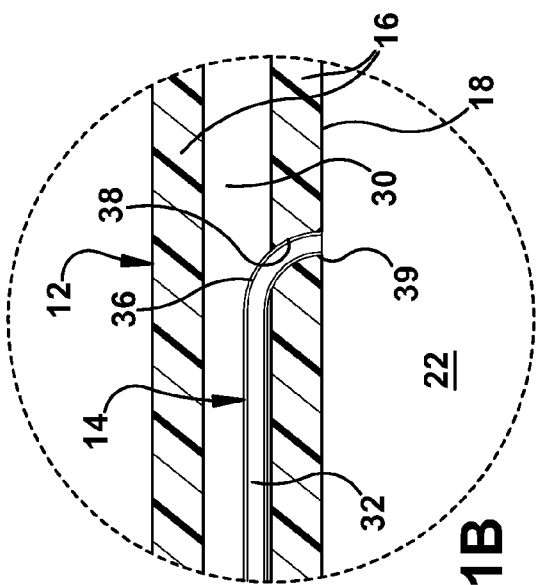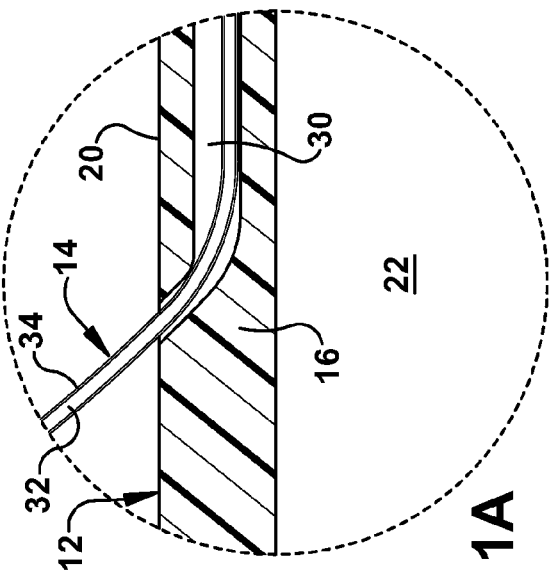

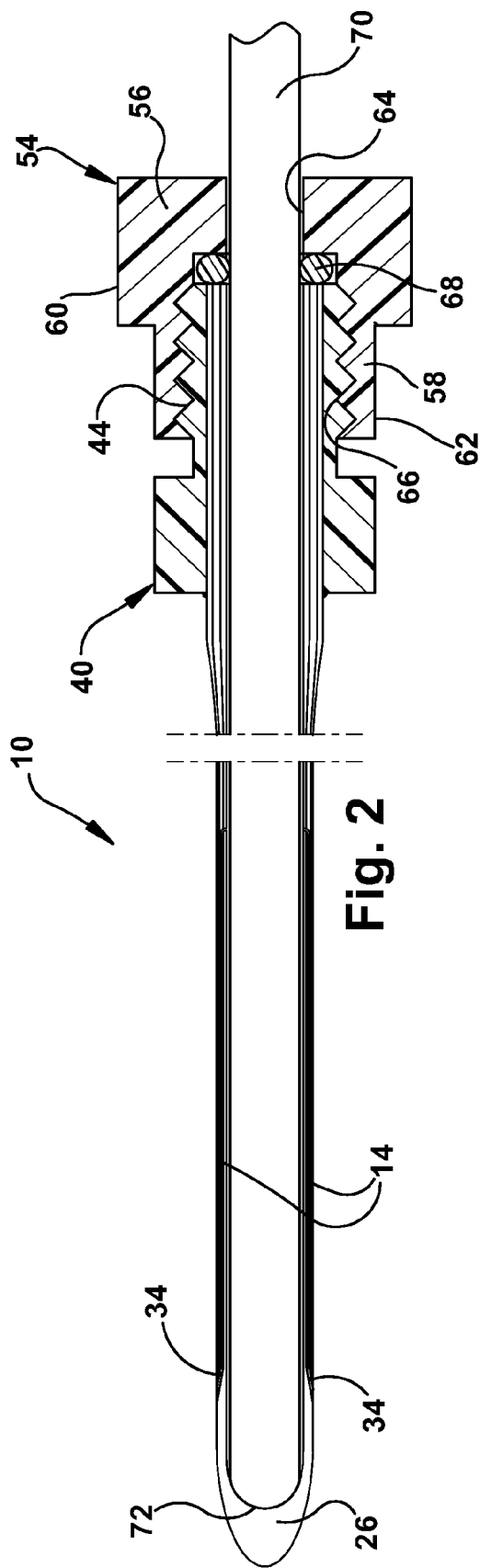
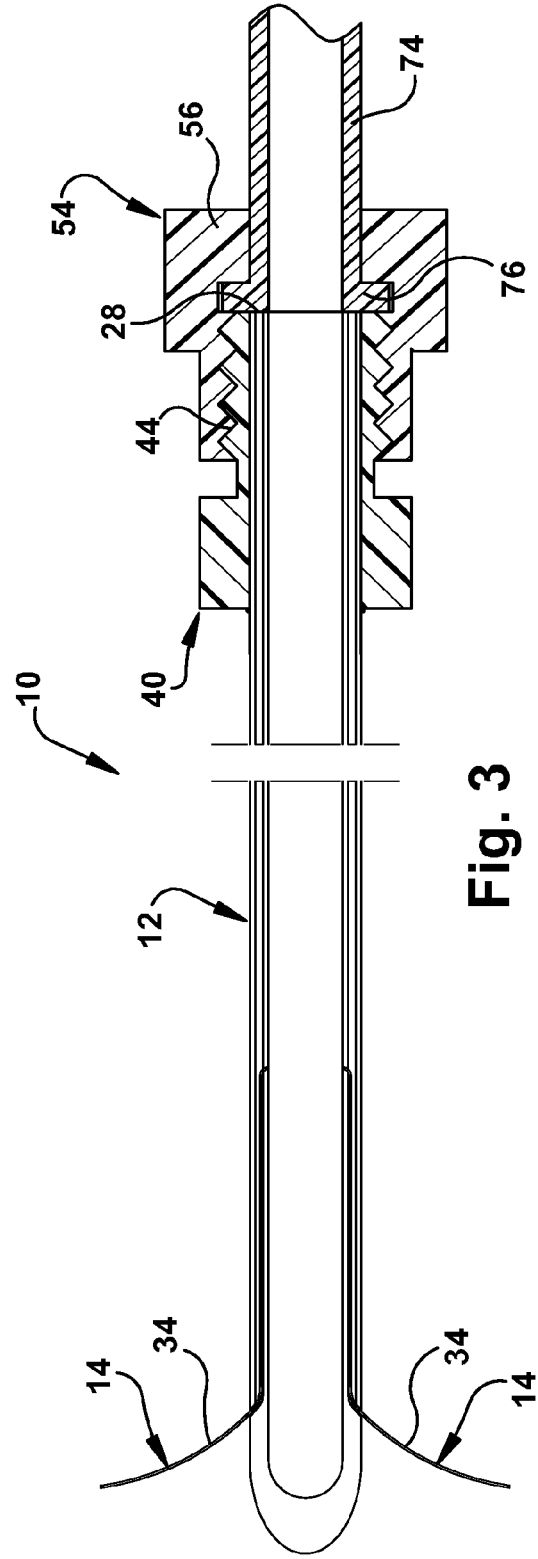

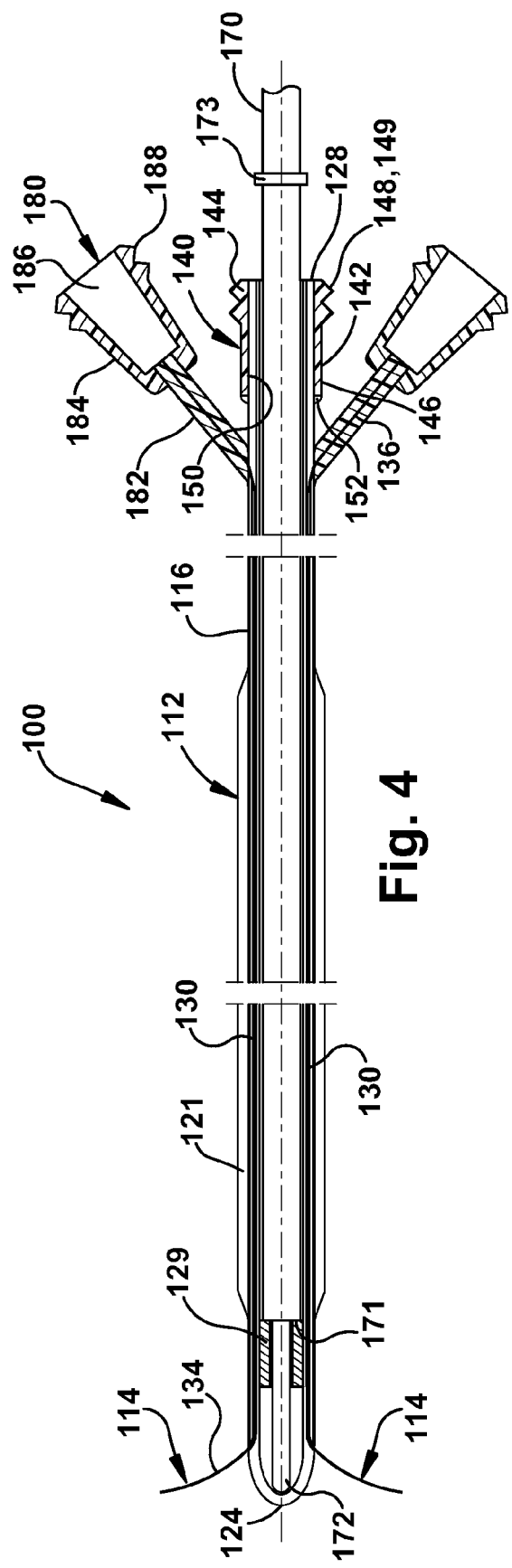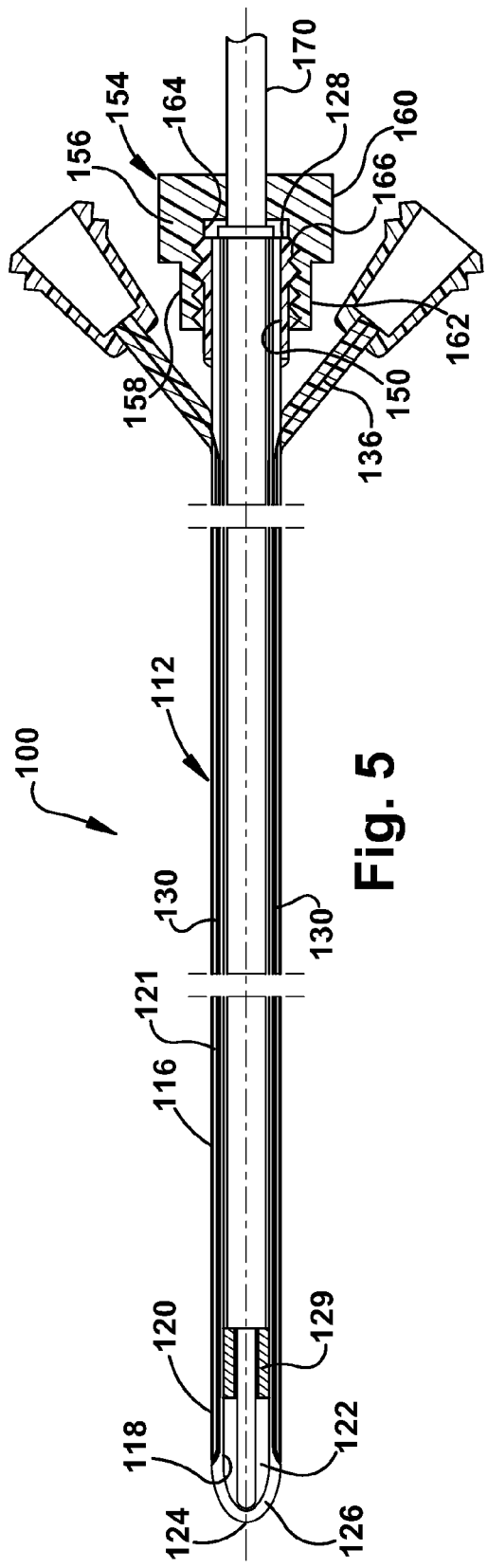

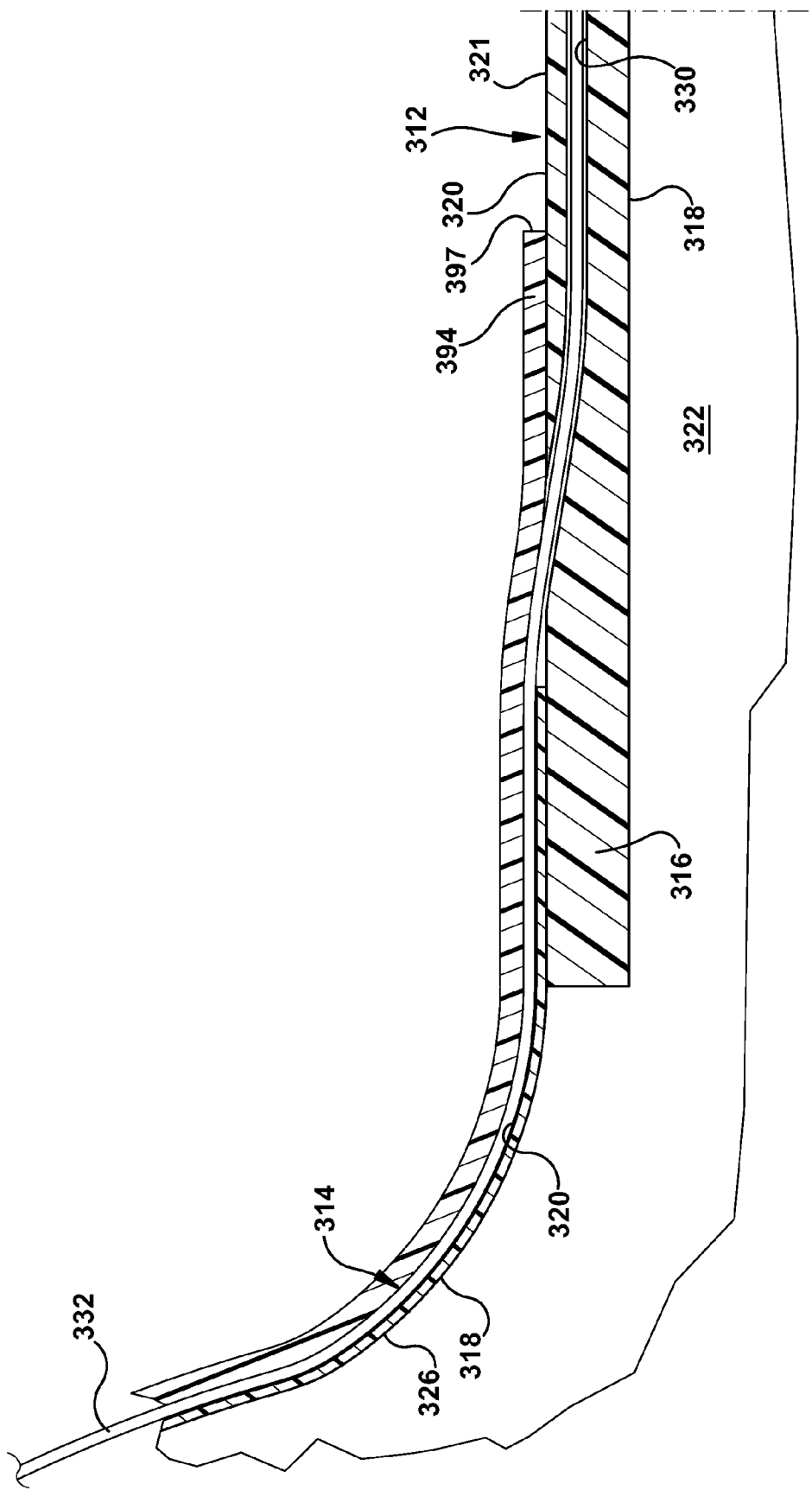

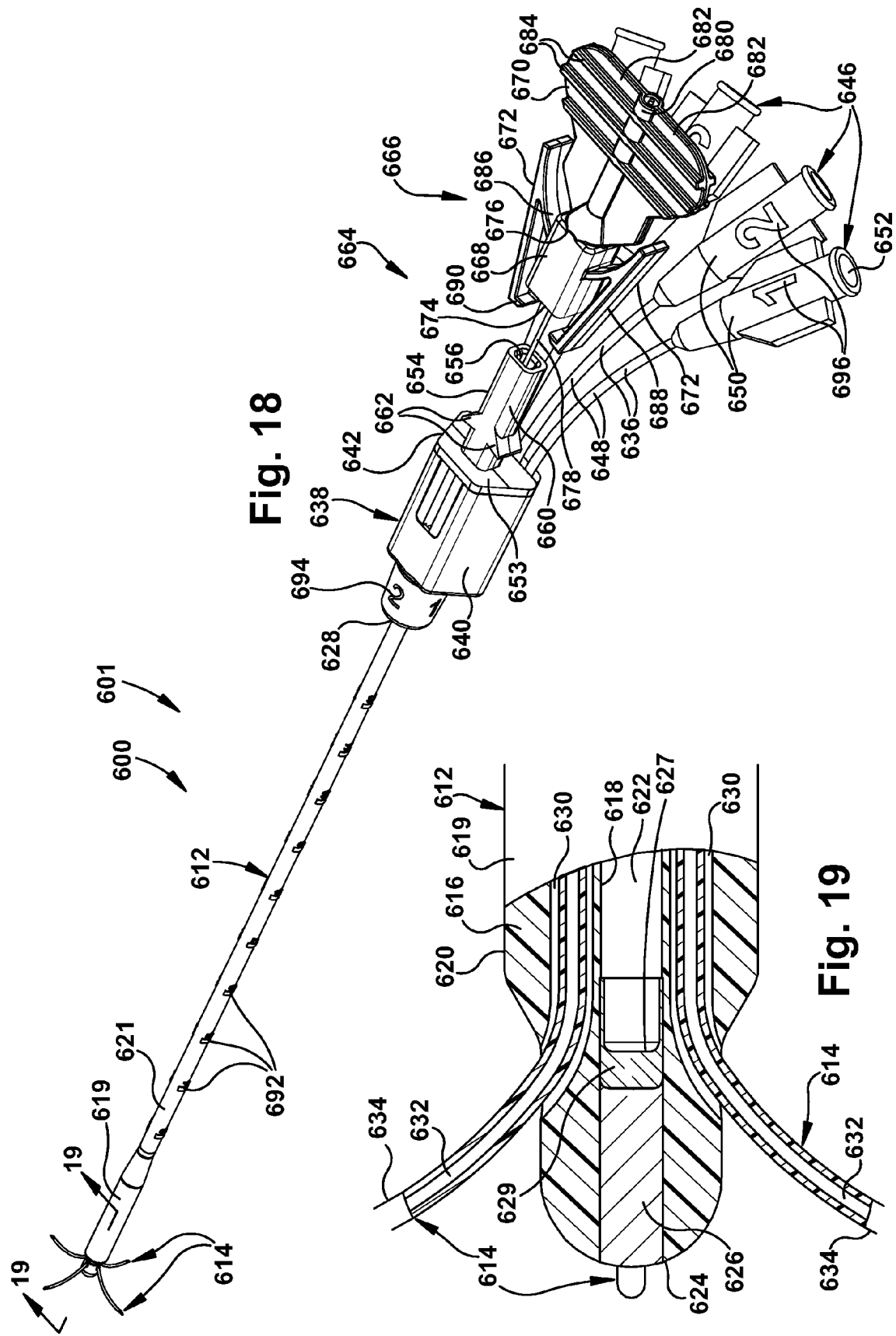

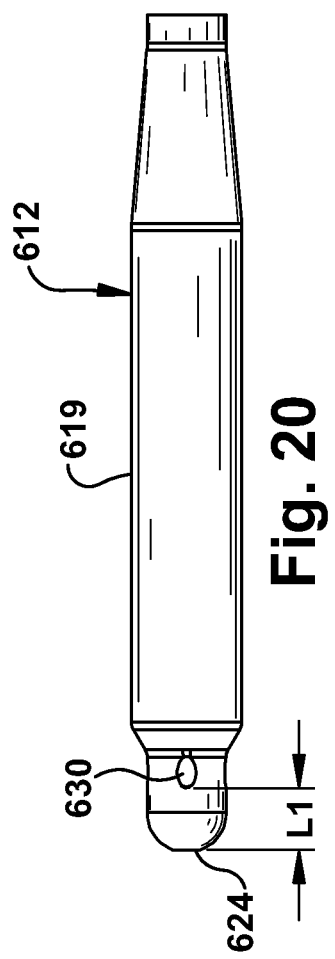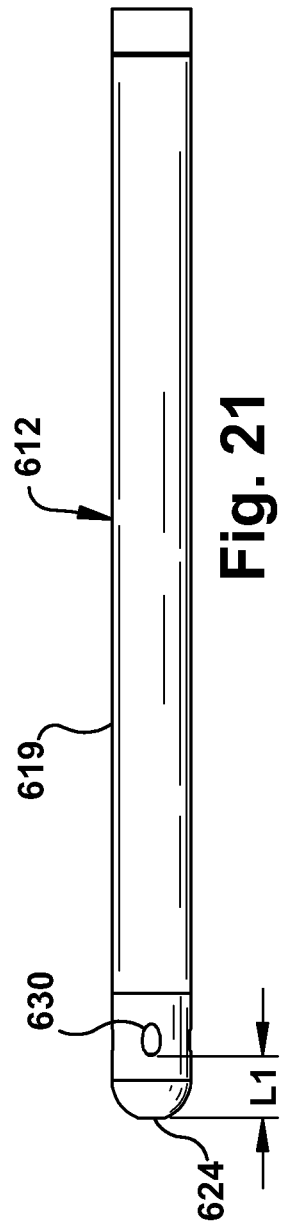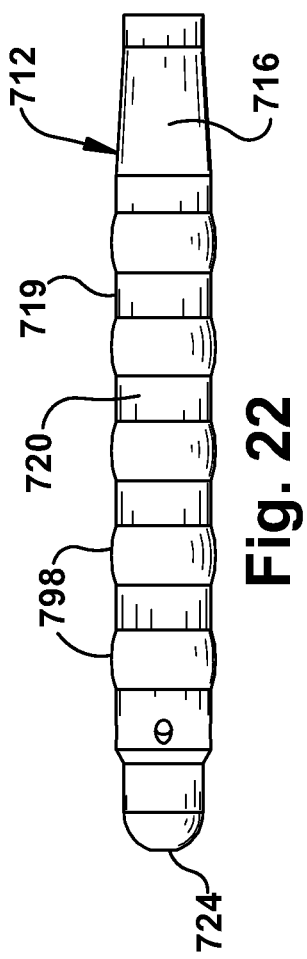

CATHETER ASSEMBLY

RELATED APPLICATIONS

This application claims priority from U.S. Provisional Patent Application Ser. No. 61/493,777, filed 6 Jun. 2011, U.S. patent application Ser. No. 13/044,963, filed 10 Mar. 2011, and U.S. Provisional Patent Application Ser. No. 61/312,401, filed 10 Mar. 2010. The subject matter of the aforementioned applications is hereby incorporated by reference in their entireties.

JOINT RESEARCH AGREEMENT

The presently claimed invention was made by or on behalf of one or more of the following parties to a joint research agreement: Parker Hannifin Corporation and The Cleveland Clinic Foundation. The joint research agreement was in effect on and before the date the claimed invention was made, and the claimed invention was made as a result of activities undertaken within the scope of the joint research agreement.

FIELD OF THE INVENTION

The present invention relates to a catheter assembly that comprises two connected catheters and, more particularly, to a catheter assembly in which one catheter is at least partially covered by a sheath portion of another catheter.

BACKGROUND OF THE INVENTION

Convection enhanced delivery ("CED") of a bioactive agent involves introducing a fluid containing the bioactive agent into a patient's tissue under pressure so that the fluid moves through the tissue via bulk flow. Implementing CED generally involves inserting multiple catheters into the tissue to be treated, such as cerebral tissue. To reduce the risk of hemorrhage and/or trauma to the tissue, it is desirable for the catheters to be microcatheters with small outside diameters.

SUMMARY OF THE INVENTION

The present invention is directed to a catheter assembly that comprises two connected catheters and, more particularly, to a catheter assembly in which one catheter is at least partially covered by a sheath portion of another catheter.

In accordance with an embodiment of the present invention, a catheter assembly comprises a first catheter including a wall with an inner surface at least partially defining a lumen. A second catheter is connected to the wall of the first catheter and is disposed outward of the inner surface of the wall. The second catheter is at least partially covered by a sheath portion of the first catheter. A first portion of the wall of the first catheter is made of a relatively low durometer elastomeric material and is relatively extensible. A second portion of the wall is formed of a relatively high durometer elastomeric material and is relatively inextensible.

In accordance with another embodiment of the invention, a catheter assembly comprises a first catheter including a wall with an inner surface at least partially defining a lumen extending lengthwise of the first catheter. A second catheter is at least partially disposed in the wall of the first catheter outward of the inner surface of the wall and extending lengthwise of the first catheter. A first portion of the wall of the first catheter is made of a relatively low durometer elastomeric material and is relatively extensible. A second portion of the wall is formed of a relatively high durometer elastomeric material and is relatively inextensible.

In accordance with still another embodiment of the present invention, a catheter assembly comprises a first catheter including a wall with an inner surface at least partially defining a first lumen. A second catheter includes a second lumen. The second lumen is disposed outside of the first lumen, and the first lumen is disposed outside of the second lumen. A first portion of the wall of the first catheter is made of a relatively low durometer elastomeric material and being relatively extensible. A second portion of the wall is formed of a relatively high durometer elastomeric material and is relatively inextensible. The second catheter is connected to the first portion of the wall of the first catheter. Extension of the first portion of the wall causes relative movement between the first portion of the wall and an adjacent, outwardly disposed portion of the second catheter.

In accordance with yet another embodiment of the present invention, a catheter apparatus comprises a first catheter including a wall with an inner surface at least partially defining a lumen. A first portion of the wall of the first catheter is made of a relatively low durometer elastomeric material and is relatively extensible. A second portion of the wall is formed of a relatively high durometer elastomeric material and is relatively inextensible. A second catheter is connected to the wall of the first catheter and is disposed outward of the inner surface of the wall. The second catheter is at least partially covered by a sheath portion of the first catheter. A control mechanism engages a stylet when disposed in the lumen and controls relative movement between the stylet and the first portion of the wall and consequent extension of the first portion of the wall.

In accordance with a further embodiment of the present invention, a catheter apparatus comprises a first catheter including a wall with an inner surface at least partially defining a lumen extending lengthwise of the first catheter. A first portion of the wall of the first catheter is made of a relatively low durometer elastomeric material and is relatively extensible. A second portion of the wall is formed of a relatively high durometer elastomeric material and is relatively inextensible. A second catheter is at least partially disposed in the wall of the first catheter outward of the inner surface of the wall and extending lengthwise of the first catheter. A control mechanism engages a stylet when disposed in the lumen and controls relative movement between the stylet and the first portion of the wall and consequent extension of the first portion of the wall.

In accordance with yet a further embodiment of the present invention, a catheter apparatus comprises a first catheter including a wall with an inner surface at least partially defining a first lumen extending lengthwise of the first catheter. A first portion of the wall of the first catheter is made of a relatively low durometer elastomeric material and is relatively extensible. A second portion of the wall is formed of a relatively high durometer elastomeric material and is relatively inextensible. A second catheter includes a second lumen. The second catheter is disposed outside of the first lumen, and the first lumen is disposed outside of the second lumen. The second catheter is connected to the first portion of the wall of the first catheter. Extension of the first portion of the wall causes relative movement between the first portion of the wall and an adjacent, outwardly disposed portion of the second catheter. A control mechanism engages a stylet when disposed in the first lumen and controls relative movement between the stylet and the first portion of the wall and consequent extension of the first portion of the wall.

BRIEF DESCRIPTION OF THE DRAWINGS

The foregoing and other features and advantages of the present invention will become apparent to one skilled in the art upon consideration of the following description of the invention and the accompanying drawings, in which:

FIG. 1 is a sectional view of a first embodiment of a catheter assembly in accordance with the present invention;

FIG. 1A is an enlarged sectional view of a first portion of the catheter assembly of FIG. 1;

FIG. 1B is an enlarged sectional view of a second portion of the catheter assembly of FIG. 1;

FIG. 2 is a sectional view of the catheter assembly of FIG. 1 in a longitudinally extended condition;

FIG. 3 is a sectional view of the catheter assembly of FIG. 1 in a non-extended condition;

FIG. 4 is a sectional view of a second embodiment of a catheter assembly in accordance with the present invention showing the catheter assembly in a non-extended condition;

FIG. 5 is a sectional view of the catheter assembly of FIG. 4 in a longitudinally extended condition;

FIG. 10A is an enlarged sectional view of a portion of the catheter assembly of FIG. 10;

FIG. 18 is a perspective view of a sixth embodiment of a catheter assembly in accordance with the present invention showing the catheter assembly in a non-extended condition;

FIG. 19 is an enlarged sectional view of a portion of the catheter assembly of FIG. 18;

FIG. 20 is a side view of a larger portion of the catheter assembly of FIG. 18 in a non-extended condition;

FIG. 21 is another side view of the portion of the catheter assembly shown in FIG. 20, but in an extended condition; and FIG. 22 is a side view of an alternative construction of the portion of the catheter assembly shown in FIG. 20.

DETAILED DESCRIPTION

Figure 4A:
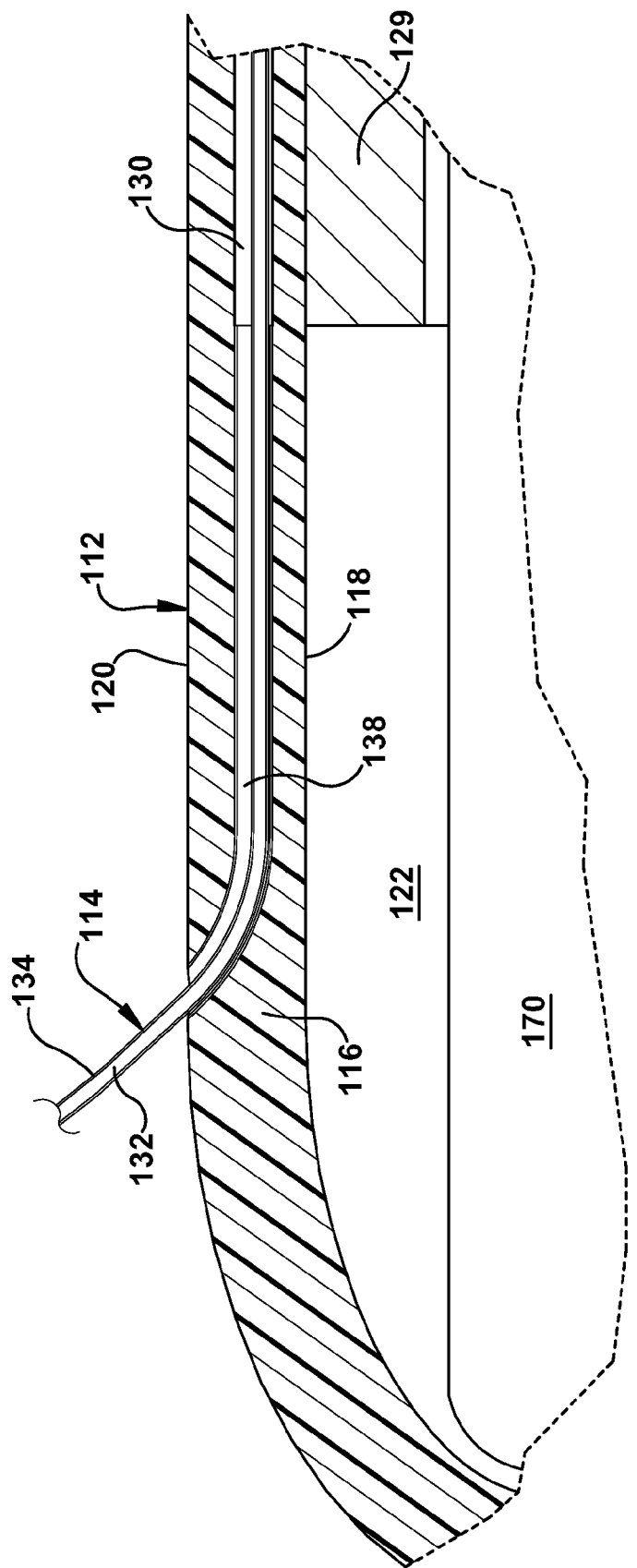
FIG. 4A is an enlarged sectional view of a portion of the catheter assembly of FIG. 4.

FIGS. 1 through 3 illustrate a catheter assembly 10, in accordance with an example of the present invention. The catheter assembly 10 includes a first or central catheter 12 and second or peripheral catheters 14, two of which are shown in FIG. 1. The central catheter 12 is made of a flexible and resilient biocompatible material, such as a medical grade silicone elastomer, and includes a longitudinally extending, tubular wall 16. The tubular wall 16 includes a radially inner surface 18 and a radially outer surface 20. Both the inner surface 18 and the outer surface 20 extend substantially the entire length of the central catheter 12. The inner surface 18 defines a central lumen 22 that also extends substantially the entire length of the central catheter 12. The central lumen 22 is closed at a distal end 24 of the central catheter 12 by a thickened end portion 26 of the wall 16. The central lumen 22 is open at the opposite, proximal end 28 of the central catheter 12.

Tunnels or passages 30 are formed in the wall 16 of the central catheter 12 and extend generally lengthwise of the central catheter. Two passages 30 are shown in FIG. 1 at diametrically opposite positions about the circumference of the wall 16. The wall 16 of the central catheter 12 may include more or fewer such passages 30, as desired. Each of the passages 30 is substantially identical in construction to the other passages 30. The passages 30 will therefore be described with reference to the passage 30 located uppermost in FIG. 1, portions of which are shown in enlarged views in FIGS. 1A and 1B.

Each passage 30 receives an associated peripheral catheter 14. The peripheral catheter 14 is thus disposed in the wall 16 of the central catheter 12, radially outward of the inner surface 18 of the wall 16 and, for a portion of its length, radially inward of the outer surface 20 of the wall 16. This portion of the length of the peripheral catheter 14 extends lengthwise substantially parallel to the central catheter 12. As can be seen from FIGS. 1A and 1B, the outer diameter of the peripheral catheter 14 is smaller than the thickness of the wall 16 of the central catheter 12 and smaller than the diameter of the associated passage 30.

Each peripheral catheter 14 has a central lumen 32, which is disposed outside of the central lumen 22 of the central catheter 12. Likewise, the central lumen 22 of the central catheter 12 is disposed outside of the central lumens 32 of the peripheral catheters 14. Each peripheral catheter 14 is formed of a biocompatible material, such as polytetrafluoroethylene ("PTFE"), that has sufficient rigidity to penetrate a patient's tissue and has also has sufficient flexibility and resilience to withstand being deflected and then return to a non-deflected position.

As best seen in FIGS. 1 and 1A, a distal end portion 34 of the peripheral catheter 14 can project radially outward of the outer surface 20 of the wall 16 of the central catheter 12 near the distal end 24 of the central catheter. To facilitate such radially outward projection of the peripheral catheter 14, the passage 30 in the wall 16 of the central catheter 12 turns radially outward and opens onto the outer surface 20 of the wall 16. The material of which the peripheral catheter 14 is made is also given a predetermined shape in the distal end portion 34 of the peripheral catheter 14 in the form of an outwardly directed curve or hook.

As best seen in FIGS. 1 and 1B, a proximal end portion 36 of the peripheral catheter 14 communicates with the central lumen 22 of the central catheter 12 at a location spaced from both the distal end 24 and the proximal end 28 of the central catheter. To facilitate such communication between the peripheral catheter 14 and the central catheter 12, a short connector passage 38 extends radially inward from the passage 30 in the wall 16 and opens onto the inner surface 18 of the wall 16 of the central catheter. The proximal end portion 36 of the peripheral catheter 14 is inserted into the connector passage 38 until an end surface of the peripheral catheter is flush with the inner surface 18 of the wall 16. A biocompatible adhesive material 39 fixes the proximal end portion 36 of the peripheral catheter 14 to the wall 16 of the central catheter 12. The central lumen 32 of the peripheral catheter 14 is thus in fluid communication with the central lumen 22 of the central catheter 12.

As a result of the foregoing construction, fluid may flow along the central lumen 22 of the central catheter 12, then into the central lumen 32 in the proximal end portion 36 of the peripheral catheter 14, and further into the distal end portion 34 of the peripheral catheter. The distal end of the peripheral catheter 14 is open so that fluid may flow out of the open distal end of the peripheral catheter.

The portion of the central catheter 12 adjacent its proximal end 28 is received in a tubular male connector 40, such as a Luer lock connector. The male connector 40 has an enlarged head portion 42 and an opposite threaded portion 44. The head portion 42 of the male connector 40 has an outer surface 46 formed in a rounded hexagonal shape with raised, longitudinally extending ridges at the corners of the hexagonal shape to facilitate manipulation of the male connector. The threaded portion 44 of the male connector 40 has an outer surface 48 in which a screw thread 49 is formed. An inner surface 50 of the male connector 40 extends through both the head portion 42 and the threaded portion 44 of the male connector and defines a central passage in the male connector. The portion of the central catheter 12 adjacent the proximal end 28 is received in the central passage of the male connector 40 with the threaded portion 44 of the male connector adjacent the open proximal end 28 of the central catheter and with the head portion 42 of the male connector closer to the distal end 24 of the central catheter 12. A biocompatible adhesive 52 fixes the head portion 42 of the male connector 40 to the outer surface 20 of the wall 16 of the central catheter 12.

In use, as shown in FIG. 2, the threaded portion 44 of the male connector 40 is received in a female connector 54, such as a female Luer lock connector. Like the male connector 40, the female connector 54 has an enlarged head portion 56 and an opposite threaded portion 58. The head portion 56 of the female connector 54 has an outer surface 60 formed in a rounded hexagonal shape with raised, longitudinally extending ridges at the corners of the hexagonal shape to facilitate manipulation of the female connector. The threaded portion 58 of the female connector 54 has a cylindrical outer surface 62. An inner surface 64 of the female connector 54 extends through both the head portion 56 and the threaded portion 58 of the female connector and defines a central passage in the female connector. The inner surface 64 includes a radial step such that the central passage of the female connector 54 has a larger diameter adjacent the threaded portion 58 of the female connector and a smaller diameter adjacent the head portion 56 of the female connector. A screw thread 66 is formed in the inner surface 64 of the female connector 54 adjacent the threaded portion 58 of the female connector.

The threaded portion 44 of the male connector 40 is received in the threaded portion 58 of the female connector 54 with the screw thread 49 in the outer surface 48 of the threaded portion 44 engaging the screw thread 66 formed in the inner surface 64 of the female connector. An O-ring 68 is received against the inner surface 64 of the female connector 54 in the larger diameter portion of the central passage of the female connector between the end of the threaded portion 44 of the male connector 40 and the head portion 56 of the female connector.

When the catheter assembly 10 is to be inserted into tissue, such as cerebral tissue, of a patient, a stylet 70, which formed of a relatively strong and rigid material, such as stainless steel, is inserted into the catheter assembly. The stylet 70 is inserted into the central passage of the female connector 54, past the O-ring 68, and into the central lumen 22 of the central catheter 12 until a rounded distal end 72 of the stylet contacts the thickened end portion 26 of the wall 16 of the central catheter. After the distal end 72 of the stylet 70 contacts the thickened end portion 26, the stylet continues to be pushed into the central catheter 12 and against the thickened end portion 26 of the wall 16 of the central catheter. The continued pressure of the stylet 70 against the thickened end portion 26 of the wall 16 causes the resilient material of which the wall 16 is made to stretch and thereby causes the wall 16 to extend or distend axially or lengthwise into a longitudinally extended condition.

Longitudinal stretching of the wall 16 causes the outer diameter of the wall to decrease or be reduced, as can be seen in FIG. 2 by comparing the diameter of the middle portion of the wall with the portion adjacent to the male connector 40. Stretching of the wall 16 of the central catheter 12 also causes the distal end portions 34 of the peripheral catheters 14 to be withdrawn into the passages 30 in the wall 16, as can be seen in FIG. 2, because the proximal end portions 36 of the peripheral catheters 14 are fixed to the wall 16. As they are withdrawn into the passages 30, the distal end portions 34 of the peripheral catheters 14 are deflected from their outwardly curving, predetermined shape and are constrained in a generally straight configuration by the wall 16 of the central catheter 12. When the peripheral catheters 14 have been fully withdrawn or retracted into the wall 16 of the central catheter 12, the outer surface 20 of the wall 16 of the central catheter appears essentially smooth and uninterrupted. The wall 16 of the central catheter 12 thus functions as a sheath portion of the central catheter and covers the distal end portions 34 of the peripheral catheters 14.

The stylet 70 can then be used to insert the extended central catheter 12 and the peripheral catheters 14 into the tissue of a patient. To facilitate such use of the stylet 70, the female connector 54 may be screwed further onto the male connector 40 to cause radially inward bulging of the O-ring 68. Radially inward bulging of the O-ring 68 causes the O-ring to grip the outer surface of the stylet 70 tightly and thus to hold the stylet longitudinally in position in the extended central catheter 12. Because the outer diameter of the central catheter 12 has been reduced due to the lengthwise extension or distension of the central catheter, the opening that will be formed in the patient's tissue is smaller than it would be otherwise. Because the distal end portions 34 of the peripheral catheters 14 have been withdrawn into the wall 16 of the central catheter 12, the peripheral catheters do not interfere with the insertion of the central catheter into the patient's tissue. When the distal end 24 of the central catheter 12 is appropriately positioned in a patient's tissue, the stylet 70 is held so as to maintain the distal end of the central catheter in position. The female connector 54 may then be at least partially unscrewed from the male connector 40 so that the O-ring 68 no longer tightly grips the outer surface of the stylet 70. With the stylet 70 held in position and the O-ring 68 no longer tightly gripping the stylet, the resilience of the extended central catheter 12 pulls the proximal end 28 of the central catheter along the stylet toward the distal end 24 of the central catheter. The central catheter 12 thus returns resiliently to its initial, non-extended length while the distal end 24 of the central catheter remains in position.

When the central catheter 12 resiliently returns to its initial, non-extended length and the wall 16 of the central catheter resiliently likewise returns from its longitudinally extended condition to its initial, non-extended length, the distal end portions 34 of the peripheral catheters 14 are no longer withdrawn into the wall 16. The distal end portions 34 of the peripheral catheters 14 instead project from the outer surface 20 of the wall 16 of the central catheter 12 and again assume their outwardly curved, predetermined shape. As the distal end portions 34 of the peripheral catheters 14 assume their outwardly curved, predetermined shape, the peripheral catheters penetrate the patient's tissue and extend into the patient's tissue away from the central catheter 12 in a radial array. In addition, as the wall 16 of the central catheter 12 resiliently returns to its initial length, the outer diameter of the wall increases from its reduced condition back to its original dimension. The increase in the outer diameter of the wall 16 of the central catheter 12 causes the outer surface 20 of the wall 16 to press tightly against adjacent surfaces of the patient's tissue. The resulting close fit between the outer surface 20 of the wall 16 and the adjacent surfaces of the patient's tissue helps to prevent fluid introduced into the tissue by the peripheral catheters 14 from flowing back along the outer surface of the wall toward the proximal end 28 of the central catheter 12.

With the central and peripheral catheters 12 and 14 of the catheter assembly 10 appropriately positioned in the patient's tissue, therapeutic treatment of the tissue with a bioactive material can begin. To introduce the bioactive material, the stylet 70 is withdrawn entirely from the central lumen 22 of the central catheter and the catheter assembly 10 and from the female connector 54. The threaded portion 58 of the female connector 54 is then unscrewed from the threaded portion 44 of the male connector 40 and the O-ring 68 is removed. A length of tubing 74 is inserted into the central passage of the female connector 54 until an enlarged distal end 76 of the tubing 74 engages the head portion 56 of the female connector. When the female connector 54 is again screwed onto the male connector 40, the enlarged distal end 76 of the tubing 74 is trapped in the central passage of the female connector between the threaded portion 44 of the male connector and head portion 56 of the female connector, as shown in FIG. 3. As the male and female connectors 40 and 54 are screwed together more tightly, the tubing 74 is sealed against the connectors and against the proximal end 28 of the central catheter 12.

A proximal end (not shown) of the tubing 74 is then attached to a device (not shown), such as a pump, for delivering a fluid, such as a liquid, under pressure to the catheter assembly 10 and thus into a patient's tissue. The fluid contains a bioactive material, such as a pharmaceutical material, and is delivered from the tubing 74 into the central lumen 22 of the central catheter 12. From the central catheter 12, the fluid containing the bioactive material is delivered through the inner surface 18 of the wall 16 of the central catheter into the central lumens 32 of the proximal end portions 36 of the peripheral catheters 14. The fluid flows along the central lumens 32 of the peripheral catheters 14 until it reaches the open ends of the distal end portions 34 of the peripheral catheters and is thereby introduced into the patient's tissue. When the patient's treatment is completed, the catheter assembly 10 may be removed by disconnecting the tubing 74 from the catheter assembly, reintroducing the stylet 70 into the catheter assembly to extend or distend the central catheter 12, and then withdrawing the catheter assembly and stylet from the patient's tissue.

FIGS. 4 through 5 illustrate a catheter assembly 100 that is constructed in accordance with a second example of the present invention. The catheter assembly 100 includes a first or central catheter 112 and second or peripheral catheters 114, two of which are shown in FIGS. 4 and 5. The central catheter 112 is made of a flexible and resilient biocompatible material, such as such as a medical grade silicone elastomer, and includes a longitudinally extending, tubular wall 116. The tubular wall 116 includes a radially inner surface 118 and a radially outer surface 120. Both the inner surface 118 and the outer surface 120 extend substantially the entire length of the central catheter 112. The outer surface 120 is separated from the inner surface 118 by a greater distance in a middle portion of the central catheter 112 than adjacent its distal and proximal ends 124 and 128, respectively. As a consequence, the wall 116 has a greater thickness in a middle portion 121 of its length than at either end of the wall.

The inner surface 118 of the wall 116 defines a central lumen 122 that extends substantially the entire length of the central catheter 112. The central lumen 122 is closed at the distal end 124 of the central catheter 112 by a thickened end portion 126 of the wall 116. The central lumen 122 is open at the opposite, proximal end 128 of the central catheter 112. A tubular stopper element 129 is disposed in the central lumen 122 of the central catheter 112 adjacent an end of the thickened middle portion 121 of the wall 116 closest to the distal end 124 of the central catheter. The stopper element 129, which may be formed of medical grade tubing, is secured to the inner surface 118 of the wall 116 by a biocompatible adhesive (not shown).

As best shown in FIG. 4A, tunnels or passages 130 are formed in the wall 116 of the central catheter 112 and extend generally lengthwise of the central catheter. Two passages 130 are shown in FIGS. 4 and 5 at diametrically opposite positions about the circumference of the wall 116. The wall 116 of the central catheter 112 may include more or fewer such passages 130, as desired. Each of the passages 130 is substantially identical in construction to the other passages 130. Like the passages 30 of the catheter assembly 10 shown in FIGS. 1-3, each of the passages 130 receives an associated peripheral catheter 114. The peripheral catheters 114 are thus disposed in the wall 116 of the central catheter 112, radially outward of the inner surface 118 of the wall 116 and, for a major portion of their lengths, radially inward of the outer surface 120 of the wall 116. This portion of the lengths of the peripheral catheters 114 extends lengthwise substantially parallel to the central catheter 112. As can be seen from FIG. 4A, the outer diameter of each of the peripheral catheters 114 is smaller than the thickness of the wall 116 of the central catheter 112 and smaller than the diameter of the associated passage 130.

Each peripheral catheter 114 has a central lumen 132, which is disposed outside of the central lumen 122 of the central catheter 112. Likewise, the central lumen 122 of the central catheter 112 is disposed outside of the central lumens 132 of the peripheral catheters 114. Each peripheral catheter 114 is formed of a biocompatible material, such as PTFE, that has sufficient rigidity to penetrate a patient's tissue and also has sufficient flexibility and resilience to withstand being deflected and then return to a non-deflected position.

As best seen in FIGS. 4 and 4A, a distal end portion 134 of each peripheral catheter 114 can project radially outward of the outer surface 120 of the wall 116 of the central catheter 112 near the distal end 124 of the central catheter. To facilitate such radially outward projection of the peripheral catheter 114, the passage 130 in the wall 116 of the central catheter 112 curves radially outward and opens onto the outer surface 120 of the wall 116. A short length of tubing 138, such as PTFE tubing, is positioned in the radially curved portion of the passage 130 and is bonded to the wall 116 to act as a bearing surface for sliding movement of the peripheral catheter 114 relative to the wall 116. The distal end portion 134 of the peripheral catheter 114 is given a predetermined shape in the form of an outwardly directed curve or hook.

Unlike the peripheral catheters 14 of the catheter assembly 10, the central lumen 132 of the proximal end portion 136 of each peripheral catheter 114 does not communicate with the central lumen 122 of the central catheter 112. Instead, the proximal end portion 136 of each peripheral catheter 114 projects radially outward of the outer surface 120 of the wall 116 of the central catheter 112 near the proximal end 128 of the central catheter. The proximal end portion 136 of each peripheral catheter 114 is associated with a fluid inlet port or injection port assembly 180, which receives the proximal end portion of its associated peripheral catheter.

Each injection port assembly 180 includes a sleeve portion 182 and connector portion 184, such as a Luer lock connector. The sleeve portion 182 and connector portion 184 of each injection port assembly 180 are joined to one another and may be formed in one piece. The sleeve portion 182 of each injection port assembly 180 is elongated and extends between its associated connector portion 184 and an area on the outer surface 120 of the wall 116 of the central catheter 112 from which the proximal end portion 136 of the associated peripheral catheter 114 projects. The sleeve portion 182 surrounds and is bonded to the proximal end portion 136 of the associated peripheral catheter 114 and helps to protect the proximal end portion. The sleeve portion 182 is also adhesively bonded or otherwise secured to the outer surface 120 of the wall 116 of the central catheter 112, thereby fixing the proximal end portion 136 of the associated peripheral catheter 114 to the wall 116 of the central catheter.

The proximal end portion 136 of each peripheral catheter 114 extends into the connector portion 184 of its associated injection port assembly 180. The central lumen 132 of the peripheral catheter 114 communicates with a central lumen 186 in the connector portion 184 of the injection port assembly 180. An outer surface 188 of the connector portion 184 is threaded to facilitate attachment of a second connector (not shown) and tubing (not shown) for delivering a fluid to the connector portion and thus to the peripheral catheter 114. Such a fluid may flow along the central lumen 132 of the peripheral catheter 114 from its proximal end portion 136 into the distal end portion 134 of the peripheral catheter. The distal end of the peripheral catheter 114 is open so that fluid may flow out of the open distal end of the peripheral catheter.

The portion of the central catheter 112 adjacent the proximal end 128 is received in a tubular male connector 140, such as a male Luer lock connector. The male connector 140 has a head portion 142 and an opposite threaded portion 144. The head portion 142 of the male connector 140 has an outer surface 146 formed for manual manipulation to facilitate attachment of another connector, as shown in FIG. 5. The threaded portion 144 of the male connector 140 has an outer surface 148 in which a screw thread 149 is formed. An inner surface 150 of the male connector 140 extends through both the head portion 142 and the threaded portion 144 of the male connector and defines a central passage in the male connector. The portion of the central catheter 112 adjacent its proximal end 128 is received in the central passage of the male connector 140 with the threaded portion 144 of the male connector adjacent the open proximal end of the central catheter and with the head portion 142 of the male connector closer to the distal end 124 of the central catheter 112. A biocompatible adhesive 152 fixes the head portion 142 of the male connector 140 to the outer surface 120 of the wall 116 of the central catheter 112.

When the catheter assembly 100 is ready to be inserted into tissue, such as cerebral tissue, of a patient, a stylet 170 formed of a relatively strong and rigid material, such as stainless steel, is inserted into the catheter assembly. Near its rounded distal end 172, the stylet 170 has an annular, radially extending surface 171 that provides a step encircling the stylet. Near its proximal end, the stylet 170 is encircled by an annular stroke limiter 173 that is fixed to the stylet. The stylet 170 is inserted into the central passage of the male connector 140 and then into the central lumen 122 of the central catheter 112 until the radially extending surface 171 contacts the stopper element 129 secured to the inner surface 118 of the wall 116 of the central catheter.

After the radially extending surface 171 of the stylet 170 contacts the stopper element 129, the stylet continues to be pushed into the central catheter 112 and against the stopper element until the stroke limiter 173 contacts the proximal end 128 of the central catheter and the adjacent end of the threaded portion 144 of the male connector 140. The continued pressure of the stylet 170 against the stopper element 129 causes the resilient material of which the wall 116 is made to stretch and thereby causes the wall 116 to extend or distend axially or lengthwise into a longitudinally extended condition. This stretching of the wall 116 occurs primarily in the thickened middle portion 121 of the wall because the stopper element 129 is bonded to the inner surface 118 of the wall and effectively transfers the force applied by the stylet to the wall 116 adjacent the end of the middle portion closest to the distal end 124 of the central catheter 112. Adjacent the opposite end of the thickened middle portion 121 of the wall 116, the peripheral catheters 114 are adhesively bonded to the sleeve portions 182 of the injection port assemblies 180 and are also adhesively bonded to the surface of the wall 116 that defines the passage 130. These adhesive bonds effectively restrict or prevent stretching of the wall 116 adjacent the proximal end 128 of the central catheter 112.

Stretching of the wall 116 causes the outer diameter of the wall to decrease or be reduced, as can be seen in FIG. 5 by comparing the diameter of the middle portion 121 of the wall with the portion adjacent the stopper element 129. Stretching of the wall 116 of the central catheter 112 also causes the distal end portions 134 of the peripheral catheters 114 to be withdrawn into the passages 130 in the wall 116, as shown in FIG. 5, because the proximal end portions 136 of the peripheral catheters are fixed to the injection port assemblies 180 and to the surfaces of the wall 116 that define the passages. As they are withdrawn into the passages 130, the distal end portions 134 of the peripheral catheters 114 are deflected from their outwardly curving, predetermined shape and are constrained in a generally straight configuration by the wall 116 of the central catheter 112. When the peripheral catheters 114 have been fully withdrawn or retracted into the wall 116 of the central catheter 112, the outer surface 120 of the wall 116 of the central catheter appears essentially smooth and uninterrupted. The wall 116 of the central catheter 112 thus functions as a sheath portion of the central catheter and covers the distal end portions 134 of the peripheral catheters 114.

When the stylet 170 reaches the end of its stroke, as determined by contact between the stroke limiter 173 and the proximal end 128 of the central catheter and the adjacent end of the threaded portion 144 of the male connector 140, the stylet may be secured in place to facilitate coordinated manipulation of the stylet and the catheter assembly 100. As best seen in FIG. 5, the threaded portion 144 of the male connector 140 may be received in a female connector 154. The female connector 154 has an enlarged head portion 156 and an opposite threaded portion 158. The head portion 156 of the female connector 154 has an outer surface 160 formed in a rounded hexagonal shape with raised, longitudinally extending ridges at the corners of the hexagonal shape to facilitate manipulation of the female connector. The threaded portion 158 of the female connector 54 has a cylindrical outer surface 162. An inner surface 164 of the female connector 154 extends through both the head portion 156 and the threaded portion 158 of the female connector and defines a central passage in the female connector. The inner surface 164 includes a radial step such that the central passage of the female connector 154 has a larger diameter adjacent the threaded portion 158 of the female connector and a smaller diameter adjacent the head portion 156 of the female connector. A screw thread 166 is formed in the inner surface 164 of the female connector 154 adjacent the threaded portion 158 of the female connector.

The threaded portion 144 of the male connector 140 is received in the threaded portion 158 of the female connector 154 with the screw thread 149 in the outer surface 148 of the threaded portion 144 engaging the screw thread 166 formed in the inner surface 164 of the female connector. An annular washer (not shown), which may be formed of PTFE, for example, may be received against the inner surface 164 of the female connector 154 in the larger diameter portion of the central passage of the female connector between the end of the threaded portion 144 of the male connector 140 and the head portion 156 of the female connector.

When the female connector 154 is screwed onto the male connector 140, the stroke limiter 173 of the stylet 170 is trapped between the threaded portion 144 of the male connector and head portion 156 of the female connector. The stylet 170 and the catheter assembly 100 then tend to move more consistently as a single unit and can be manipulated more easily and accurately. In particular, the stylet 170 can then be used to insert the extended central catheter 112 and the peripheral catheters 114 into the tissue of a patient. Because the outer diameter of the central catheter 112 has been reduced due to the lengthwise extension or distension of the central catheter, the opening formed in the patient's tissue is smaller than it would be otherwise. Because the distal end portions 134 of the peripheral catheters 114 have been withdrawn into the wall 116 of the central catheter, the peripheral catheters do not interfere with the insertion of the central catheter into the patient's tissue. When the distal end 124 of the central catheter 112 is appropriately positioned in a patient's tissue, the stylet 170 is held so as to maintain the distal end of the central catheter in position. The female connector 154 may then be unscrewed from the male connector 140 so that the stroke limiter 173 of the stylet 170 is no longer trapped between the threaded portion 144 of the male connector and head portion 156 of the female connector. With the stylet 70 held in position and the stroke limiter 173 no longer trapped between the male and female connectors 140 and 154, respectively, the resilience of the extended central catheter 112 pulls the proximal end 128 of the central catheter along the stylet toward the distal end 124 of the central catheter. The central catheter 112 thus returns resiliently to its initial, non-extended length while the distal end 124 of the central catheter remains in position.

When the central catheter 112 resiliently returns to its initial, non-extended length and the wall 116 of the central catheter likewise resiliently returns from its longitudinally extended condition to its initial, non-extended length, the distal end portions 134 of the peripheral catheters 114 are no longer withdrawn into the wall 116. The distal end portions 134 of the peripheral catheters 114 instead project from the outer surface 120 of the wall 116 of the central catheter and assume their outwardly curved, predetermined shape. As the distal end portions 134 of the peripheral catheters 114 assume their outwardly curved, predetermined shape, the peripheral catheters 114 penetrate the patient's tissue and extend into the patient's tissue away from the central catheter 112 in a radial array. In addition, as the wall 116 of the central catheter 112 resiliently returns to its initial length, the outer diameter of the wall, particularly the middle portion 121, increases from its reduced condition back to its original dimension. The increase in the outer diameter of the wall 116 of the central catheter 112 causes the outer surface 120 of the wall 116 to press tightly against adjacent surfaces of the patient's tissue. The resulting close fit between the outer surface 120 of the wall 116 and the adjacent surfaces of the patient's tissue helps to prevent fluid introduced into the tissue by the peripheral catheters 114 from flowing back along the outer surface of the wall toward the proximal end 128 of the central catheter 112.

With the central and peripheral catheters 112 and 114 of the catheter assembly 100 appropriately positioned in the patient's tissue, therapeutic treatment of the tissue with a bioactive material can begin. To introduce the bioactive material, the stylet 170 is withdrawn entirely from the central lumen 122 of the central catheter 112 and the catheter assembly 100 and from the male connector 140. The threaded outer surface 188 of the connector portion 184 of each injection port assembly 180 is connected with a connector (not shown) and the distal end of a length of tubing (not shown). A proximal end (not shown) of the tubing is attached to a device (not shown), such as a pump, for delivering a fluid, such as a liquid. The fluid contains a bioactive material, such as a pharmaceutical material, and is delivered from the tubing into the central lumen 186 of the connector portion 184 of the injection port assembly 180 and then into the central lumen 132 of the associated peripheral catheter 114. The fluid flows along the central lumen 132 of the peripheral catheter 114 until it reaches the open end of the distal end portion 134 of the peripheral catheter and is thereby introduced into the patient's tissue. When the patient's treatment is completed, the catheter assembly 100 may be removed by reintroducing the stylet 170 into the catheter assembly to extend or distend the central catheter 112 and then withdrawing the catheter assembly from the patient's tissue.

In one particular embodiment of a catheter in accordance with FIGS. 4 through 5, the central catheter 112 is formed of a medical grade silicone rubber, which is available as product number MED 4901 from Nusil Silicone Technology of Carpinteria, Calif., U.S.A. The nominal outside diameter of the central catheter 112 is between about 2.0 mm and about 2.5 mm. The peripheral catheters 114 are formed of PTFE medical grade tubing with a nominal inside diameter of about 0.203 mm (0.008 inches), a wall thickness of about 0.076 mm (0.003 inches), and a nominal outside diameter of about 0.356 mm (0.014 inches). The distal end portions 134 of the peripheral catheters 114 project outwardly from the outer surface 120 of the wall 116 of the central catheter 112 a distance from about 10 mm to about 20 mm. In areas where the peripheral catheters 114 are to be bonded to the central catheter 112 or another element of the catheter assembly 100, the outer surfaces of the peripheral catheters are etched to enhance bonding and a silicone adhesive, such as product number 1137 from Nusil Silicone Technology of Carpinteria, Calif., U.S.A., is used. The numerical values set forth above and other numerical values set forth in the present application are given by way of example only and other values may be used with satisfactory results.

FIGS. 6 through 9 illustrate a catheter assembly 200 that is constructed in accordance with a third example of the present invention. The catheter assembly 200 includes a first or central catheter 212 and second or peripheral catheters 214, which are shown schematically in FIGS. 7-9. The central catheter 212 is made of a flexible and resilient biocompatible material, such as a medical grade silicone elastomer, and includes a wall 216. The wall 216 includes a radially inner surface 218 and a radially outer surface 220. Both the inner surface 218 and the outer surface 220 extend substantially throughout the central catheter 212. The inner surface 218 defines a central lumen 222 that also extends substantially throughout the central catheter 212.

Figure 7:
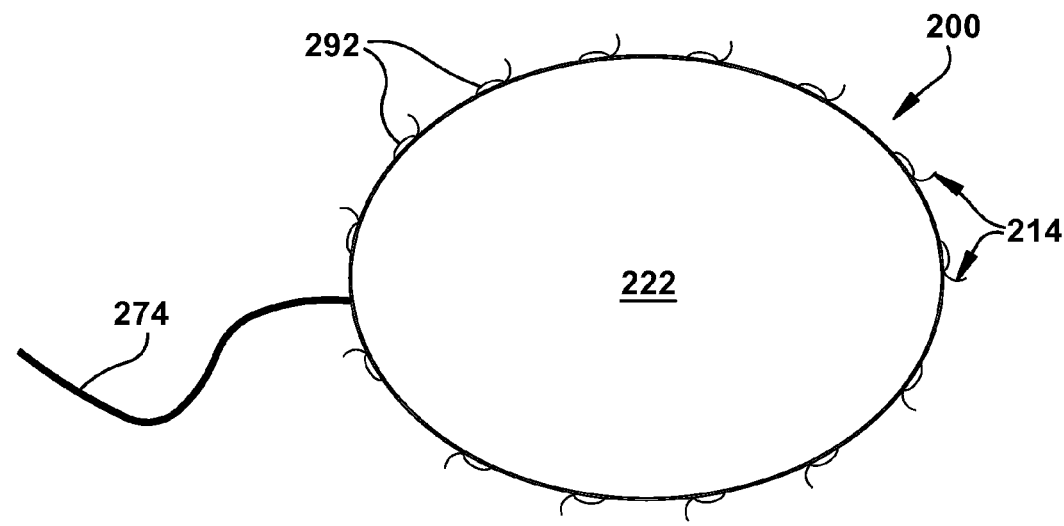
FIG. 7 is a schematic view of the catheter assembly of FIG. 6 in an extended condition.

The central lumen 222 is closed at a distal end 224 of the central catheter 212 by a portion of the wall 216. The central lumen 222 is open at the opposite, proximal end 228 of the central catheter 212. The open proximal end 228 of the central lumen 222 is connected to and communicates with a length of tubing 274. The tubing 274 delivers a fluid to the central lumen 222 for inflating or distending the central catheter 212. When inflated or distended, as shown in FIG. 7, the central catheter 212 resembles a balloon and can occupy a space or volume that has a relatively large radial dimension. The central catheter 212 is thus suitable for use in a tissue cavity, such as a resection cavity from which a tumor has been surgically removed.

Figure 8:
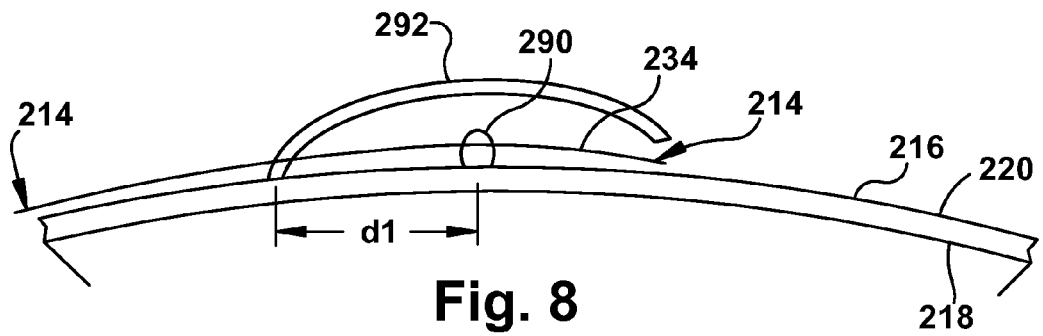
FIG. 8 is an enlarged schematic view of a portion of the catheter assembly of FIG. 6.
Figure 9:
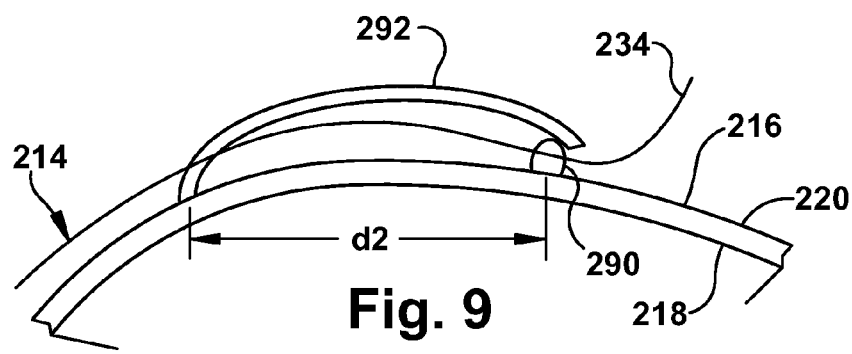
FIG. 9 is an enlarged schematic view of a portion of the catheter assembly of FIG. 7.

Unlike the embodiments of FIGS. 1-3 and FIGS. 4-5, tunnels or passages need not be formed in the wall 216 of the central catheter 212 to receive the peripheral catheters 214. Instead, the peripheral catheters 214 may be positioned against the outer surface 220 of the wall 216 of the central catheter 212, as shown in FIGS. 8 and 9. Each peripheral catheter 214 is thus disposed radially outward of the inner surface 118 of the wall 116 and radially outward of the outer surface 220 of the wall 216. Each peripheral catheter also extends lengthwise in the same general direction as the central catheter 212. As indicated in FIGS. 8 and 9, the outer diameter of each peripheral catheter 214 is smaller than the thickness of the wall 216 of the central catheter 212. Each peripheral catheter 214 has a central lumen (not shown), which is disposed outside of the central lumen 222 of the central catheter 212. Likewise, the central lumen 222 of the central catheter 112 is disposed outside of the central lumens (not shown) of the peripheral catheters 214. Each peripheral catheter 214 is formed of a biocompatible material, such as PTFE, that has sufficient rigidity to penetrate a patient's tissue and also has sufficient flexibility and resilience to withstand being deflected and then return to a non-deflected position.

As best seen in FIG. 9, a distal end portion 234 of each peripheral catheter 214 can project radially outward of the outer surface 220 of the wall 216 of the central catheter 212. To facilitate such radially outward projection of the peripheral catheter 214, the distal end portion 234 of the peripheral catheter is given a predetermined shape in the form of an outwardly directed curve or hook. The distal end portion 234 of each peripheral catheter 214 is also fixed or immovably attached to a point on the outer surface 220 of the wall 216 of the central catheter 212 by an associated attachment 290, such as a small mass of silicone elastomer bonded to the outer surface. Each peripheral catheter 214 has its own, individual attachment point and associated attachment 290.

To constrain the distal end portion 234 of each peripheral catheter 214 and maintain the distal end portion against the wall 216 of the central catheter, the distal end portion is covered by an associated sheath 292. Each sheath 292 is fixed or immovably attached at one end to the outer surface 220 of the wall 216 of the central catheter 212 at a point or along a line adjacent to but spaced apart from the attachment 290 for an associated peripheral catheter 214. The length of each sheath 292 is sufficient that the sheath covers the entire length of the distal end portion 234 of an associated peripheral catheter 214. Each sheath 292 is attached at one or more points or on a line along its length to the outer surface 220 of the wall 216 of the central catheter 212 using a releasable adhesive or other detachable attachment mechanism (not shown) to help maintain the distal end portion 234 of the associated peripheral catheter 214 against the wall 216 of the central catheter.

The peripheral catheters 214 do not communicate with the central lumen 222 of the central catheter 212. Instead, the proximal end portion (not shown) of each peripheral catheter 214 is connected to a device (not shown), such as pump, for delivering a fluid, such as a liquid, under pressure to the catheter assembly 200 and thus into a patient's tissue. The fluid contains a bioactive material, such as a pharmaceutical material, and is delivered to the each of the peripheral catheters 214. Such a fluid may flow along the central lumen (not shown) of the peripheral catheter 214 from adjacent its proximal end portion (not shown) into the distal end portion 234 of the peripheral catheter. The distal end of the peripheral catheter 214 is open so that fluid may flow out of the open distal end of the peripheral catheter.

Figure 6:
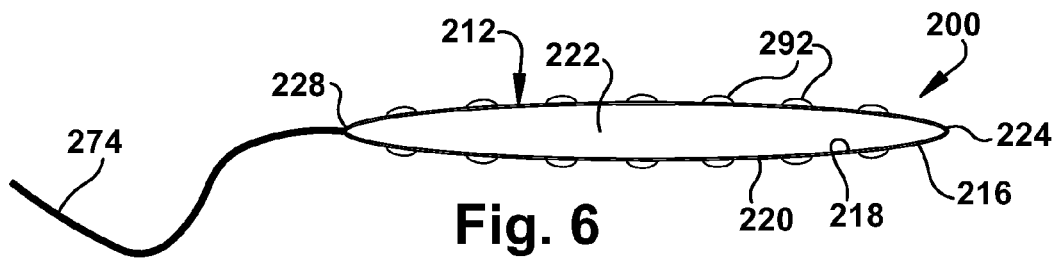
FIG. 6 is a schematic view of a third embodiment of a catheter assembly in accordance with the present invention showing the catheter assembly in a non-extended condition.

In use, the central catheter 212 is introduced into a cavity, such as a resection cavity, in the tissue of a patient. The central catheter 212 is introduced into the tissue cavity in an uninflated or partially inflated or distended condition, as shown in FIG. 6. In this condition, the distal end portions 234 of the peripheral catheters 214 lie against the outer surface 220 of the wall 216 of the central catheter 212 and are covered by their associated sheaths 292, as shown in FIG. 8. When the central catheter 212 is appropriately positioned, fluid is introduced into the central lumen 222 of the central catheter to inflate the central catheter. As the central catheter 212 inflates, the wall 216 of the central catheter resiliently stretches or distends. As the wall 216 of the central catheter 212 resiliently distends or extends, the central catheter fills the cavity in the tissue of the patient and the distal end portions 234 of the peripheral catheters 214 are moved closer to the tissue surrounding and defining the cavity in the tissue.

In addition, as the wall 216 of the central catheter 212 resiliently extends or distends and the central catheter inflates, the distance between the fixed attachment point of each sheath 292 and the attachment 290 for the distal end portion 234 of its associated peripheral catheter 214 increases from a first distance (designated "d1" in FIG. 8) to a second, greater distance (designated "d2" in FIG. 9). The movement of the fixed attachment point of each sheath 292 relative to other points on the outer surface 220 of the wall 216 of the central catheter 212 causes the releasable adhesive or other detachable attachment mechanism (not shown) along the length of the sheath to release or detach from the outer surface 220 of the wall 216. The sheath 292 is thereby allowed to move from a position covering and constraining the distal end portion 234 of its associated peripheral catheter 214. The sheath 292 may be viewed as effectively withdrawn from a position covering and constraining the distal end portion 234 of its associated peripheral catheter 214. Alternatively, the distal end portion 234 of the associated peripheral catheter 214 may be viewed as effectively pulled by its associated attachment 290 away from the sheath 292. Regardless of the point of view, the distal end portions 234 of the peripheral catheters 214 are left free to project away from the outer surface 220 of the wall 216 of the central catheter 212 and assume their outwardly curved, predetermined shape. As the distal end portions 234 of the peripheral catheters 214 assume their outwardly curved, predetermined shape, the peripheral catheters 214 penetrate the patient's tissue and extend into the patient's tissue away from the central catheter 212 in a radial array.

With the central and peripheral catheters 212 and 214 of the catheter assembly 200 appropriately positioned in the patient's tissue, therapeutic treatment of the tissue with a bioactive material can begin. To introduce the bioactive material, the pump or other device (not shown) attached to the proximal ends (not shown) of the peripheral catheters is actuated. A fluid, such as a liquid, containing a bioactive material, such as a pharmaceutical material, is delivered under pressure to the catheter assembly 200 and thus into the patient's tissue. The fluid is delivered into the central lumens (not shown) of the associated peripheral catheters 214. The fluid flows along the central lumens of the peripheral catheters 214 until it reaches the open ends of the distal end portions 234 of the peripheral catheters and is thereby introduced into the patient's tissue. When the patient's treatment is completed, the catheter assembly 200 may be removed by allowing the central catheter 212 to deflate and then withdrawing the catheter assembly from the patient's tissue.

Although the catheter assembly 200 of FIGS. 6-9 is illustrated and described as having its peripheral catheters 214 disposed outward of the outer surface 220 of its central catheter 212, the peripheral catheters could be disposed, in whole or in part, in the wall 216 of the central catheter between the inner and outer surfaces 218 and 220. With such a construction, the wall 216 could, in effect, be a sheath portion of the central catheter and could potentially replace the sheaths 292.

Figure 10:
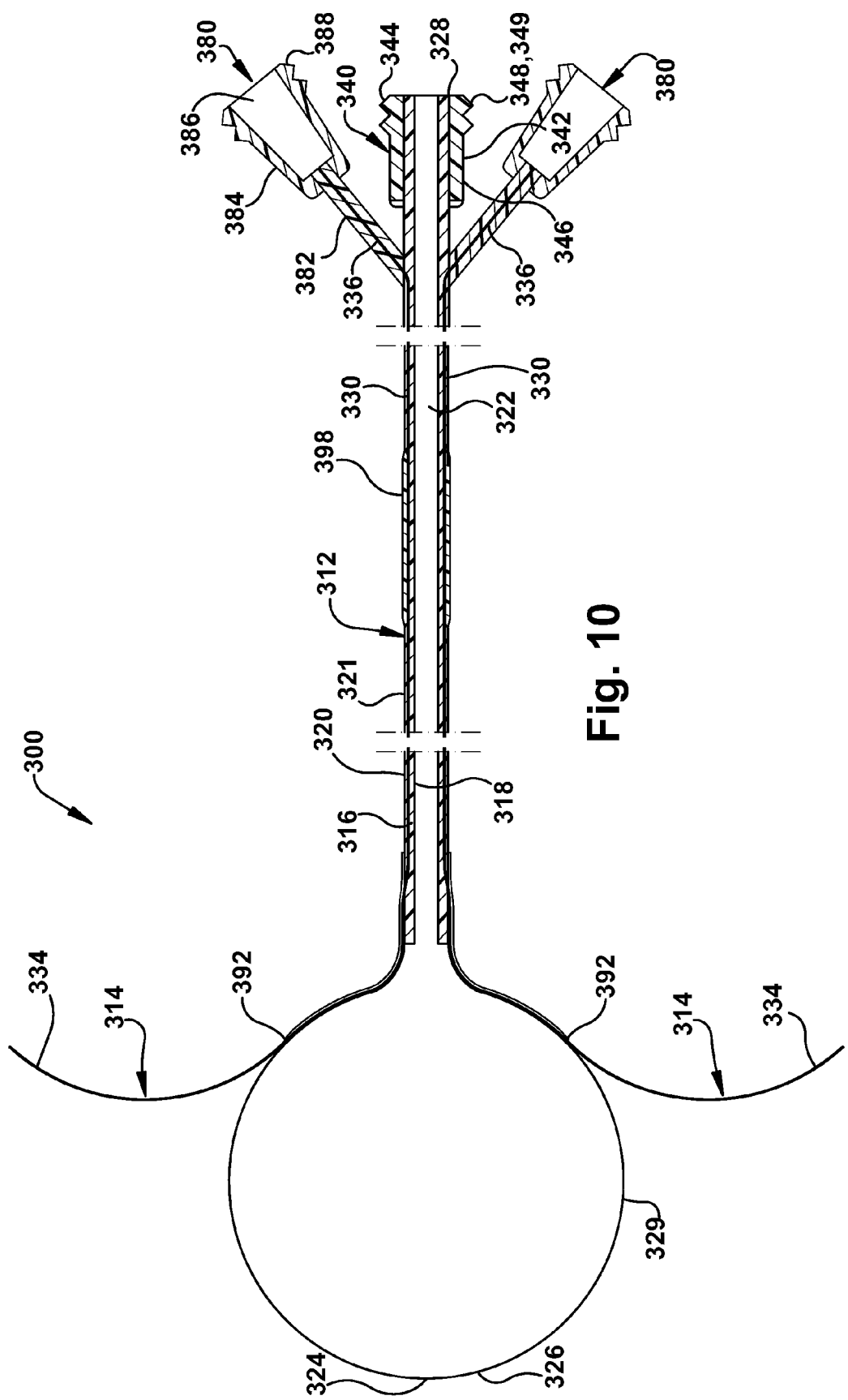
FIG. 10 is a sectional view of a fourth embodiment of a catheter assembly in accordance with the present invention showing the catheter assembly in an extended condition.
Figure 11:
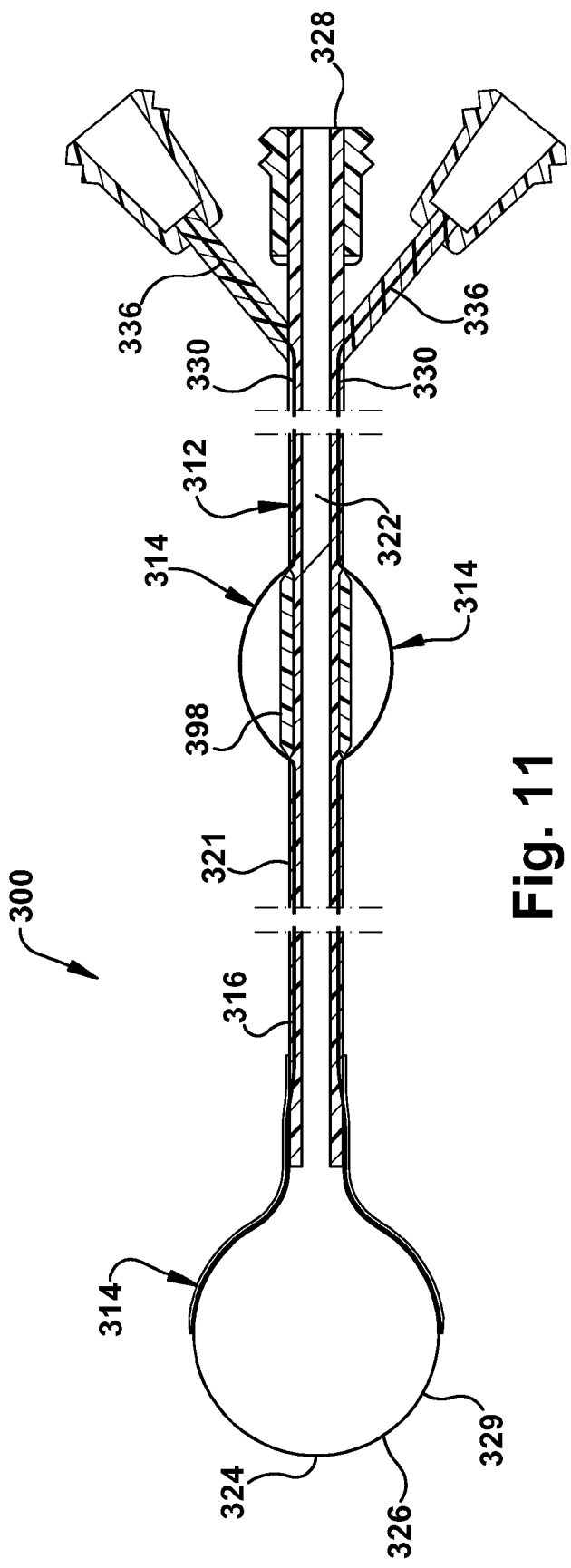
FIG. 11 is a sectional view of the catheter assembly of FIG. 10 in a non-extended condition.
Figure 12:
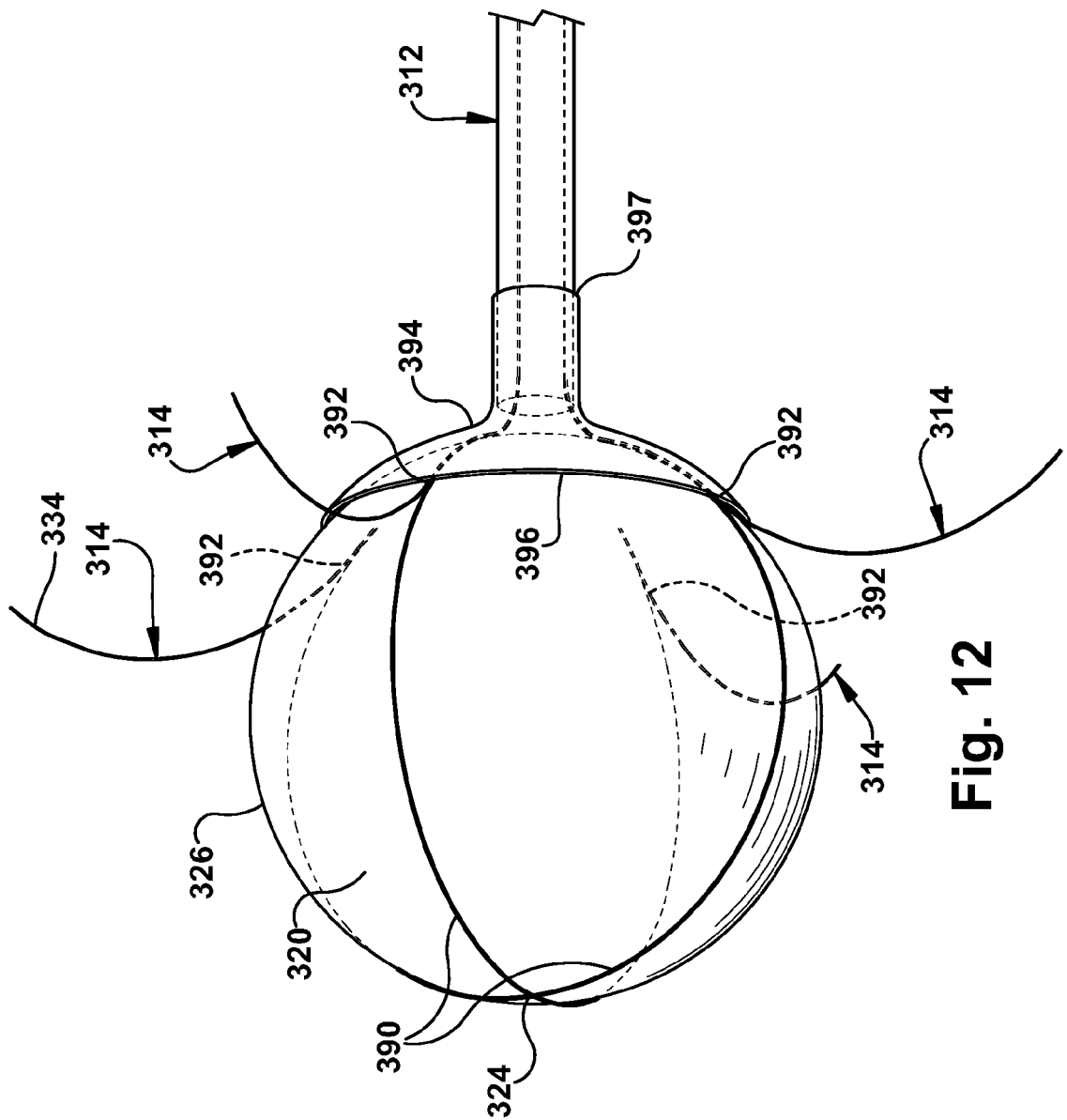
FIG. 12 is a perspective view of a portion of the catheter assembly of FIG. 10.

FIGS. 10 through 12 illustrate a catheter assembly 300 that is constructed in accordance with a fourth example of the present invention. The catheter assembly 300 includes a first or central catheter 312 and second or peripheral catheters 314, two of which are shown in FIGS. 10 and 11. The central catheter 312 is made of a flexible and resilient biocompatible material, such as a medical grade silicone elastomer, and includes a longitudinally extending, tubular wall 316. The tubular wall 316 includes a radially inner surface 318 and a radially outer surface 320. Both the inner surface 318 and the outer surface 320 extend substantially the entire length of the central catheter 312.

The inner surface 318 of the wall 316 defines a central lumen 322 that extends substantially the entire length of the central catheter 312. The central lumen 322 is closed at the distal end 324 of the central catheter 312 by a thinned end portion 326 of the wall 316. The central lumen 322 is open at the opposite, proximal end 328 of the central catheter 312. The thinned end portion 326 of the wall 316 partially defines a balloon portion 329 of the central catheter 312 and the catheter assembly 300. In the thinned end portion 326 of the wall 316, the outer surface 320 of the wall 316 is separated from the inner surface 318 by a smaller distance than in a middle portion 321 of the length of the central catheter 312 and in a portion adjacent the proximal end 328 of the central catheter. As a consequence, the wall 316 has a greater thickness in the middle portion 321 of its length and adjacent its proximal end 328 than adjacent its distal end 324 and in the thinned end portion 326.

The thinned end portion 326 of the wall 316 of the central catheter 312 is formed from a separate piece of flexible and resilient biocompatible material, such as a medical grade silicone elastomer, and is secured to the middle portion 321 of the wall by, for example, a biocompatible adhesive material or radio frequency welding. Alternatively, the thinned end portion 326 may be formed in one piece with the middle portion 321 of the wall 316. The thinned end portion 326 of the wall 316 has a higher modulus of elasticity than the middle portion 321 of the length of the wall and the portion adjacent the proximal end 328 of the wall. As a result of the different moduli of elasticity and the previously described different thicknesses of the thinned end portion 326 and the middle portion 321 of the wall 316, when the central lumen 322 of the central catheter 312 is subjected to increased fluid pressure, such as a pressure greater than ambient atmospheric pressure, the thinned end portion 326 of the wall 316 tends to distend or extend to a greater extent than, for example, the middle portion 321.

As best shown in FIG. 10A, tunnels or passages 330 are formed in the wall 316 of the central catheter 312 and extend generally lengthwise of the central catheter. Two passages 330 are shown in FIGS. 10 and 11 at diametrically opposite positions about the circumference of the wall 316. The wall 316 of the central catheter 312 may include more or fewer such passages 330, as desired. Each of the passages 330 is substantially identical in construction to the other passages 330. Like the passages 130 of the catheter assembly 100 shown in FIGS. 4-5, each of the passages 330 receives an associated peripheral catheter 314. The peripheral catheters 314 are thus disposed in the wall 316 of the central catheter 312, radially outward of the inner surface 318 of the wall 316 and, for a major portion of their lengths, radially inward of the outer surface 320 of the wall 316. This portion of the lengths of the peripheral catheters 314 extends lengthwise substantially parallel to the central catheter 312. As can be seen from FIG. 10A, the outer diameter of each of the peripheral catheters 314 is smaller than the thickness of the middle portion 321 of the length of the wall 316 of the central catheter 312 and smaller than the diameter of the associated passage 330. Each peripheral catheter 314 has a central lumen 332, which is disposed outside of the central lumen 322 of the central catheter 312. Likewise, the central lumen 322 of the central catheter 312 is disposed outside of the central lumens 332 of the peripheral catheters 314. Each peripheral catheter 314 is formed of a biocompatible material, such as PTFE, that has sufficient rigidity to penetrate a patient's tissue and also has sufficient flexibility and resilience to withstand being deflected and then return to a non-deflected position.

As best seen in FIGS. 10 and 10A, a distal end portion 334 of each peripheral catheter 314 can project radially outward of the outer surface 320 of the wall 316 of the central catheter 312 near the distal end 324 of the central catheter. To facilitate such radially outward projection of the peripheral catheter 314, the passage 330 in the wall 316 of the central catheter 312 angles radially outward and opens onto the outer surface 320 of the wall 316. The radially outward curvature of the passage 330 occurs adjacent the junction between the middle portion 321 of the wall 316 and the thinned end portion 326 of the wall. The distal end portion 334 of the peripheral catheter 314 is given a predetermined shape in the form of an outwardly directed curve or hook.

The proximal end portion 336 of each peripheral catheter 314 projects radially outward of the outer surface 320 of the wall 316 of the central catheter 312 near the proximal end 328 of the central catheter. The proximal end portion 336 of each peripheral catheter 314 is associated with a fluid inlet port or injection port assembly 380, which receives the proximal end portion of its associated peripheral catheter.

Each injection port assembly 380 includes a sleeve portion 382 and connector portion 384, such as a Luer lock connector. The sleeve portion 382 and connector portion 384 of each injection port assembly 380 are joined to one another and may be formed in one piece. The sleeve portion 382 of each injection port assembly 380 is elongated and extends between its associated connector portion 384 and an area on the outer surface 320 of the wall 316 of the central catheter 312 from which the proximal end portion 336 of the associated peripheral catheter 314 projects. The sleeve portion 382 surrounds and is bonded to the proximal end portion 336 of the associated peripheral catheter 314 and helps to protect the proximal end portion. The sleeve portion 382 is also adhesively bonded or otherwise secured to the outer surface 320 of the wall 316 of the central catheter 312, thereby fixing the proximal end portion 336 of the associated peripheral catheter 314 to the wall 316 of the central catheter.

The proximal end portion 336 of each peripheral catheter 314 extends into the connector portion 384 of its associated injection port assembly 380. The central lumen 332 of the peripheral catheter 314 communicates with a central lumen 386 in the connector portion 384 of the injection port assembly 380. An outer surface 388 of the connector portion 384 is threaded to facilitate attachment of a second connector (not shown) and tubing (not shown) for delivering a fluid to the connector portion and thus to the peripheral catheter 314. Such a fluid may flow along the central lumen 332 of the peripheral catheter 314 from its proximal end portion 336 into the distal end portion 334 of the peripheral catheter. The distal end of the peripheral catheter 314 is open so that fluid may flow out of the open distal end of the peripheral catheter.

The portion of the central catheter 312 adjacent the proximal end 328 is received in a tubular male connector 340, such as a male Luer lock connector. The male connector 340 has a head portion 342 and an opposite threaded portion 344. The head portion 342 of the male connector 340 has an outer surface 346 formed for manual manipulation to facilitate attachment of another connector (not shown), which, in turn, may be connected to and communicate with a length of tubing (not shown). The tubing delivers a fluid to the central lumen 322 for distending the thinned end portion 326 of the wall 316 of the central catheter 312 and inflating the central catheter. When distended, as shown in FIG. 10, the thinned end portion 326 resembles a balloon and can occupy a space or volume that has a relatively large radial dimension. The central catheter 312 is thus suitable for use in a tissue cavity, such as a resection cavity from which a tumor has been surgically removed.

Distension of the thinned end portion 326 of the wall 316 of the central catheter 312 also deploys the distal end portions 334 of the peripheral catheters 314. More specifically, as best shown in FIG. 12, one or more elongated pieces of material, such as threads, 390 extend across and are secured to the outer surface 320 of the thinned end portion 326 of the wall 316. The threads 390 are formed of a biocompatible material that has a lower modulus of elasticity than the thinned end portion 326 of the wall 316. The threads 390 are thus less extensible than the thinned end portion 326 of the wall 316, but are flexible. The material of which the threads 390 are formed may be any material that is biocompatible and that will produce threads that are less extensible than the thinned end portion 326 of the wall 316, including, for example, plastic, silicone, metal, and fabric. The material of the threads 390 need not be twisted like yarn or plaited or woven. The threads 390 may be elongated bands or strips of material.

Each thread 390 is secured to at least one point on the outer surface 320 of the thinned end portion 326, such as the distal end 324 of the central catheter 312. The thread 390 then extends in a direction away from the distal end 324 of the central catheter 312 toward the middle portion 321 of the wall 316. Near the middle portion 321 of the wall 316 of the central catheter 312 (when the central catheter is in a non-inflated or partially inflated condition, as, shown for example, in FIG. 11), the thread 390 is connected at a junction 392 to at least one peripheral catheter 314, thereby connecting the peripheral catheter 314 to the wall 316 of the central catheter. Each thread 390 may be secured to a single peripheral catheter 314. Alternatively, as shown in FIG. 12, each thread 390 may be secured at a first junction 392 to a first peripheral catheter 314, extend to the distal end 324 of the central catheter 312 along a circumferential path on the outer surface 320 of the thinned end portion, and then extend back to a second junction 392 at which the thread is secured to a second peripheral catheter 314 positioned diametrically opposite the first peripheral catheter.

Because the thread or threads 390 are secured to the thinned end portion 326 of the wall 316 of the central catheter 312, extension or distention of the thinned end portion 326 tends to pull the threads in a direction away from the middle portion 321 of the wall 316. As the threads 390 are pulled away from the middle portion 321 of the wall 316, the junctions 392 between the threads and the peripheral catheters 314, together with the distal end portions 334 of the peripheral catheters, are similarly pulled in a direction away from the middle portion 321 of the wall. The curved or hooked distal end portions 334 of the peripheral catheters 314 are thereby deployed and pulled into the tissue surrounding the inflated or distended thinned end portion 326 of the wall 316. Distension or extension of the thinned end portion 326 of the wall 316 thus causes the distal end portions 334 of the peripheral catheters to be pulled by the threads 390 from a first, non-deployed position or condition to a second, deployed position or condition.

To help determine the area in which the distal end portions 334 of the peripheral catheters 314 enter the surrounding tissue, a cover or sheath 394 is disposed over the outer surface 320 of the thinned end portion 326 of the wall 316. As illustrated in FIG. 12, the sheath 394 is generally semi-spherical in shape with a large diameter open end 396 disposed away from the middle portion 321 of the wall 316 and a small diameter end 397 disposed adjacent to the middle portion of the wall 316. The small diameter end 397 of the sheath 394 is attached to the middle portion 321 of the wall 316 adjacent the junction between the middle portion and the thinned end portion 326 of the wall. The threads 390 and the distal end portions 334 of the peripheral catheters 314 extend between sheath 394 and the outer surface 320 of the thinned end portion 326 of the wall 316 of the central catheter 312. The sheath 394 may have a greater or lesser surface area than shown in FIG. 12 and may, therefore, cover or overlap the thinned end portion 326 to a greater or lesser extent than shown in FIG. 12.

The sheath 394 is formed of a material that has a lower modulus of elasticity than the material of which the thinned end portion 326 is made and tends to constrain the distal end portions 334 of the peripheral catheters 314. As the thinned end portion 326 of the wall 316 is distended, the threads 390 and the distal end portions 334 of the peripheral catheters 314 tend to be pulled from under the sheath 394 and may thus project away from the outer surface 320 of the wall 316 of the central catheter 312 and assume their outwardly curved, predetermined shape. As the distal end portions 334 of the peripheral catheters 314 assume their outwardly curved, predetermined shape, the peripheral catheters 314 penetrate the patient's tissue and extend into the patient's tissue away from the central catheter 312 in a radial array.

In use, the central catheter 312 of the catheter assembly 300 is introduced into a cavity, such as a resection cavity, in the tissue of a patient. The central catheter 312 is introduced into the tissue cavity in an uninflated or partially inflated condition, as shown in FIG. 11, with the thinned end portion 326 of the wall 316 either not distended or partially distended. In this condition, the distal end portions 334 of the peripheral catheters 314 lie against the outer surface 320 of the thinned end portion 326 of the wall 316 of the central catheter 312 and are covered by the sheath 394. When the central catheter 312 is appropriately positioned, fluid is introduced into the central lumen 322 of the central catheter to inflate or further inflate the central catheter and extend or distend the thinned end portion 326 of the wall 316 of the central catheter. As the central catheter 312 inflates, the thinned end portion 326 of the wall 316 of the central catheter resiliently stretches or distends. As the thinned end portion 326 of the wall 216 resiliently distends or extends, the central catheter 312 fills the cavity in the tissue of the patient and the distal end portions 334 of the peripheral catheters 314 are moved closer to the tissue surrounding and defining the cavity in the tissue.

In addition, as the central catheter 312 inflates and the wall 316 of the central catheter resiliently distends or extends, the threads 390 and the distal end portions 334 of the peripheral catheters 314 are pulled from under the sheath 394 so that the distal end portions 334 can project away from the outer surface 320 of the wall 316 and assume their outwardly curved, predetermined shape. As the distal end portions 334 of the peripheral catheters 314 assume their outwardly curved, predetermined shape, the peripheral catheters 314 penetrate the patient's tissue and extend into the patient's tissue away from the central catheter 312 in a radial array.

With the central and peripheral catheters 312 and 314 of the catheter assembly 300 appropriately positioned in the patient's tissue, therapeutic treatment of the tissue with a bioactive material can begin. To introduce the bioactive material, a pump or other device (not shown) connected to the tubing (not shown) attached to the injection port assemblies 380 of the peripheral catheters 314 is actuated. A fluid, such as a liquid, containing a bioactive material, such as a pharmaceutical material, is delivered under pressure to the catheter assembly 300 and thus into the patient's tissue. The fluid is delivered into the central lumens 332 of the associated peripheral catheters 314. The fluid flows along the central lumens 332 of the peripheral catheters 314 until it reaches the open ends of the distal end portions 334 of the peripheral catheters and is thereby introduced into the patient's tissue.

When the patient's treatment is completed, the catheter assembly 300 may be removed by first allowing the central catheter 312 to deflate. To ensure that the peripheral catheters 314 are withdrawn from the patient's tissue and again covered by the sheath 394, resilient devices 398, such as elastic bands or springs, may be secured to the peripheral catheters in the middle portion 321 of the length of the wall 316 closer to the proximal end 328 than to the distal end 324 of the central catheter 312. As shown in FIG. 10, the resilient devices 398 may be stretched and flattened against the middle portion 321 of the wall 316 of the central catheter 312 when the thinned end portion 326 of the central catheter 312 is distended and the peripheral catheters 314 are exposed from beneath the sheath 394 and deployed. As shown in FIG. 11, the resilient devices 398 return to a thicker, less stretched condition and the adjacent portions of their associated peripheral catheters 314 bow outward away from the central catheter 312 when the peripheral catheters are retracted and covered by the sheath 394. To permit such outward bowing of the peripheral catheters 314, the passages 330 in the wall 316 of the central catheter 312 must be at least partially open to the outer surface 320 of the wall 316 adjacent the resilient devices 398. When the peripheral catheters 314 are withdrawn from the patient's tissue, the catheter assembly may be withdrawn from the cavity in the patient's tissue.

Although the peripheral catheters 314 are fixed, via the injection port assemblies 380, to the wall 316 of the central catheter 312, the peripheral catheters could be connected to the wall of the central catheter without being fixed to the wall. In particular, as the distal end portions 334 of the peripheral catheters 314 can be pulled away from the sheath 394 by the threads 390 in response to inflation of the central catheter 312, the proximal end portions 336 of the peripheral catheters 314 could be longitudinally movable relative to the central catheter. In such a catheter assembly, the injection port assemblies would not be fixed to the wall 316 of the central catheter 312, but rather would be movable along a portion of the length of the central catheter. The peripheral catheters 314 would remain connected to the wall 316 of the central catheter 312, however, via the threads 390 and via the radial constraint imposed by the surfaces of the wall 316 defining the passages 330 through which the peripheral catheters extend. In addition, in such a catheter, the resilient devices 398 could be positioned adjacent the proximal end portions 336 of the peripheral catheters 314 so as to pull the peripheral catheters resiliently in a direction along the length of the central catheter 312 without outward bowing as the central catheter deflates and the thinned end portion 326 returns to a non-distended or less distended condition.

As another alternative, the individual threads 390 could be combined into a single member, such a cap having a partially spherical shape. Such a cap would be positioned at and attached to the distal end 324 of the central catheter 312 and would, therefore, be diametrically opposite the sheath 394 when the thinned end portion 326 of the central catheter is distended. The junctions 392 between the peripheral catheters 314 and such a cap could be at the edge of the cap that surrounds its larger diameter open end or at the ends of partial threads extending from the edge of the cap that surrounds its larger diameter open end. As a further alternative, the threads 390 could be relatively short pieces of material.

Figure 13:
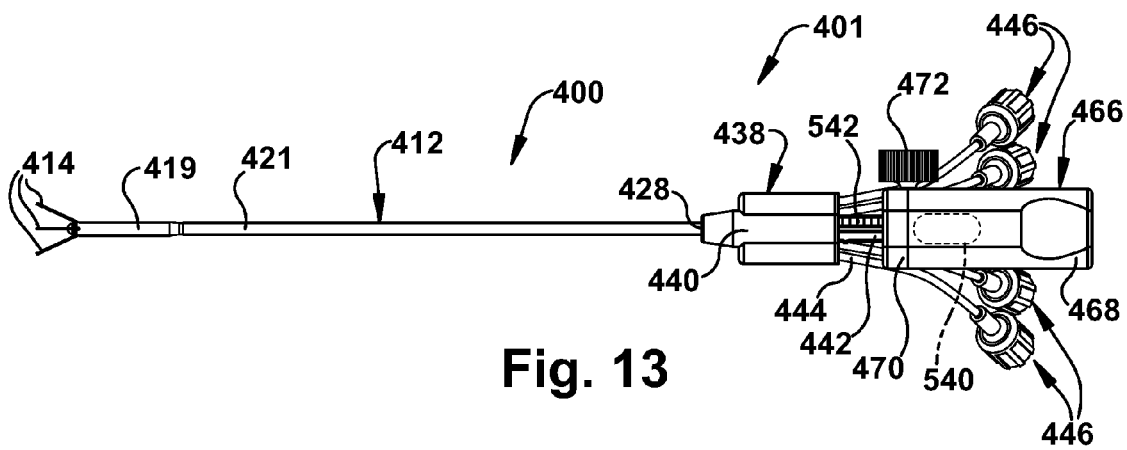
FIG. 13 is a top plan view of a fifth embodiment of a catheter assembly in accordance with the present invention showing the catheter assembly in a non-extended condition.
Figure 14:
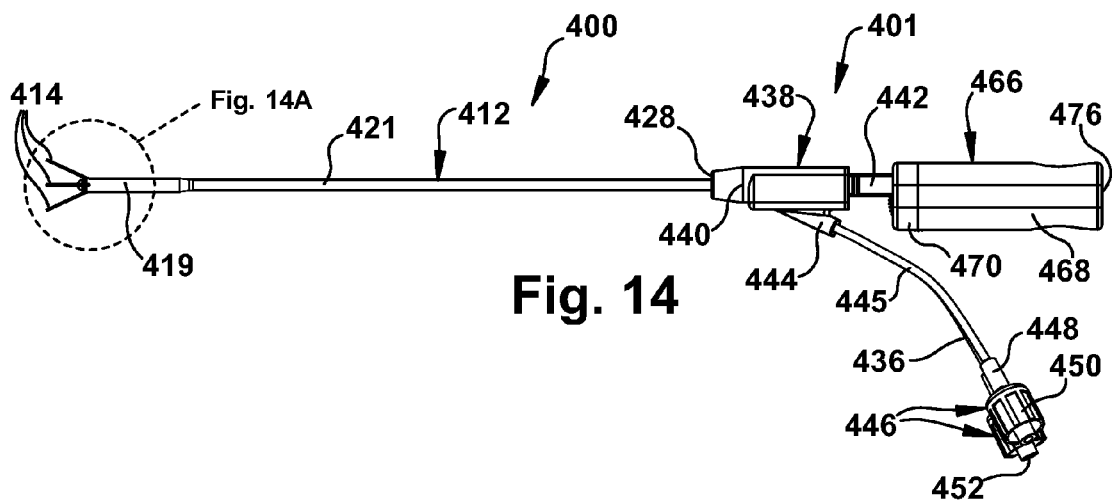
FIG. 14 is a side elevational view of the catheter assembly of FIG. 13.
Figure 14A:
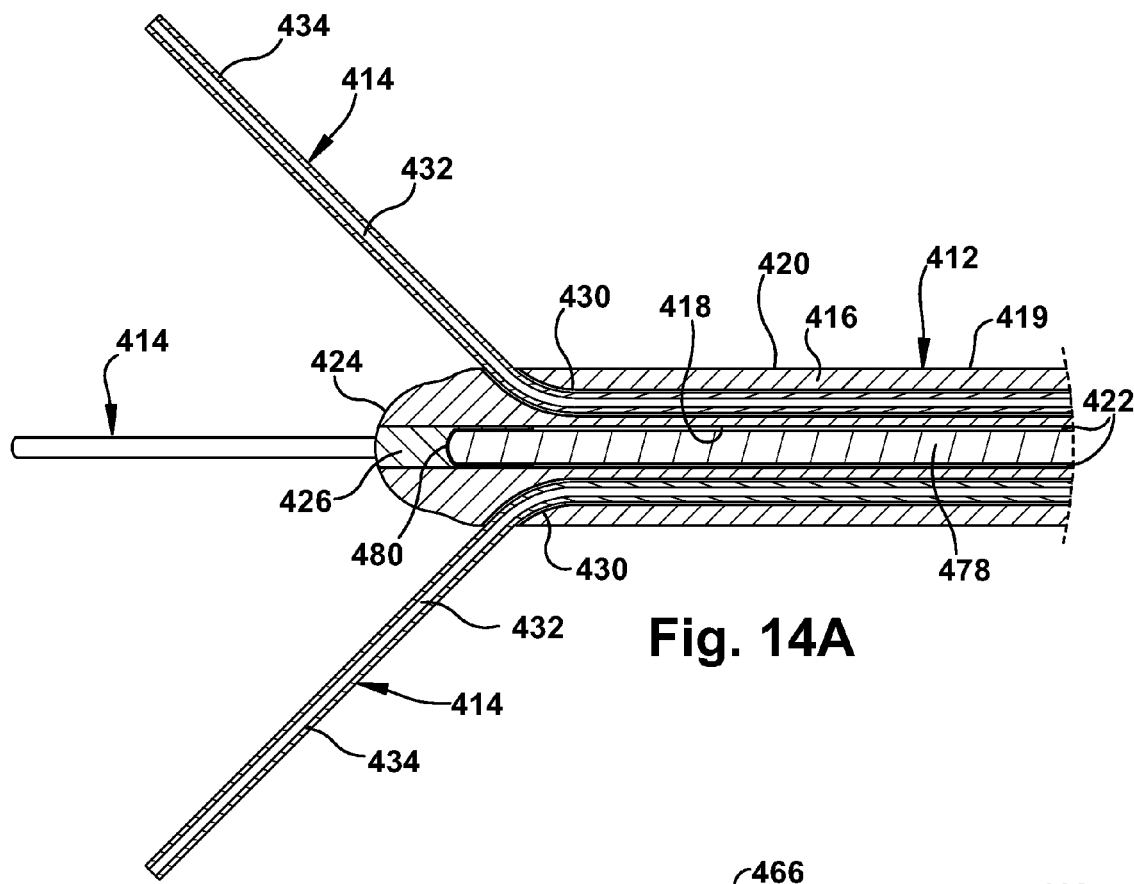
FIG. 14A is an enlarged sectional view of a portion of the catheter assembly of FIG. 14.

FIGS. 13 through 15B illustrate a catheter assembly 400 that is constructed in accordance with a fifth example of the present invention. The catheter assembly 400 includes a first or central catheter 412 and second or peripheral catheters 414, four of which are included in the catheter assembly and three of which are shown in FIGS. 13 and 14. The central catheter 412 is made of a flexible and resilient biocompatible material, such as a medical grade silicone elastomer. As best seen in FIG. 14A, the central catheter 412 includes a longitudinally extending, tubular wall 416. The tubular wall 416 includes a radially inner surface 418 and a radially outer surface 420. Both the inner surface 418 and the outer surface 420 extend substantially the entire length of the central catheter 412.

The outer surface 420 of the wall 416 is separated from the inner surface 418 by a first distance in a first portion 419 of the length of the wall. The first portion 419 of the length of the wall 416 extends from a location adjacent to, but not including, the distal end 424 of the central catheter 412 toward the proximal end 428 of the central catheter. The outer surface 420 of the wall 416 is separated from the inner surface 418 by a second distance, which is smaller than the first distance, in a second portion 421 of the length of the wall 416. The second portion 421 of the length of the wall 416 extends from the first portion 419 to the proximal end 428 of the central catheter 412. As a consequence of the difference between the first and second distances, the wall 416 has a greater thickness in the first portion 419 of its length than in the second portion 421.

The first and second portions 419 and 421 of the length of the wall 416 of the central catheter 412 are formed of elastomeric materials having different properties. The elastomeric material in the first portion 419 of the length of the wall 416 has a relatively low durometer and a relatively low modulus of elasticity and, therefore, is relatively extensible. For example, the elastomeric material of the first portion 419 may have a Shore A hardness of from about 10 to about 20. The elastomeric material in the second portion 421 of the length of the wall 416 has a relatively high durometer and, for an elastomeric material, a relatively high modulus of elasticity and, therefore, is relatively inextensible. For example, the elastomeric material of the second portion 421 may have a Shore A hardness of from about 80 to about 90.

The first and second portions 419 and 421 of the wall 416 may be joined together by initially forming the second portion and then insert molding the first portion onto the second portion. A primer may be applied to the second portion 421 before the insert molding operation to enhance the strength of the joint between the second portion and the first portion 419. To avoid an unnecessary increase in the outer diameter of the catheter assembly 400, overmolding or overlapping of the material of the first portion 419 onto the outer surface 420 of the wall 416 of the second portion 421 may be prevented during the insert molding operation or, alternatively, overmolded or overlapping material may be removed from the outer surface of the second portion after the insert molding operation. As another alternative, the first and second portions 419 and 421 may be separately formed and then joined together end-to-end in a butt joint with a biocompatible adhesive.

The durometer of the first and second portions 419 and 421 can be adjusted using cross-linking agents and fillers. One possible filler is barium sulfate, which would provide radiopacity for the central catheter 412. Optionally, a tether (not shown) formed of a flexible, non-ferrous material may be bonded or otherwise attached at one end to the first portion 419 of the wall 416 of the central catheter 412 and at an opposite end to the second portion 421 of the wall or another portion of the catheter assembly 400. Such a tether (not shown) would help to ensure that the first portion 419 of the wall 416 is not completely disconnected from the remainder of the catheter assembly 400 if the joint between the first portion and the second portion 421 of the wall unexpectedly fails.

The inner surface 418 of the wall 416 defines a central lumen 422 that extends substantially the entire length of the central catheter 412. The central lumen 422 is closed at the distal end 424 of the central catheter 412 by a plug 426 that is formed of a medical-grade elastomeric material and that is secured to the wall 416. The elastomeric material of which the plug 426 is formed has a relatively high durometer and, for an elastomeric material, a relatively high modulus of elasticity and, therefore, is relatively inextensible. For example, a suitable elastomer for the plug 426 may have a Shore A hardness of from about 80 to about 90. Because the plug 426 is relatively inextensible and is secured to the wall 416, the plug restricts or limits the extension or distension of the wall adjacent to the plug, even though the wall adjoining the plug is formed of relatively low durometer and, therefore, relatively extensible elastomeric material. Accordingly, the portion of the wall 416 adjoining or immediately adjacent to the plug 426, including the distal end 424 of the central catheter 412, is formed with an outer diameter equal to or less than the outer diameter of the first portion 419 of the wall, measured when the first portion of the wall is extended or distended as described below.

The plug 426 may be secured to the inner surface 418 of the wall 416 by a biocompatible adhesive (not shown). Alternatively, the plug 426 may be formed of a flowable and curable biocompatible material, such as a liquid silicone elastomer. The flowable and curable material is introduced into the central lumen 422 at the distal end 424 of the central catheter 412 and is cured in place so as to bond to the inner surface 418 of the wall 416. A primer may be applied to the wall 416 before applying the adhesive or before introducing the flowable and curable material so as to enhance the strength of the joint between the plug 426 and the wall. An end surface of the plug 426 presented to the central lumen 422 may be shaped to provide a pocket to receive the end of a stylet 478, as explained in more detail below. Opposite the plug 426, at the proximal end 428 of the central catheter 412, the central lumen 422 is open.

As shown in FIG. 14A, tunnels or passages 430 are formed in the wall 416 of the central catheter 412 and extend generally lengthwise of the central catheter. Two passages 430 are shown in FIG. 14A at diametrically opposite positions about the circumference of the wall 416. The wall 416 of the central catheter 412 may include more or fewer such passages 430, as desired. Each of the passages 430 is substantially identical in construction to the other passages 430. Like the passages 130 of the catheter assembly 100 shown in FIGS. 4-5, each of the passages 430 receives an associated peripheral catheter 414. The peripheral catheters 414 are thus disposed in the wall 416 of the central catheter 412, radially outward of the inner surface 418 of the wall 416 and, for a major portion of their lengths, radially inward of the outer surface 420 of the wall 416. This major portion of the lengths of the peripheral catheters 414 extends lengthwise substantially parallel to the central catheter 412.

Each peripheral catheter 414 has a central lumen 432, which is disposed outside of the central lumen 422 of the central catheter. Likewise, the central lumen 422 of the central catheter 412 is disposed outside of the central lumens 432 of the peripheral catheters 414. Each peripheral catheter 414 is formed of a biocompatible material, such as PTFE, that has sufficient rigidity to penetrate a patient's tissue and also has sufficient flexibility and resilience to withstand being deflected and then return to a non-deflected position.

As can be seen from FIG. 14A, the outer diameter of each of the peripheral catheters 414 is smaller than the thickness of the wall 416 of the central catheter 412 and, at least in the first portion 419 of the length of the wall 416, smaller than the diameter of the associated passage 430. In the second portion 421 of the length of the wall 416, the outer diameter of each of the peripheral catheters 414 may also be smaller than the diameter of the associated passage 430. Alternatively, the outer diameter of each of the peripheral catheters 414 in the second portion 421 of the length of the wall 416 may be approximately the same as or slightly larger than the diameter of the associated passage 430 to provide an interference fit with the wall. Such an interference fit may result in the peripheral catheters 414 making the elastomeric material of the second portion 421 of the wall 416 less extensible (or more inextensible) if the peripheral catheters are made of a material that is less extensible than the elastomeric material of the second portion. A similar effect on the extensibility of the second portion 421 of the length of the wall 416 may be achieved by forming additional passages in just the second portion and inserting lengths of peripheral catheter material or other flexible, relatively inextensible material into the additional passages and bonding the lengths of material to the wall.

As best seen in FIGS. 14 and 14A, a distal end portion 434 of each peripheral catheter 414 can project radially outward of the outer surface 420 of the wall 416 of the central catheter 412 near the distal end 424 of the central catheter. To facilitate such radially outward projection of the peripheral catheter 414, the distal end portion of each passage 430 in the wall 416 of the central catheter 412 curves or angles radially outward, as a departure ramp, and opens onto the outer surface 420 of the wall 416. A short length of tubing, such as PTFE tubing, (not shown) may be positioned in the radially curved or angled portion of the passage 430 and bonded to the wall 416 to act as a bearing surface for sliding movement of the peripheral catheter 414 relative to the wall 416. The distal end portion 434 of the peripheral catheter 414 has a predetermined shape in the form of a substantially straight line oriented at a relatively small angle to the remainder of the peripheral catheter, although other shapes, such as curved or hooked, may be used.

The proximal end 428 of the central catheter 412 and the proximal end portions 436 of the peripheral catheters 414 are connected to a hub 438. The hub 438 is formed of plastic, although it may be formed of other materials. The hub 438 includes a main body portion 440, a drive portion 442 that extends rearwardly or proximally (to the right as viewed in FIGS. 13 and 14) from the main body portion, and four microcatheter sleeve portions 444 that project rearwardly and downwardly (as viewed in FIGS. 14 and 15) from the main body portion. The proximal end 428 of the central catheter 412 is received in the main body portion 440 of the hub 438. The outer surface 420 of the wall 416 of the central catheter 412 is bonded to an adjacent, circumferentially extending inner surface (not shown) of the main body portion 440.

The peripheral catheters 414, which are disposed in the wall 416 of the central catheter, are also received in the main body portion 440 of the hub 438. The peripheral catheters 414 extend beyond the proximal end 428 of the central catheter 412 and into passages (not shown) formed in the main body portion 440 of the hub 438. The passages (not shown) redirect the peripheral catheters 414 from a first orientation in which the peripheral catheters are disposed in an array circumferentially around the central lumen 422 of the central catheter 412 into a second orientation in which the peripheral catheters are arrayed on one side of the central catheter. From the main body portion 440 of the hub 438, the passages (not shown) and the peripheral catheters 414 extend into the microcatheter sleeve portions 444 of the hub with one passage and its associated peripheral catheter being located in each microcatheter sleeve portion. Each peripheral catheter 414 extends out of its associated microcatheter sleeve portion 444 downwardly (as viewed in FIGS. 14 and 15) away from the hub 438. The proximal end portion 436 of each peripheral catheter 414 is associated with a fluid inlet port or injection port assembly 446, which receives the proximal end portion of its associated peripheral catheter. Between the microcatheter sleeve portion 444 and the injection port assembly 446, each peripheral catheter 414 is received inside a length of silicone tubing 445, which helps to protect the peripheral catheter. The length of silicone tubing 445 is attached, by adhesive, for example, to the microcatheter sleeve portion 444 and to the injection port assembly 446 associated with the peripheral catheter 414.

Each injection port assembly 446 includes a sleeve portion 448 and a connector portion 450, such as a Luer lock connector. Although a female Luer lock connector may be used in the connector portion 450, a male Luer lock connector or other atypical connector may alternatively be used to help prevent inadvertent connection of the injection port assembly 446 to commonly used fluid sources not intended for use with the catheter assembly 400. The sleeve portion 448 and connector portion 450 of each injection port assembly 446 are joined to one another and may be formed in one piece. The sleeve portion 448 of each injection port assembly 446 is elongated and extends away from its associated connector portion 450 toward the hub 438. The sleeve portion 448 surrounds and is bonded to the proximal end portion 436 of the associated peripheral catheter 414 and helps to protect the proximal end portion.

The proximal end portion 436 of each peripheral catheter 414 extends into the connector portion 450 of its associated injection port assembly 446. The central lumen 432 of the peripheral catheter 414 communicates with a central lumen 452 in the connector portion 450 of the injection port assembly 446. A surface (not shown) of the connector portion 450 is threaded to facilitate attachment of a second connector (not shown) and tubing (not shown) for delivering a fluid to the connector portion and thus to the peripheral catheter 414. Such a fluid may flow along the central lumen 432 of the peripheral catheter 414 from its proximal end portion 436 into the distal end portion 434 of the peripheral catheter. The distal end of the peripheral catheter 414 is open so that fluid may flow out of the open distal end of the peripheral catheter.

Figure 15:
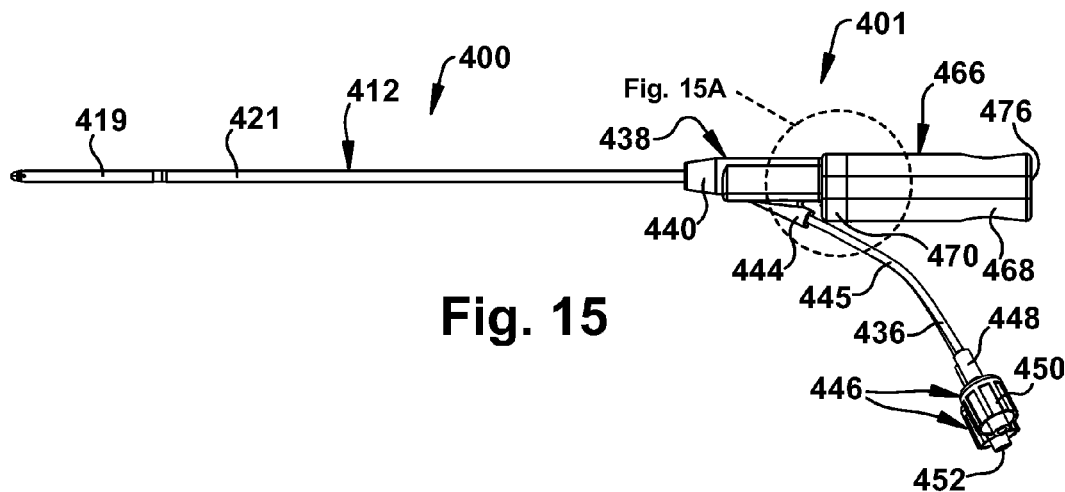
FIG. 15 is a side elevational view of the catheter assembly of FIG. 13 in an extended condition.
Figure 15A:
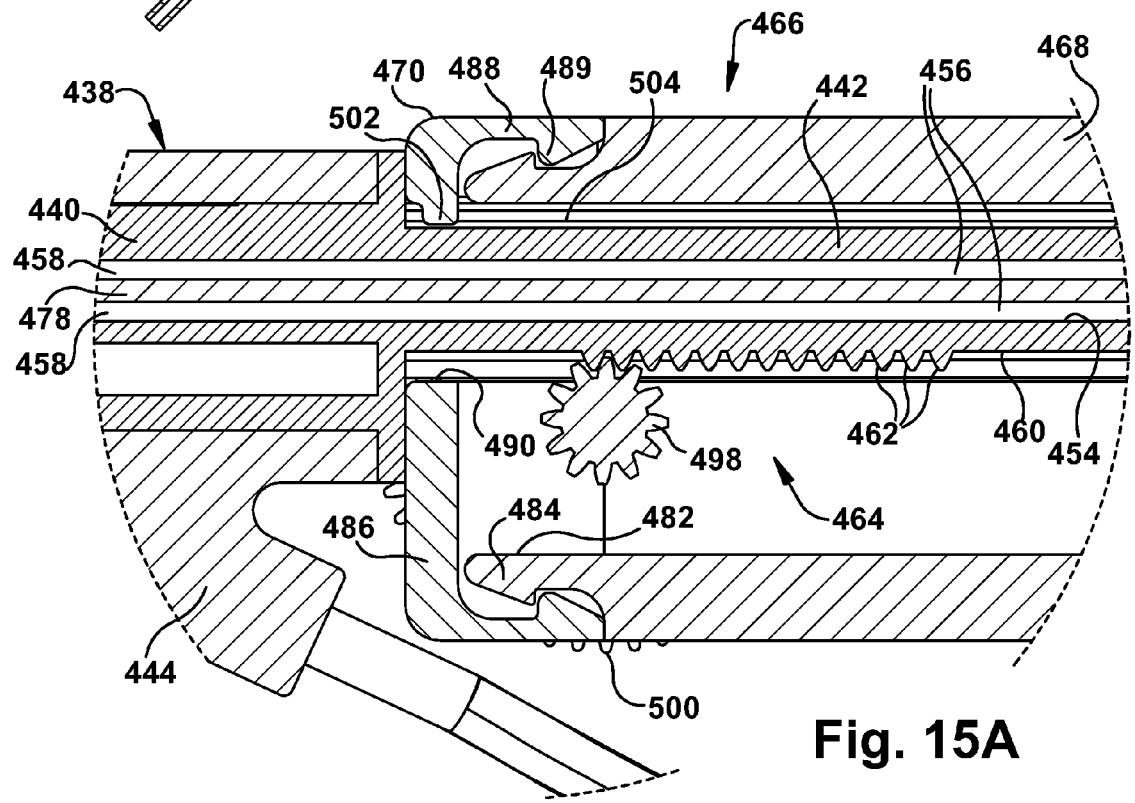
FIG. 15A is an enlarged sectional view of a portion of the catheter assembly of FIG. 15.
Figure 15B:
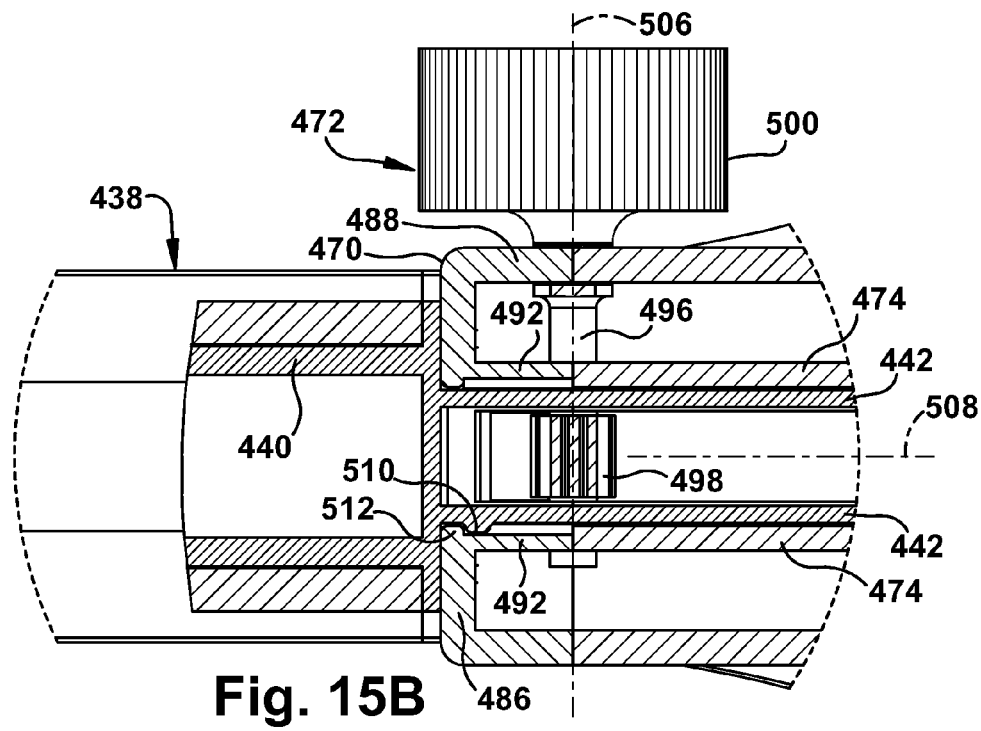
FIG. 15B is a sectional view, in a plane perpendicular to the plane of FIG. 15A, of the portion of the catheter assembly of FIG. 15A.

As shown in FIGS. 15A and 15B, the drive portion 442 of the hub 438 is hollow and has a rectangular cross-section. An inner surface 454 of the drive portion 442 defines a lumen 456, which is coaxial with and an extension of a corresponding lumen 458 in the main body portion 440 of the hub 438. An outer surface 460 of the drive portion 442 is formed with rack teeth 462 that comprise the rack of a rack-and-pinion control mechanism or drive mechanism 464.

The drive portion 442 of the hub 438 is shaped and dimensioned to be received in a stylet handle assembly 466. The stylet handle assembly 466 and the catheter assembly 400 together form a catheter apparatus 401. The stylet handle assembly 466 comprises a housing 468, an end cover 470, and a rotatable drive shaft 472. The housing 468 is hollow and elongated. The housing 468 is also generally rectangular in cross-section with rounded corners to facilitate being grasped by a user of the stylet handle assembly 466. Two spaced apart internal walls 474 extend lengthwise of the housing 468. The proximal end 476 of the housing 468 is closed by an end wall (not shown) in which a small opening (not shown) is formed to receive the stylet 478. The stylet 478 is formed of a metal alloy, such as 35N LT, and has a rounded distal end 480. The 35N LT metal alloy, which is sold by Fort Wayne Metals Research Corp. of Fort Wayne, Ind., provides stiffness and also MRI compatibility as it is both non-magnetic and non-shadowing. When received in the opening (not shown) in the proximal end 476 of the housing 468, the stylet 478 extends lengthwise of the housing between the internal walls 474. The proximal end (not shown) of the stylet 478 is fixed to the housing 468 adjacent its proximal end 476. The distal end 482 of the housing 468 is open and is formed with flexible fingers 484.

The distal end 482 of the housing is closed by the end cover 470, which has a generally cup-like shape. The end cover 470 has an end wall 486 and a peripheral wall 488 that extends perpendicular to the end wall around the outer periphery of the end wall. An opening 490 is formed in the end wall 486 to receive the drive portion 442 of the hub 438. Two spaced apart stub walls 492 extend away from the end wall 486 generally parallel to the peripheral wall 488 and are positioned so that the opening 490 is located between the stub walls. A portion of the peripheral wall 488 is formed with an inwardly projecting lip 489 that is complementary in shape to the fingers 484 on the distal end 482 of the housing 468. The fingers 484 snap into mating engagement with the lip 489 to hold the end cover 470 on the housing 468.

The rotatable drive shaft 472 is captured between the housing 468 and the end cover 470. As best shown in FIG. 15B, the rotatable drive shaft 472 includes a connecting shaft 496. The connecting shaft 496 is captured between the housing 468 and the peripheral wall 488 of the end cover 470. The connecting shaft 496 is also captured between the internal walls 474 of the housing 468 and the stub walls 492 of the end cover 470. Adjacent one end of the connecting shaft 496 is a pinion gear 498. The pinion gear 498 is positioned between the two internal walls 474 of the housing 468 and between the two stub walls 492 of the end cover 470. At the opposite end of the connecting shaft 496 is a knurled knob 500. The knurled knob 500 is disposed outside of the housing 468 to be grasped by a user of the stylet handle assembly 466. The connecting shaft 496, pinion gear 498, and knurled knob 500 are formed in one piece from plastic, but may, alternatively, be formed of different materials and/or as separate components that are subsequently joined together.

When the drive portion 442 of the hub 438 is received in the opening 490 formed in the end cover 470, the drive portion extends between the two stub walls 492 of the end cover and between the two internal walls 474 of the housing 468. A tab 502 formed in the end wall 486 of the end cover 470 and projecting into the opening 490 fits into a complementary groove 504 in the drive portion 442 of the hub 438 to help align the drive portion and the stylet handle assembly. The rack teeth 462 formed on the outer surface 460 of the drive portion 442 engage the pinion gear 498 of the rotatable drive shaft 472. Together, the pinion gear 498 and the rack teeth 462 form the rack-and-pinion control mechanism or drive mechanism 464.

Knurled knob 500 of the rotatable drive shaft 472, as can be seen in FIG. 15B, is rotatable about an axis 506 that is oriented generally perpendicular to the longitudinal axis 508 of the stylet handle assembly 466. Rotation of the knurled knob 500 by a user of the stylet handle assembly 466 produces rotation of the pinion gear 498 and resulting lengthwise movement of the drive portion 442 of the hub 438. This lengthwise movement of the drive portion 442 of the hub 438 is movement relative to the stylet handle assembly 466 and relative to the stylet 478, which is fixed to the housing 468 of the stylet handle assembly. The longitudinal or axial extent of the rack teeth 462 (e.g., the number of rack teeth and their spacing) on the drive portion 442 of the hub 438 can be selected to cause a desired amount of relative movement between the hub 438 and the stylet handle assembly 466. As explained below, a desired amount of relative movement between the hub 438 and the stylet handle assembly 466 produces a desired amount of extension of the first portion 419 of the length of the wall 416, a desired amount of reduction in the outer diameter of the first portion of the wall, and a desired amount of lengthwise deployment of the peripheral catheters 414. The rack-and-pinion control mechanism or drive mechanism 464 is thus operable to produce controlled, relative movement between the hub 438 and the stylet 478 and controlled deployment of the peripheral catheters 414.

As can be seen in FIGS. 14 and 15, the second orientation of the peripheral catheters 414, in which the peripheral catheters and their associated injection port assemblies 446 are all arrayed on one side of the central catheter 412, as directed by the passages (not shown) in the main body portion 440 of the hub 438, helps a user of the stylet handle assembly 466 to grasp and manipulate the stylet handle assembly. More particularly, having the peripheral catheters 414 and their associated injection port assemblies 446 on one side of the central catheter 412 and, therefore, on one side of the stylet handle assembly 466 permits a user of the stylet handle assembly to approach from other sides of the stylet handle assembly without having to maneuver around the peripheral catheters and injection port assemblies. Nonetheless, if desired, the peripheral catheters 414 could be maintained in their first orientation disposed in an array circumferentially around the central lumen 422 of the central catheter 412 as they are directed through the main body portion 440 and the microcatheter sleeve portions 444 of the hub 438.

When the catheter assembly 400 is to be inserted into tissue, such as cerebral tissue, of a patient, stylet 478 is received in and engaged with the stylet handle assembly 466. Specifically, the proximal end (not shown) of the stylet 478 is inserted into the opening 490 in the end cover 470 of the stylet handle assembly 466 and fixed in the opening (not shown) in the proximal end 476 of the housing 468 of the stylet handle assembly. The distal end 480 of the stylet 478 is inserted into and pushed lengthwise through the lumen 456 formed in the drive portion 442 of the hub 438. The distal end 480 of the stylet 478 is then inserted into and pushed lengthwise through the lumen 458 formed in the main body portion 440 of the hub 438 and into the central lumen 422 of the central catheter 412. As the distal end 480 of the stylet 478 approaches the distal end 424 of the central catheter, the drive portion 442 of the hub 438 of the catheter assembly 400 enters the stylet handle assembly 466 through the opening 490 in the end cover 470. The drive portion 442 passes between the internal walls 474 of the housing 468, and the rack teeth 462 on the drive portion engage the pinion gear 498 of the rotatable drive shaft 472 in the stylet handle assembly 466.

At this point, the rounded distal end 480 of the stylet 478 is in contact with the plug 426 at the distal end 424 of the central catheter 412. In particular, the rounded distal end 480 of the stylet 478 is received in the rounded pocket formed in the surface of the plug 426 presented to the central lumen 422 of the central catheter 412 such that the rounded distal end 480 and the rounded pocket help to center the stylet in the central lumen. Although the distal end 480 of the stylet 478 is shown as being rounded, the distal end could have a different shape, and the pocket formed in the surface of the plug 426 presented to the central lumen 422 of the central catheter 412 could also have a different, but complementary shape to help center the stylet in the central lumen. The first portion 419 of the length of the wall 416 is not yet extended, and the distal end portions 434 of the peripheral catheters 414 project from the first portion of the length of the wall, as shown in FIGS. 13 and 14.

After the rounded distal end 480 of the stylet 478 contacts the plug 426 at the distal end 424 of the central catheter 412, the user of the stylet handle assembly 466 grasps the stylet handle assembly and rotates the knurled knob 500. Rotation of the knurled knob 500 causes the pinion gear 498 to engage successive rack teeth 462 on the drive portion 442 of the hub 438 and to draw the drive portion further into the stylet handle assembly 466. As the drive portion 442 is drawn further into the stylet handle assembly 466, the entire catheter assembly 400 is drawn toward the stylet handle assembly, and the stylet 478 is pressed against the plug 426 at the distal end 424 of the central catheter 412. Pressing the stylet 478 against the plug 426 causes the first portion 419 of the length of the wall 416 to extend or distend axially or lengthwise into a longitudinally extended condition.

The extension or stretching of the wall 416 occurs primarily in the thickened first portion 419 of the wall because the plug 426 is made of relatively inextensible material and is bonded to the inner surface 418 of the wall in the first portion and thereby effectively transfers the force applied by the stylet 478 to the wall in the first portion of its length. In addition, the first portion 419 of the length of the wall 416 is made of lower durometer and relatively more extensible material than the second portion 421 of the wall and thereby tends to extend or stretch in preference to the second portion of the length of the wall.

Extension or stretching of the first portion 419 of the length of the wall 416 causes the outer diameter of the wall to decrease or be reduced. This can be seen in FIGS. 14 and 15 by comparing the outer diameter of the first portion 419 in FIG. 14 with the outer diameter of the first portion in FIG. 15 and also by comparing the relative outer diameters of the first and second portions 419 and 421 in FIG. 14 with the relative outer diameters of the first and second portions in FIG. 15. The outer diameter of the first portion 419 of the wall 416 may be reduced to any desired extent, such as less than or equal to the outer diameter of the second portion 421 of the wall. Extension or stretching of the first portion 419 of the length of the wall 416 of the central catheter 412 also causes the first portion of the wall to be drawn over the distal end portions 434 of the peripheral catheters 414 or, in effect, causes the distal end portions of the peripheral catheters to be withdrawn into the passages 430 in the wall 416, as shown in FIG. 15. This result occurs because the peripheral catheters 414 are adhesively bonded to the surface of the wall 416 that defines the passage 430 adjacent the proximal end 428 of the central catheter or otherwise fixed against movement relative to the hub 438.

The durometers and thicknesses of the elastomeric materials used in the first and second portions 419 and 421 of the length of the wall 416 can be selected or tuned to provide a desired amount of reduction in the outer diameter of the first portion of the wall without excessive longitudinal extension of the first portion or use of excessive force. The durometers and thicknesses of the elastomeric materials used in the first and second portions 419 and 421 of the length of the wall 416 can also be selected or tuned to provide a desired extent to which the first portion of the wall is drawn over the distal end portions 434 of the peripheral catheters 414 without excessive longitudinal extension of the first portion. For example, if the distal end portions 434 of the peripheral catheters 414, when deployed, extend about 1 cm from the outer surface 420 of the wall 416 of the central catheter, the longitudinal extension of the first portion 419 of the length of the wall 416 should also be about 1 cm to cover the distal end portions of the peripheral catheters completely without excess extension of the wall beyond the extension necessary to cover the distal end portions of the peripheral catheters. Such an extension of the first portion 419 of the wall 416 should also produce a corresponding reduction in the outer diameter of the first portion of the wall so that the outer diameter of the first portion is equal to or less than the outer diameter of the second portion 421 of the length of the wall. By way of example, in an embodiment in which the first portion 419 of the wall 416 has a length of 2.30 cm, an outer diameter of 3.00 mm, and a central lumen having a diameter of 0.79 mm, the outer diameter of the first portion can be reduced by about 0.50 mm by extending the sample lengthwise to about 1.50 times (150% of) its non-extended length.

As they are being covered by the wall 416 of the first portion 419 of the length of the central catheter 412 or, in effect, withdrawn into the passages 430, the distal end portions 434 of the peripheral catheters 414 are deflected from their outwardly directed, predetermined shape and are constrained in a generally straight configuration by the wall of the central catheter. When the peripheral catheters 414 have been fully withdrawn or retracted into the wall 416 of the central catheter 412, the outer surface 420 of the wall 416 of the central catheter appears essentially smooth and uninterrupted. The wall 416 of the central catheter 412 thus functions as a sheath portion of the central catheter and covers the distal end portions 434 of the peripheral catheters 414.

When the stylet 478 reaches the end of its stroke, as determined by the pinion gear 498 engaging the last tooth 462 on the drive portion 442 of the hub 438 and/or by contact between the main body portion 440 of the hub 438 and the end cover 470 of the stylet handle assembly 466, as shown in FIG. 15, the stylet may be secured in place to facilitate coordinated manipulation of the stylet and the catheter assembly 400. As shown in FIG. 15B, the stylet 478 may be secured in place by locking the stylet handle assembly 466, to which the stylet is secured, to the hub 438 to which the central catheter 412 is secured. Specifically, a projecting detent feature 510 is formed on the drive portion 442 of the hub 438 adjacent the main body portion 440 of the hub, and a complementary projecting detent feature 512 is formed on the end wall 486 of the end cover 470 of the stylet handle assembly 466 adjacent the opening 490 in the end cover. The detent features 510 and 512 engage one another to secure the catheter assembly 400 to the stylet handle assembly 466.

The detent features 510 and 512 may engage with an audible click or a haptically perceptible motion to indicate to the user of the stylet handle assembly 466 that the stylet 478 has come to the end of its stroke. Similarly, the detent features 510 and 512 may disengage with an audible click or a haptically perceptible motion to indicate to the user of the stylet handle assembly 466 that relative movement between the stylet 478 and the catheter assembly 400 has begun. The surfaces of the detent features 510 and 512 that initially engage one another as the catheter assembly 400 is drawn toward the stylet handle assembly 466 may also be formed as inclined ramps to facilitate movement of the detent features past each other into a locking position. Interengagement of the detent features 510 and 512 can help prevent inadvertent relative longitudinal movement between the stylet handle assembly 466 and the catheter assembly 400.

When the stylet handle assembly 466 is secured to the hub 438, the stylet 478 and the catheter assembly 400 tend to move more consistently as a single unit and can be manipulated more easily and accurately. In particular, the stylet 478 can then be used to insert the extended central catheter 412 and the peripheral catheters 414 into the tissue of a patient. Because the outer diameter of the first portion 419 of the wall 416 of the central catheter 412 has been reduced due to the lengthwise extension or distension of the first portion, the opening formed in the patient's tissue is smaller than it would be otherwise. Because the distal end portions 434 of the peripheral catheters 414 have been withdrawn into the wall 416 of the central catheter, the peripheral catheters do not interfere with the insertion of the central catheter into the patient's tissue.

When the distal end 424 of the central catheter 412 is appropriately positioned in a patient's tissue, the stylet handle assembly 466 is held so as to maintain the distal end of the central catheter in position. The knurled knob 500 of the rotatable drive shaft 472 can then be rotated in a direction to disengage the detent features 510 and 512 and to cause relative movement between (a) the catheter assembly 400 and (b) the stylet handle assembly 466 and the stylet 478. In particular, the hub 438 of the catheter assembly 400 is moved in a direction away from the stylet handle assembly 466. As the hub 438 is moved away from the stylet handle assembly 466, the resilience of the extended first portion 419 of the wall 416 of the central catheter 412 pulls the proximal end 428 of the central catheter toward the distal end 424 of the central catheter. The central catheter 412 thus returns resiliently to its initial, non-extended length, as shown in FIGS. 13 and 14.

When the central catheter 412 resiliently returns to its initial, non-extended length and the wall 416 of the central catheter likewise resiliently returns from its longitudinally extended condition to its initial, non-extended length, the distal end portions 434 of the peripheral catheters 414 are no longer withdrawn into the wall 416. The distal end portions 434 of the peripheral catheters 414 instead project from the outer surface 420 of the wall 416 of the central catheter and assume their outwardly directed, predetermined shape. As the distal end portions 434 of the peripheral catheters 414 assume their outwardly directed, predetermined shape, the peripheral catheters 414 penetrate the patient's tissue and extend into the patient's tissue away from the central catheter 412 in a radial array. In addition, as the wall 416 of the central catheter 412 resiliently returns to its initial length, the outer diameter of the wall, particularly the first portion 419, increases from its reduced condition back to its original dimension. The increase in the outer diameter of the wall 416 of the central catheter 412 causes the outer surface 420 of the first portion 419 of the wall 416 to press tightly against adjacent surfaces of the patient's tissue. The resulting close fit between the outer surface 420 of the wall 416 and the adjacent surfaces of the patient's tissue helps to prevent fluid introduced into the tissue by the peripheral catheters 414 from flowing back along the outer surface of the wall toward the proximal end 428 of the central catheter 412.

With the central and peripheral catheters 412 and 414 of the catheter assembly 400 appropriately positioned in the patient's tissue, therapeutic treatment of the tissue with a bioactive material can begin. To introduce the bioactive material, the threaded surface (not shown) of the connector portion 450 of each injection port assembly 446 is connected with a connector (not shown) and the distal end of a length of tubing (not shown). A proximal end (not shown) of the tubing is attached to a device (not shown), such as a pump, for delivering a fluid, such as a liquid. The fluid contains a bioactive material, such as a pharmaceutical material, and is delivered from the tubing into the central lumen 452 of the connector portion 450 of the injection port assembly 446 and then into the central lumen 432 of the associated peripheral catheter 414. The fluid flows along the central lumen 432 of the peripheral catheter 414 until it reaches the open end of the distal end portion 434 of the peripheral catheter and is thereby introduced into the patient's tissue.

If the patient's treatment is continued over an extended period of time and the catheter assembly 400 is therefore left implanted in the patient's tissue for an extended period of time, the stylet handle assembly 466 may be disengaged from the hub 438 of the catheter assembly, and the stylet may thereby be withdrawn entirely from the catheter assembly. Disengagement of the stylet handle assembly 466 and withdrawal of the stylet 478 from the catheter assembly 400 will leave open the proximal end of the lumen 456 in the drive portion 442 of the hub 438. Because the lumen 456 communicates, via the lumen 458 in the main body portion 440 of the hub 438, with the central lumen 422 of the central catheter 412, a cover (not shown) may be placed over the proximal end of the drive portion 442 to keep foreign materials from entering the proximal end 428 of the central lumen in the central catheter. Such a cover (not shown) may also extend over the rack teeth 462 on the outer surface 460 of the drive portion 442 to help protect the rack teeth against damage.

When the patient's treatment is completed, the catheter assembly 400 may be removed by reintroducing the stylet 478 into the catheter assembly to extend or distend the central catheter 412. If the stylet handle assembly 466 has been disengaged from the catheter assembly 400, the stylet is reinserted into the lumen 456 in the drive portion 442 of the hub 438. As the stylet 478 is moved into and through the central lumen 422 of the central catheter 412, the drive portion 442 of the hub 438 of the catheter assembly 400 enters the stylet handle assembly 466 through the opening 490 in the end cover 470. When the rack teeth 462 on the drive portion 442 engage the pinion gear 498 of the rotatable drive shaft 472 in the stylet handle assembly 466, the knurled knob 500 can be rotated to draw the hub 438 of the catheter assembly 400 closer to the stylet handle assembly 466 and to press the rounded distal end 480 of the catheter against the plug 426 at the distal end 424 of the central catheter 412.

Pressing the stylet 478 against the plug 426 as the hub 438 of the catheter assembly 400 is drawn closer to the stylet handle assembly 466 causes the first portion 419 of the length of the wall 416 to extend or distend axially or lengthwise into a longitudinally extended condition and effectively causes the distal end portions 434 of the peripheral catheters 414 to be withdrawn into the passages 430 in the wall 416. When the peripheral catheters 414 have been fully withdrawn or retracted into the wall 416 of the central catheter 412, the stylet handle assembly 466 can be moved away from the patient, thereby withdrawing the catheter assembly 400 from the patient's tissue.

Figure 16:
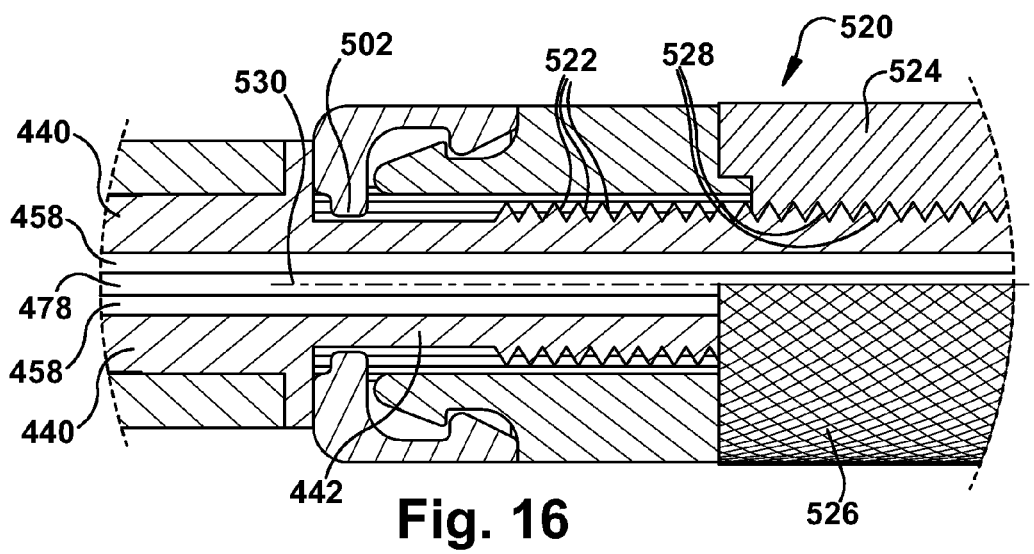
FIG. 16 is sectional view, similar to FIG. 15A, of an alternate construction of the portion of the catheter assembly of FIG. 15.

While the stylet handle assembly 466 of FIGS. 13-15 incorporates a pinion gear 498 to engage rack teeth 462 formed on the drive portion 442 of the hub 438 of the catheter assembly 400, thereby forming a rack-and-pinion drive mechanism 464, other mechanisms may be employed for controlled deployment of the peripheral catheters 414. For example, FIG. 16 illustrates an alternative lead screw control mechanism or drive mechanism 520 that may be substituted for the rack-and-pinion drive mechanism 464 of FIGS. 13-15. To employ the lead screw drive mechanism 520, the drive portion 442 of the hub 438 no longer includes rack teeth 462 but rather includes a lead screw defined by a screw thread 522 that encircles a cylindrical outer surface of the drive portion. Similarly, the pinion gear 498 of the rotatable drive shaft 472 of the stylet handle assembly 466 is replaced with a threaded nut 524 that encircles the drive portion 442.

The threaded nut 524 has a knurled outer surface 526 that can be grasped by a user of the stylet handle assembly 466 and a threaded inner surface 528 that engages and rides on the screw thread 522 of the drive portion 442 of the hub 438. The threaded nut 524 is thus rotated about an axis 530 that is parallel to or coaxial with the longitudinal axis 508 of the stylet handle assembly, whereas the knurled knob 500 of the rotatable drive mechanism is rotated about an axis 506 that is oriented generally perpendicular to the longitudinal axis 508 of the stylet handle assembly 466. Rotation of the threaded nut 524 causes the drive portion 442 of the hub 438 to move longitudinally without rotating. As with the longitudinal extent of the rack teeth 462, the axial or longitudinal extent of the screw thread 522 can be selected to cause a desired amount of extension of the first portion 419 of the length of the wall 416 and a desired amount of lengthwise deployment of the peripheral catheters 414. The lead screw control mechanism or drive mechanism 520 is thus operable to produce controlled, relative movement between the hub 438 and the stylet 478 and controlled deployment of the peripheral catheters 414.

Although the hub 438 of the catheter assembly 400 shown in FIG. 16 includes the screw thread 522 forming the lead screw of the lead screw drive mechanism 520 and the stylet handle assembly 466 includes the threaded nut 524 of the lead screw drive mechanism, the catheter assembly could alternatively include the nut and the stylet handle assembly could include the screw thread defining the lead screw. Likewise, while the hub 438 of the catheter assembly 400 shown in FIGS. 13-15 includes the rack teeth 462 forming the rack of the rack-and-pinion drive mechanism 464 and the stylet handle assembly includes the pinion gear 498, the catheter assembly could alternatively include the pinion gear and the stylet handle assembly could include the rack teeth.

The stylet handle assembly 466 may optionally include a window or transparent portion 540, as shown in phantom in FIG. 13, to allow a user of the stylet handle assembly to see the movement of the drive portion 442 of the hub 438 relative to the stylet handle assembly. Use of such a window 540 may be enhanced by having hash marks or other indicia 542 on an upper surface of the drive portion 442 of the hub 438 to indicate more precisely the extent of the relative movement.

Figure 17:
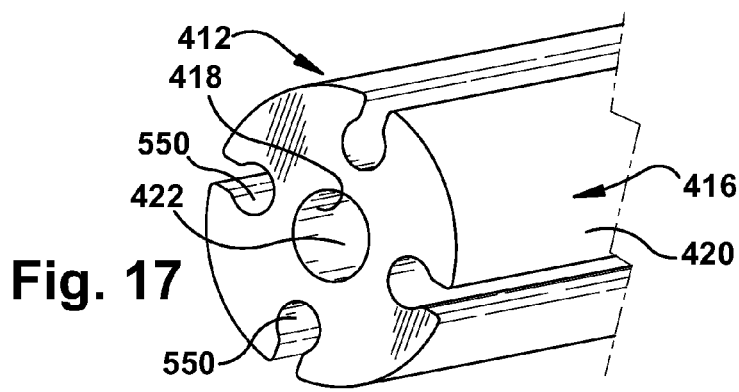
FIG. 17 is a perspective view of an alternative construction of a portion of the catheter assembly of FIGS. 13 to 15.

FIG. 17 illustrates an alternative configuration for the wall 416 of the central catheter 412 and, more particularly, for the second portion 421 of the length of the wall. As shown, the outer surface 420 of the wall 416 is formed with troughs or grooves 550 that extend lengthwise of the central catheter 412. The grooves 550 are configured and dimensioned to receive the peripheral catheters 414. Use of such grooves 550 can facilitate assembly of the peripheral catheters 414 in the less extensible, higher durometer second portion 421 of the length of the wall 416 as the peripheral catheters may be pressed into place radially from a position adjacent and parallel to the central catheter 412.

In addition, use of the grooves 550 can permit the diameter of the central lumen 422 of the central catheter 412 to be increased as compared to the diameter of the central lumen in the central catheter when the peripheral catheters 414 are disposed in the wall 416 of the central catheter. Specifically, for certain elastomeric materials, such as medical grade silicone elastomer, a minimum wall thickness should be provided to ensure structural integrity of the wall. If, for example, a peripheral catheter 414 is disposed in the wall 416 of a central catheter 412 formed of medical grade silicone elastomer, the minimum wall thickness should be provided both radially inward and radially outward of the peripheral catheter. If, on the other hand, the peripheral catheter 414 is disposed in a groove 550 in the radially outer surface 420 of the wall 416, the minimum wall thickness need only be provided between the bottom of the groove and the radially inner surface 418 of the wall. As a result, for any given outer diameter of a central catheter 412, the diameter of the central lumen 422 can be larger than if the peripheral catheter 414 were incorporated in the wall 416. A larger diameter for the central catheter 422 can permit the use of a larger diameter stylet and/or provide a greater clearance between the outer surface of the stylet and the radially inner surface 418 of the wall 416 of the central catheter.

FIGS. 18 and 19 illustrate a catheter assembly 600 that is constructed in accordance with a sixth example of the present invention. The catheter assembly 600 includes a first or central catheter 612 and second or peripheral catheters 614, four of which are included in the catheter assembly. The central catheter 612 is made of a flexible and resilient biocompatible material, such as a medical grade silicone elastomer. As best seen in FIG. 19, the central catheter 612 includes a longitudinally extending, tubular wall 616. The tubular wall 616 includes a radially inner surface 618 and a radially outer surface 620. Both the inner surface 618 and the outer surface 620 extend substantially the entire length of the central catheter 612.

The outer surface 620 of the wall 616 is separated from the inner surface 618 by a first distance in a first portion 619 of the length of the wall. The first portion 619 of the length of the wall 616 extends from a location adjacent to, but not including, the distal end 624 of the central catheter 612 toward the proximal end 628 of the central catheter. The outer surface 620 of the wall 616 is separated from the inner surface 618 by a second distance, which is smaller than the first distance, in a second portion 621 of the length of the wall 616. The second portion 621 of the length of the wall 616 extends from the first portion 619 to the proximal end 628 of the central catheter 612. As a consequence of the difference between the first and second distances, the wall 616 has a greater thickness in the first portion 619 of its length than in the second portion 621.

The first and second portions 619 and 621 of the length of the wall 616 of the central catheter 612 are formed of elastomeric materials having different properties. The elastomeric material in the first portion 619 of the length of the wall 616 has a relatively low durometer and a relatively low modulus of elasticity and, therefore, is relatively extensible. For example, the elastomeric material of the first portion 619 may have a Shore A hardness of from about 10 to about 50, preferably from about 20 to about 40. The elastomeric material in the second portion 621 of the length of the wall 616 has a relatively high durometer and, for an elastomeric material, a relatively high modulus of elasticity and, therefore, is relatively inextensible. For example, the elastomeric material of the second portion 621 may have a Shore A hardness of from about 80 to about 90.

The first and second portions 619 and 621 of the wall 616 may be joined together by initially forming the second portion and then insert molding the first portion onto the second portion. A primer may be applied to the second portion 621 before the insert molding operation to enhance the strength of the joint between the second portion and the first portion 619. To avoid an unnecessary increase in the outer diameter of the catheter assembly 600, overmolding or overlapping of the material of the first portion 619 onto the outer surface 620 of the wall 616 of the second portion 621 may be prevented during the insert molding operation or, alternatively, overmolded or overlapping material may be removed from the outer surface of the second portion after the insert molding operation. As another alternative, the first and second portions 619 and 621 may be separately formed and then joined together end-to-end in a butt joint with a biocompatible adhesive.

The durometer of the first and second portions 619 and 621 can be adjusted using cross-linking agents and fillers. One possible filler is barium sulfate, which would provide radiopacity for the central catheter 612. Optionally, a tether (not shown) formed of a flexible, non-ferrous material may be bonded or otherwise attached at one end to the first portion 619 of the wall 616 of the central catheter 612 and at an opposite end to the second portion 621 of the wall or another portion of the catheter assembly 600. Such a tether (not shown) would help to ensure that the first portion 619 of the wall 616 is not completely disconnected from the remainder of the catheter assembly 600 if the joint between the first portion and the second portion 621 of the wall unexpectedly fails.

The inner surface 618 of the wall 616 defines a central lumen 622 that extends substantially the entire length of the central catheter 612. The central lumen 622 is closed at the distal end 624 of the central catheter 612 by a plug 626 that is formed of a medical-grade elastomeric material and that is secured to the wall 616. The elastomeric material of which the plug 626 is formed has a relatively high durometer and, for an elastomeric material, a relatively high modulus of elasticity and, therefore, is relatively inextensible. For example, a suitable elastomer for the plug 626 may have a Shore A hardness of from about 80 to about 90. Because the plug 626 is relatively inextensible and is secured to the wall 616, the plug helps to restrict or limit the extension or distension of the wall adjacent to the plug, even though the wall adjoining the plug is formed of relatively low durometer and, therefore, relatively extensible elastomeric material. Accordingly, the portion of the wall 616 adjoining or immediately adjacent to the plug 626, including the distal end 624 of the central catheter 612, is formed with an outer diameter that is (a) less than the outer diameter of the first portion 619 of the wall when the first portion is not distended and (b) also equal to or less than the outer diameter of the first portion 619 of the wall when the first portion of the wall is extended or distended as described below.

To help further restrict or limit the extension or distension of the wall adjacent to the plug 626, a cup-shaped cap 627 is positioned in the central lumen of the central catheter 612 adjacent to the plug. The cup-shaped cap 627 has a closed end portion 629 that is relatively thick. The closed end portion 629 of the cup-shaped cap 627, like the plug 626, is located beyond the first portion 619 of the wall 616 in a distal direction. The material of which the cap 627 is formed has a higher durometer and a higher modulus of elasticity than the elastomeric material of which the plug 626 is formed. For example, a suitable material for the cap 627 may be polyether ether ketone (PEEK), which may have a Shore D hardness of about 80. Because the cap 627 is relatively inextensible and is secured to the wall 616, the cap further restricts or limits the extension or distension of the wall adjacent to the plug 626 and the cap.

The plug 626 and the cap 627 may be fabricated outside of the central catheter 612 and then inserted into the central lumen 622 and secured to the inner surface 618 of the wall 616 by a biocompatible adhesive (not shown). Alternatively, the plug 626, at least, may be formed of a flowable and curable biocompatible material, such as a liquid silicone elastomer. The flowable and curable material is introduced into the central lumen 622 at the distal end 624 of the central catheter 612 and is cured in place so as to bond to the inner surface 618 of the wall 616. A primer may be applied to the wall 616 before applying the adhesive or before introducing the flowable and curable material so as to enhance the strength of the joint between the plug 626 and the wall. An end surface of the plug 626 presented toward the central lumen 622 contacts the closed end portion 629 of the cup-shaped cap 627. The open end of cup-shaped cap 627 is, in turn, presented to the central lumen 622 to receive the end of a stylet 678, as explained in more detail below. Opposite the plug 626, at the proximal end 628 of the central catheter 612, the central lumen 622 is open.

As shown in FIG. 19, tunnels or passages 630 are formed in the wall 616 of the central catheter 612 and extend generally lengthwise of the central catheter. Two passages 630 are shown in FIG. 19 at diametrically opposite positions about the circumference of the wall 616. The wall 616 of the central catheter 612 includes four such passages 630, but may include more or fewer such passages 630, as desired. Each of the passages 630 is substantially identical in construction to the other passages 630. Like the passages 130 of the catheter assembly 100 shown in FIGS. 4-5, each of the passages 630 receives an associated peripheral catheter 614. The peripheral catheters 614 are thus disposed in the wall 616 of the central catheter 612, radially outward of the inner surface 618 of the wall 616 and, for a major portion of their lengths, radially inward of the outer surface 620 of the wall 616. This major portion of the lengths of the peripheral catheters 614 extends lengthwise substantially parallel to the central catheter 612.

Each peripheral catheter 614 has a central lumen 632, which is disposed outside of the central lumen 622 of the central catheter. Likewise, the central lumen 622 of the central catheter 612 is disposed outside of the central lumens 632 of the peripheral catheters 614. Each peripheral catheter 614 is formed of a biocompatible material, such as PTFE, that has sufficient rigidity to penetrate a patient's tissue and also has sufficient flexibility and resilience to withstand being deflected and then return to a non-deflected position.

As can be seen from FIG. 19, the outer diameter of each of the peripheral catheters 614 is smaller than the thickness of the wall 616 of the central catheter 612 and, at least in the first portion 619 of the length of the wall 616, smaller than the diameter of the associated passage 630. In the second portion 621 of the length of the wall 616, the outer diameter of each of the peripheral catheters 614 may also be smaller than the diameter of the associated passage 630. Alternatively, the outer diameter of each of the peripheral catheters 614 in the second portion 621 of the length of the wall 616 may be approximately the same as or slightly larger than the diameter of the associated passage 630 to provide an interference fit with the wall. Such an interference fit may result in the peripheral catheters 614 making the elastomeric material of the second portion 621 of the wall 616 less extensible (or more inextensible) if the peripheral catheters are made of a material that is less extensible than the elastomeric material of the second portion. A similar effect on the extensibility of the second portion 621 of the length of the wall 616 may be achieved by adhesively bonding the peripheral catheters 614 to the surface of the wall that defines the passages 630 in the second portion of the length of the wall. The extensibility of the second portion 621 of the length of the wall 616 may also be similarly affected by forming additional passages in just the second portion and inserting lengths of peripheral catheter material or other flexible, relatively inextensible material into the additional passages and bonding the lengths of material to the wall.

A distal end portion 634 of each peripheral catheter 614 can project radially outward of the outer surface 620 of the wall 616 of the central catheter 612 near the distal end 624 of the central catheter. To facilitate such radially outward projection of the peripheral catheter 614, the distal end portion of each passage 630 in the wall 616 of the central catheter 612 curves or angles radially outward, as a departure ramp, and opens onto the outer surface 620 of the wall 616. The point at which each passage 630 opens onto the outer surface 620 is located in the portion of the wall 616 immediately adjacent to the plug 626 and the cap 627 and beyond the first portion 619 of the wall 616 in a distal direction. A short length of tubing, such as PTFE tubing, (not shown) may be positioned in the radially curved or angled portion of the passage 630 and bonded to the wall 616 to act as a bearing surface for sliding movement of the peripheral catheter 614 relative to the wall 616. The distal end portion 634 of the peripheral catheter 614 has a predetermined shape in the form of an outwardly directed curve or hook, although other shapes, such as a substantially straight line oriented at a relatively small angle to the remainder of the peripheral catheter, may be used.

The proximal end 628 of the central catheter 612 and the proximal end portions 636 of the peripheral catheters 614 are connected to a hub 638. The hub 638 is formed of plastic, although it may be formed of other materials. The hub 638 includes a main body portion 640 and a cover portion 642 that extends rearwardly or proximally (to the right as viewed in FIG. 18) from the main body portion. The main body portion 640 has an elongated tubular shape with an open distal end and an open proximal end. The proximal end 628 of the central catheter 612 is received in the open distal end of the main body portion 640 of the hub 638. Inside the main body portion 640 is a bushing (not shown). The outer surface 620 of the wall 616 of the central catheter 612 is bonded to an adjacent, circumferentially extending inner surface (not shown) of the bushing (not shown).

The peripheral catheters 614, which are disposed in the wall 616 of the central catheter, are also received in the main body portion 640 of the hub 638. The peripheral catheters 614 extend into the bushing (not shown) in the main body portion 640 and beyond the proximal end 628 of the central catheter 612. Within the bushing (not shown), the peripheral catheters 614 are received in passageways (not shown) and are adhesively bonded to adjacent inner surfaces (not shown) of the bushing (not shown) that define the passageways. The peripheral catheters 614 then extend out of and proximally beyond the bushing and are received in grooves (not shown) formed in the bottom (as viewed in FIG. 18) of the main body portion 640 of the hub 638. In the course of traversing the space within the main body portion 640 between the bushing (not shown) and the grooves (not shown), the peripheral catheters 614 are redirected from a first orientation in which the peripheral catheters are disposed in an array circumferentially around the central lumen 622 of the central catheter 612 into a second orientation in which the peripheral catheters are arrayed on one side of the central catheter.

After being redirected into the second orientation in which it is arrayed on one side of the central catheter 612, each peripheral catheter 614 extends out of the proximal end of the main body portion 640 of the hub 638 downwardly (as viewed in FIG. 18) away from the hub. The proximal end portion 636 of each peripheral catheter 614 is associated with a fluid inlet port or injection port assembly 646, which receives the proximal end portion of its associated peripheral catheter. Between the main body portion 640 of the hub 638 and the injection port assembly 646, each peripheral catheter 614 is received inside a length of silicone tubing 648, which helps to protect the peripheral catheter. The length of silicone tubing 648 is attached, by adhesive, for example, to the injection port assembly 646 associated with the peripheral catheter 614.

Each injection port assembly 646 includes a connector portion 650, such as a Luer lock connector. Although a female Luer lock connector may be used in the connector portion 650, a male Luer lock connector or other atypical connector may alternatively be used to help prevent inadvertent connection of the injection port assembly 646 to commonly used fluid sources not intended for use with the catheter assembly 600. The central lumen 632 of the peripheral catheter 614 communicates with a central lumen 652 in the connector portion 650 of the injection port assembly 646. A surface (not shown) of the connector portion 650 is threaded to facilitate attachment of a second connector (not shown) and tubing (not shown) for delivering a fluid to the connector portion and thus to the peripheral catheter 614. Such a fluid may flow along the central lumen 632 of the peripheral catheter 614 from its proximal end portion 636 into the distal end portion 634 of the peripheral catheter. The distal end of the peripheral catheter 614 is open so that fluid may flow out of the open distal end of the peripheral catheter.

The cover portion 642 of the hub 638 includes a closure 653 and a latch 654. The closure 653 is shaped to close a significant part of the open proximal end of the main body portion 640 of the hub 638. With the cover portion 642 and closure 653 in place, the only part of the open proximal end of the main body portion 640 that remains open is a part that permits the peripheral catheters 614 to extend out of the main body portion. The latch 654 has an elongated tubular shape and extends away from the closure 653 in a proximal direction (to the right, as viewed in FIG. 18). The latch is generally rectangular in cross-section with rounded corners. An inner surface of the latch 654 and the cover portion 642 defines a lumen 656, which is coaxial with the central lumen 622 in the central catheter 612. An outer surface 660 of the latch 654 of the cover portion 642 is formed with two outwardly projecting teeth 662 disposed adjacent to, but spaced from the closure 653. The teeth 662 comprise a part of a control mechanism 664.

The latch 654 of the cover portion 642 of the hub 638 is shaped and dimensioned to be received in a stylet handle assembly 666. The stylet handle assembly 666 and the catheter assembly 600 together form a catheter apparatus 601. The stylet handle assembly 666 comprises a housing 668, a handle 670, and two arms 672. The housing 668, the handle 670, and the arms 672 are formed in one piece from a polymeric material, although they may be formed of other materials.

The housing 668 is hollow and elongated. The housing 668 is also generally rectangular in cross-section with rounded corners. The internal shape of the housing 668 is substantially the same as the external shape of the latch 654, excluding the teeth 662. The internal dimensions of the housing 668 are slightly larger than the external dimensions of the latch 654. The distal end 674 of the housing 668 is open. Consequently, the housing 668 is able to receive the portion of the latch 654 that is proximal of the teeth 662.

The proximal end 676 of the housing 668 is also open, but mates with and is closed by the handle 670. The handle 670 includes a tubular central body 680 and two laterally extending wings 682. The laterally extending wings 682 both lie in the same plane and include raised ribs 684 to facilitate the handle 670 being gripped by a user of the stylet handle assembly 666. The tubular central body 680 includes a central lumen (not shown) that is formed to receive the stylet 678. The stylet 678 is formed of a metal alloy, such as 35N LT, and has a rounded distal end (not shown). The 35N LT metal alloy, which is sold by Fort Wayne Metals Research Corp. of Fort Wayne, Ind., provides stiffness and also MRI compatibility as it is both non-magnetic and non-shadowing. When received in the central lumen (not shown) in the tubular central body 680 of the handle 670, the stylet 678 extends lengthwise of both the handle 670 and the housing 668. The proximal end (not shown) of the stylet 678 is fixed to the handle 670 adjacent its proximal end.

The arms 672 of the stylet handle assembly 666 extend laterally from opposite sides of the exterior of the housing 668. Each arm 672 has a curved portion 686, a straight portion 688, and a hook portion 690. The curved portion 686 of each arm 672 is attached at one end to the housing 668. The curved portion 686 of each arm 672 extends in a proximal direction away from the exterior of the housing 668. The end of the curved portion 686 farthest from the housing 668 joins a proximal end of the straight portion 688. The junction between the curved portion 686 and the straight portion 688 of each arm 672 has a surface that can be engaged by a thumb or finger of a user of the stylet handle assembly 666. The straight portion 688 of each arm 672 extends in a distal direction away from the junction with the curved portion 686. The straight portion 688 extends farther in a distal direction than the housing 668. As a result, the distal end of the straight portion 688 is disposed beyond the distal end 674 of the housing 668. The hook portion 690 of each arm 672 extends inwardly from the distal end of the straight portion 688.

When the latch 654 of the cover portion 642 of the hub 638 is received in the open distal end 674 of the housing 668, the latch can slide or otherwise extend into the housing to a position in which the teeth 662 of the latch are disposed farther in a proximal direction than the hook portions 690 of the arms 672. As the latch 654 is moved into the housing 668, the hook portions 690 of the arms 672 engage the teeth 662 on the latch. Specifically, due to the lateral dimensions of the teeth 662, the hook portions 690 of the arms 672 are resiliently deflected laterally outwardly by the teeth when the hook portions and the teeth initially engage one another. Continued proximal movement of the latch 654 caused the teeth 662 to reach a position that is proximally beyond the hook portions 690 of the arms 672. At that point, the hook portions 690 resiliently snap back to their original positions and block the teeth 662 and the latch 654 from moving in a distal direction out of the housing 668.

As will be apparent from the foregoing description, the teeth 662 of the latch 654 and the hook portions 690 of the arms 672 together form the control mechanism 664. The control mechanism 664 controls relative movement between the stylet 678 and the first portion 619 of the wall 616, in part, by blocking relative movement of the latch 654 and the hub 638, on the one hand, and the housing 668 and the stylet handle assembly 666, on the other hand, in a direction away from each other.

Relative movement of the catheter assembly 600 and the stylet handle assembly 666 toward and into engagement with one another produces lengthwise movement of the hub 638 relative to the stylet 678, which is fixed to the handle 670 of the stylet handle assembly. The positions of the teeth 662 on the cover portion 642 of the hub 638 and the positions of the hook portions 690 of the arms 672 relative to the distal end of the housing 668 can be predetermined to permit a desired amount of relative movement between the hub 638 and the stylet handle assembly 666. As explained below, a predetermined amount of relative movement between the hub 638 and the stylet 678 produces a predetermined amount of extension of the first portion 619 of the length of the wall 616, a predetermined amount of reduction in the outer diameter of the first portion of the wall, and a predetermined amount of lengthwise deployment of the peripheral catheters 614. The control mechanism 664 is thus operable to produce predetermined relative movement between the hub 638 and the stylet 678 and predetermined deployment of the peripheral catheters 614.

As can be seen in FIG. 18, the second orientation of the peripheral catheters 614, in which the peripheral catheters and their associated injection port assemblies 646 are all arrayed on one side of the central catheter 612, helps a user of the stylet handle assembly 466 to grasp and manipulate the stylet handle assembly. More particularly, having the peripheral catheters 614 and their associated injection port assemblies 646 on one side of the central catheter 612 and, therefore, on one side of the stylet handle assembly 666 permits a user of the stylet handle assembly to approach from other sides of the stylet handle assembly without having to maneuver around the peripheral catheters and injection port assemblies. Nonetheless, if desired, the peripheral catheters 614 could be maintained in their first orientation disposed in an array circumferentially around the central lumen 622 of the central catheter 612 as they are directed through the main body portion 640 of the hub 438.

When the catheter assembly 600 is to be inserted into tissue, such as cerebral tissue, of a patient, stylet 678 is received in and engaged with the stylet handle assembly 666. Specifically, the proximal end (not shown) of the stylet 678 is inserted into the distal end 674 of the housing 668 of the stylet handle assembly 666 and fixed in the handle 670 of the stylet handle assembly. The distal end (not shown) of the stylet 678 is inserted into and pushed lengthwise through the lumen 656 formed in the latch 654 of the cover portion 642 of the hub 638. The distal end (not shown) of the stylet 678 is then pushed lengthwise through the main body portion 640 of the hub 638 and into the central lumen 622 of the central catheter 612. As the distal end (not shown) of the stylet 678 approaches the distal end 624 of the central catheter 612, the proximal end of the latch 654 of the cover portion 642 of the hub 638 of the catheter assembly 600 enters the stylet handle assembly 666 through the open distal end 674 of the housing 668 of the stylet handle assembly.

As the distal end (not shown) of the stylet 678 reaches the cap 627 adjacent the plug 626 at the distal end 624 of the central catheter 612, the stylet is received in the open end of the cup-shaped cap, which is presented toward the central lumen 622 of the central catheter 612. In particular, the distal end (not shown) of the stylet 678 is received in the pocket provided by the cup-shaped cap 627 so that the distal end and the pocket together help to center the stylet in the central lumen 622. The distal end (not shown) of the stylet 678 may be rounded or may have a different shape, and the pocket provided by the cup-shaped cap 627 has a complementary shape to help center the stylet in the central lumen. When the distal end (not shown) of the stylet 678 is fully received in the cup-shaped cap 627 and contacts the closed end portion 629 of the cap, the first portion 619 of the length of the wall 616 is not yet extended, and the distal end portions 634 of the peripheral catheters 614 project from the first portion of the length of the wall, as shown in FIG. 18.

After the distal end (not shown) of the stylet 678 contacts the closed end portion 629 of the cap 627, the user of the stylet handle assembly 666 continues to move the handle 670 toward the hub 638. As the latch 654 is pushed farther into the housing 668 of the stylet handle assembly 666, the entire catheter assembly 600 is moved toward the stylet handle assembly, and the stylet 678 is pressed against the cap 627 adjacent the distal end 624 of the central catheter 612. Pressing the stylet 678 against the closed end portion 629 of the cap 627 causes the first portion 619 of the length of the wall 616 to extend or distend axially or lengthwise into a longitudinally extended condition.

The extension or stretching of the wall 616 occurs primarily in the thickened first portion 619 of the wall because the cap 627 and the plug 626 are made of relatively inextensible material and are bonded to the inner surface 618 of the wall beyond the first portion of the wall in a distal direction. The plug 626 and the cap 627 thus effectively transfer the force applied by the stylet 678 to the wall 616 in the first portion 619 of its length. In addition, the first portion 619 of the length of the wall 616 is made of lower durometer and relatively more extensible material than the second portion 621 of the wall and thereby tends to extend or stretch in preference to the second portion of the length of the wall.

Extension or stretching of the first portion 619 of the length of the wall 616 causes the outer diameter of the wall to decrease or be reduced. This can be seen in FIGS. 20 and 21 by comparing the outer diameter of the first portion 619 in FIG. 20 with the outer diameter of the first portion in FIG. 21. The outer diameter of the first portion 619 of the wall 616 may be reduced to any desired extent, such as less than or equal to the outer diameter of the second portion 621 of the wall. Extension or stretching of the first portion 619 of the length of the wall 616 of the central catheter 612 also causes the first portion of the wall to be drawn over the distal end portions 634 of the peripheral catheters 614 or, in effect, causes the distal end portions of the peripheral catheters to be withdrawn into the passages 630 in the wall 616. This result occurs because the peripheral catheters 614 are adhesively bonded to surfaces (not shown) of the bushing (not shown) in the main body portion 640 of the hub 638 or are otherwise fixed against movement relative to the hub 638.

FIGS. 20 and 21 also illustrate that extension or stretching of the first portion 619 of the length of the wall 616 does not affect the distance between distal end 624 of the central catheter 612 and the point at which each passage 630 opens onto the outer surface 620 of the wall. This distance is identified as "L1" in FIGS. 20 and 21. In other words, the point at which the each passage 630 opens onto the outer surface 620 of the wall 616 remains at a substantially constant distance from the distal end 624 of the central catheter 612 during any extension or stretching of the first portion 619 of the length of the wall. The peripheral catheters 614 thus emerge from the wall 616 of the central catheter 612 at a substantially constant distance relative to the distal end 624 of the central catheter.

The durometers and thicknesses of the elastomeric materials used in the first and second portions 619 and 621 of the length of the wall 616 can be selected or tuned to provide a desired amount of reduction in the outer diameter of the first portion of the wall without excessive longitudinal extension of the first portion or use of excessive force. The durometers and thicknesses of the elastomeric materials used in the first and second portions 619 and 621 of the length of the wall 616 can also be selected or tuned to provide a desired extent to which the first portion of the wall is drawn over the distal end portions 634 of the peripheral catheters 614 without excessive longitudinal extension of the first portion. Such an extension of the first portion 619 of the wall 616 should also produce a corresponding reduction in the outer diameter of the first portion of the wall so that the outer diameter of the first portion is equal to or less than the outer diameter of the second portion 621 of the length of the wall.

As they are being covered by the wall 616 of the first portion 619 of the length of the central catheter 612 or, in effect, withdrawn into the passages 630, the distal end portions 634 of the peripheral catheters 614 are deflected from their outwardly directed, predetermined shape and are constrained in a generally straight configuration by the wall of the central catheter. When the peripheral catheters 614 have been fully withdrawn or retracted into the wall 616 of the central catheter 612, the outer surface 620 of the wall 616 of the central catheter appears essentially smooth and uninterrupted. The wall 616 of the central catheter 612 thus functions as a sheath portion of the central catheter and covers the distal end portions 634 of the peripheral catheters 614.

When the stylet 678 reaches the end of its stroke, as determined by engagement or latching of the hook portions 690 of the arms 672 against the distal surfaces of the teeth 662 of the cover portion 642 of the hub 638, the stylet is secured in place to facilitate coordinated manipulation of the stylet and the catheter assembly 600. When the stylet handle assembly 666 is secured to the hub 638, the stylet 678 and the catheter assembly 600 tend to move more consistently as a single unit and can be manipulated more easily and accurately. In particular, the stylet 678 can then be used to insert the extended central catheter 612 and the peripheral catheters 614 into the tissue of a patient. Because the outer diameter of the first portion 619 of the wall 616 of the central catheter 612 has been reduced due to the lengthwise extension or distension of the first portion, the opening formed in the patient's tissue is smaller than it would be otherwise. Also, because the distal end portions 634 of the peripheral catheters 614 have been withdrawn into the wall 616 of the central catheter, the peripheral catheters do not interfere with the insertion of the central catheter into the patient's tissue.

When the distal end 624 of the central catheter 612 is appropriately positioned in a patient's tissue, the hub 638 of the catheter assembly 600 is held so as to maintain the distal end of the central catheter in position. The arms 672 of the stylet handle assembly 666 can then be manipulated to disengage the hook portions 690 of the arms 672 from the teeth 662 of the cover portion 642 and to cause or permit relative movement between (a) the catheter assembly 600 and (b) the stylet handle assembly 666 and the stylet 678. In particular, the resilience of the extended first portion 619 of the wall 616 of the central catheter 612 pulls the proximal end 628 of the central catheter in a distal direction toward the distal end 624 of the central catheter. The central catheter 612 thus returns resiliently to its initial, non-extended length, as shown in FIG. 18.

As can be seen from the foregoing description, the control mechanism 664, which includes the teeth 662 of the cover portion 642 and the hook portions 690 of the arms 672, controls relative movement between the stylet 678 and the first portion 619 of the wall 616, in part, by permitting relative movement of the hub 638 and the catheter assembly 600, on the one hand, and the housing 668 and the stylet handle assembly 666, on the other hand, away from each other. Although the relative movement has been described in terms of the proximal end 628 of the central catheter 612 moving in a distal direction toward the distal end 624 of the central catheter, the relative movement may involve movement of the distal end of the central catheter in a proximal direction toward the proximal end of the central catheter. In that event, the stylet 678 would be pushed by the distal end 624 of the central catheter 612 in a proximal direction, which, in turn, would push the stylet handle assembly 666 in a proximal direction away from the hub 638 of the catheter assembly 600.

When the central catheter 612 resiliently returns to its initial, non-extended length and the wall 616 of the central catheter likewise resiliently returns from its longitudinally extended condition to its initial, non-extended length, the distal end portions 634 of the peripheral catheters 614 are no longer withdrawn into the wall 616. The distal end portions 634 of the peripheral catheters 614 instead project from the outer surface 620 of the wall 616 of the central catheter and assume their outwardly directed, predetermined shape. As the distal end portions 634 of the peripheral catheters 614 assume their outwardly directed, predetermined shape, the peripheral catheters 614 penetrate the patient's tissue and extend into the patient's tissue away from the central catheter 612 in a radial array.

In addition, as the wall 616 of the central catheter 612 resiliently returns to its initial length, the outer diameter of the wall, particularly the first portion 619, increases from its reduced condition back to its original dimension. The increase in the outer diameter of the wall 616 of the central catheter 612 causes the outer surface 620 of the first portion 619 of the wall 616 to press tightly against adjacent surfaces of the patient's tissue. The resulting close fit between the outer surface 620 of the wall 616 and the adjacent surfaces of the patient's tissue helps to prevent fluid introduced into the tissue by the peripheral catheters 614 from flowing back along the outer surface of the wall toward the proximal end 628 of the central catheter 612.

When the stylet handle assembly 666 is disengaged from the catheter assembly 600, the durometer of the elastomeric material in the first portion 619 of the length of the wall 616 affects the speed and force with which the central catheter 612 resiliently returns to its initial, non-extended length and the proximal end 628 of the central catheter moves in a distal direction. If, for example, the first portion 619 of the length of the wall 616 is formed of a silicone elastomer with a Shore A hardness of about 40, the first portion will return to its initial, non-extended length more quickly than if the first portion is formed of a silicone elastomer with a Shore A hardness of about 20, provided the durometer of the elastomeric material in the second portion 621 of the length of the wall 616 is the same in both instances. A quicker return of the first portion 619 to its initial, non-extended length will produce a quicker deployment of the peripheral catheters 614.

At the same time, to ensure stretching or extension of the first portion 619 of the length of the wall 616 in preference to stretching and extension of the second portion 621 of the length of the wall, a minimum difference should be maintained between the durometers of the materials from which the first and second portions are formed. With silicone elastomers having durometers measured using the Shore A scale, a minimum, it has been determined empirically that a minimum practical difference between the durometers of the materials from which the first and second portions 619 and 621 are made is about 30. This minimum desired difference between the durometers of the materials from which first and second portions 619 and 621 of the length of the wall 616 are formed may also be applied if one or both of the first and second portions is formed of a material, such as a urethane, with a durometer measured using the Shore D scale. The measured Shore D durometers may be converted to Shore A durometers, or the minimum desired difference of about 30 may be converted to, for example, a difference using the Shore D scale.

Another way of establishing the desired difference between the durometers of the materials is to view the difference as a minimum ratio between the hardnesses or durometers of the first and second portions 619 and 621 of the length of the wall 616. It has been empirically determined that a minimum practical ratio of the durometer of the material from which the first portion 619 of the length of the wall 616 is made to the durometer of the material from which the second portion 621 is made is about 1.5 to 1. A maximum practical ratio between the hardnesses or durometers of the second and first portions 621 and 619 has been determined empirically to be about 9 to 1. With elastomeric materials having durometers measured using the Shore A scale, the empirically determined maximum practical difference between the durometers of the materials from which the first and second portions 619 and 621 are made is about 80.

With the central and peripheral catheters 612 and 614 of the catheter assembly 600 appropriately positioned in the patient's tissue, therapeutic treatment of the tissue with a bioactive material can begin. To introduce the bioactive material, the threaded surface (not shown) of the connector portion 650 of each injection port assembly 646 is connected with a connector (not shown) and the distal end of a length of tubing (not shown). A proximal end (not shown) of the tubing is attached to a device (not shown), such as a pump, for delivering a fluid, such as a liquid. The fluid contains a bioactive material, such as a pharmaceutical material, and is delivered from the tubing into the central lumen 652 of the connector portion 650 of the injection port assembly 646 and then into the central lumen 632 of the associated peripheral catheter 614. The fluid flows along the central lumen 632 of the peripheral catheter 614 until it reaches the open end of the distal end portion 634 of the peripheral catheter and is thereby introduced into the patient's tissue.

If the patient's treatment is continued over an extended period of time and the catheter assembly 600 is therefore left implanted in the patient's tissue for an extended period of time, the stylet handle assembly 666 may be disengaged from the hub 638 of the catheter assembly, and the stylet may thereby be withdrawn entirely from the catheter assembly. Disengagement of the stylet handle assembly 666 and withdrawal of the stylet 678 from the catheter assembly 600 will leave open the proximal end of the lumen 656 in the cover portion 642 of the hub 638. Because the lumen 656 communicates, via the main body portion 640 of the hub 638, with the central lumen 622 of the central catheter 612, a cover (not shown) may be placed over the open proximal end of the lumen 656 to keep foreign materials from entering the proximal end 628 of the central lumen in the central catheter.

When the patient's treatment is completed, the catheter assembly 600 may be removed by pushing the stylet 678 into the catheter assembly to extend or distend the central catheter 612. If the stylet 678 has been disengaged from the catheter assembly 600, the stylet is reinserted into the lumen 656 formed in the latch 654 of the cover portion 642 of the hub 638 and pushed lengthwise through the lumen 656 toward the central catheter 612. As the stylet 678 is moved into and through the central lumen 622 of the central catheter 612, the latch 654 of the cover portion 642 of the hub 638 of the catheter assembly 600 enters the stylet handle assembly 666 through the open distal end 674 of the housing 668.

Pressing the distal end (not shown) of the stylet 678 against the cap 627 and the plug 626 adjacent the distal end 624 of the central catheter 612 as the stylet handle assembly 666 is moved closer to the hub 638 of the catheter assembly 600 causes the first portion 619 of the length of the wall 616 to extend or distend axially or lengthwise. Causing the first portion 619 of the length of the wall 616 to assume a longitudinally extended condition effectively causes the distal end portions 634 of the peripheral catheters 614 to be withdrawn into the passages 630 in the wall 616. When the peripheral catheters 614 have been fully withdrawn or retracted into the wall 616 of the central catheter 612, and the hook portions 690 of the arms 672 have engaged the distal surfaces of the teeth 662 of the latch 654, the stylet handle assembly 666 can be moved away from the patient, thereby withdrawing the catheter assembly 600 from the patient's tissue.

To enhance the convenience of using the catheter assembly 600 and, specifically, to facilitate positioning of the central catheter 612 lengthwise in a patient's tissue, the outer surface 620 of the second portion 621 of the wall 616 includes distance indicia 692 to show the distance along the second portion from the proximal end 628 of the central catheter. The distance indicia 692 may be molded into the outer surface 620 or bonded or otherwise applied to the outer surface.

Also to enhance the convenience of using the catheter assembly 600, the peripheral catheters 614 are identified at different points in the catheter assembly by reference indicia 694 and 696. In particular, reference indicia 694 are molded into or applied to an outer surface of the main body portion 640 of the hub 638 adjacent the distal end of main body portion, which is adjacent the proximal end 628 of the central catheter 612. At that location in the catheter assembly 600, the peripheral catheters 614 are in their first orientation disposed in an array circumferentially around the central lumen 622 of the central catheter 612. The reference indicia 694, therefore, similarly appear in a circumferential array around the main body portion 640 of the hub 638 so that a different reference indicium 696 is associated with each different peripheral catheter 614. The reference indicia 694 are the numerals "1" through "4" and are positioned adjacent corresponding peripheral catheters 614. The reference indicia 696 are also the numerals "1" through "4" and are molded into or applied to outer surfaces of the injection port assemblies 646. A different numeral or reference indicium 696 is associated with each different injection port assembly 646. In each case, however, the numeral or reference indicium 696 associated with a particular peripheral catheter 614 is the same as the numeral or reference indicium 694 associated with that particular peripheral catheter.

The reference indicia 694 and 696 can be used to help identify the position of the peripheral catheters 614 relative to the central catheter 612 and, therefore, the patient's tissue. The material of which the peripheral catheters 614 are made may also be color-coded to help identify and distinguish between different peripheral catheters. Although the reference indicia 694 and 696 are shown in FIG. 18 as being numerals, they could be in any other distinguishing form, such as letters, colors, geometric shapes, or other symbols.

FIG. 22 illustrates yet another alternative configuration for the wall of the central catheter. As shown, the first portion 719 of the length of the wall 716 of a central catheter 712 has an outer surface 720 formed with raised, annular ridges 798 encircling the central catheter. The raised ridges 798 are spaced apart along the length of the first portion 719 of the length of the wall 716 of the central catheter 712. Five raised ridges 798 are shown, but a greater or lesser number of raised ridges may be used.

Use of such raised ridges 798 can enhance sealing of the outer surface 720 of the wall 716 against the adjacent surfaces of the patient's tissue to help prevent fluid introduced into the tissue by the peripheral catheters (not shown) from flowing back along the outer surface of the wall toward the proximal end (not shown) of the central catheter. Specifically, when the wall 716 of the central catheter 712 resiliently returns to its initial length after having been extended to facilitate introduction of the central catheter into a patient's tissue, the outer diameter of the wall, particularly the first portion 719, increases from its reduced diameter condition back to its original dimension. The increase in the outer diameter of the wall 716 of the central catheter 712 causes the outer surface 720 of the first portion 719 of the wall 716 to press tightly against adjacent surfaces of the patient's tissue. This is particularly so for the portions of the outer surface 720 that include the raised ridges 798. The resulting close fit between the outer surface 720 of the wall 716 and the adjacent surfaces of the patient's tissue helps to prevent fluid introduced into the tissue by the peripheral catheters (not shown) from flowing back along the outer surface of the wall toward the proximal end (not shown) of the central catheter.

The peripheral catheters 614, as well as the peripheral catheters 14, 114, 214, 314, and 414 of the embodiments of FIGS. 1-3, 4-5, 6-9, 10-12, and 13-15, respectively, may be made of a material having a shape memory. Such a shape memory material could be used to provide the peripheral catheters 14, 114, 214, 314, 414, and 614 with a substantially straight configuration at temperatures below a patient's normal body temperature. Such a shape memory material would provide the distal end portions 34, 134, 234, 334, 434, and 634 of the peripheral catheters 14, 114, 214, 314, 414, and 614 with a curved, angled, or other configuration when the peripheral catheters are exposed to a temperature at or above a patient's normal body temperature. Thus, when the catheter assemblies 10, 100, 200, 300, 400, and 600 using such a shape memory material are introduced into a patient's tissue, the patient's body temperature would cause the distal end portions 34, 134, 234, 334, 434, and 634 of the peripheral catheters 14, 114, 214, 314, 414, and 614 to assume a curved, angled, or other configuration and penetrate the patient's tissue.

As previously noted, each of the catheter assemblies 10, 100, 200, 300, 400, and 600 may have only single peripheral catheter 14, 114, 214, 314, 414, or 614 or may have an array of multiple peripheral catheters, such as six to eight or more. Moreover, although the distal end portions 34, 134, 234, 334, and 634 of the peripheral catheters 14, 114, 214, 314, and 614, respectively, are shown as having a predetermined curved configuration and as projecting radially outwardly from the central catheter 12, 112, 212, 312, and 612, respectively, the distal end portions may have other predetermined configurations, such as an angled or straight configuration, and may project from the central catheter in other directions, such as ninety degrees or another angle from the central catheter or axially through the distal end 24, 124, 224, 324, and 624, respectively, of the central catheter. The distal end portions 34, 134, 234, 334, 434, and 634 of the peripheral catheters 14, 114, 214, 314, 414, and 614, respectively, may be provided with their respective predetermined configurations by, for example, heat forming either before the peripheral catheters are connected with their respective central catheter 12, 112, 212, 312, 412, and 612 or after the peripheral catheters are connected with their respective central catheter.

If the distal end portions 34, 134, 434, and 634 of the peripheral catheters 14, 114, 414, and 614, respectively, have a straight configuration and have no angle or curve with respect to the remaining portions of the peripheral catheters, the distal end portions will not be deflected by the walls 16, 116, 416, and 616 of the central catheters 12, 112, 412, and 612, respectively, when the walls are extended. Likewise, if the distal end portions 234 of the peripheral catheters 214 have a straight configuration and have no angle or curve with respect to the remaining portions of the peripheral catheters, the distal end portions 234 of the peripheral catheters will not be deflected by the sheaths 292 when the wall 216 of the central catheter 212 has not yet been distended or extended sufficiently to release the sheaths.

While the central catheters 12, 112, 212, 312, 412, and 612 and peripheral catheters 14, 114, 214, 314, 414, and 614 have been described as being introduced into a patient's tissue and then later removed from the patient's tissue, the central and/or peripheral catheters may be fabricated of a material or materials that can be absorbed by the tissue, thereby reducing or eliminating the requirement physically to remove the catheters from the patient's tissue. Further, the peripheral catheters 14, 114, 214, 314, 414, and 614 may be fabricated of an electrically conductive material and electrically insulated with a coating or jacket except at the tips of the distal end portions 34, 134, 234, 334, 434, and 634, respectively, of the peripheral catheters. The peripheral catheters 14, 114, 214, 314, 414, and 614 could thus function as electrodes, conducting electrical signals applied to the proximal end portions of the peripheral catheters to the patient's tissue for therapeutic electrical stimulation. Finally, while the use of biocompatible adhesive materials has been described above to secure the peripheral catheters 14, 114, 414, 614 to the wall 16, 116, 416, 616 of the central catheter 12, 112, 412, 612 as well as to secure or attach together other components of the catheter assemblies 10, 100, 200, 300, 400, and 600, other suitable attachment or fixation mechanisms, such as radio frequency welding and molded interlocking pins or other interlocking structural features, may be used where appropriate.

It will be appreciated that the catheter assemblies 10, 100, 200, 300, 400, and 600 may be used to treat both neoplastic and non-neoplastic disorders. Bioactive materials introduced into a patient's tissue using any of the catheter assemblies 10, 100, 200, 300, 400, and 600 may include, for example, chemotherapeutic materials, viruses, proteins, radiologic materials, growth factors, peptides, and non-radioactive tracer molecules. The catheter assemblies 10, 100, 200, 300, 400, and 600 may be used in a variety of patient tissues, including, for example, brain tissue, spinal cord tissue, and tissue of any organ.

From the above description of the invention, those skilled in the art will perceive improvements, changes and modifications. Such improvements, changes, and/or modifications within the skill of the art are intended to be covered by the appended claims.

Having described the invention, the following is claimed:

1. A catheter assembly comprising:
a first catheter including a wall with an inner surface at least partially defining a lumen; and
a second catheter connected to the wall of the first catheter and disposed outward of the inner surface of the wall, the second catheter being at least partially covered by a sheath portion of the first catheter,
a first portion of the wall of the first catheter being made of a relatively low durometer elastomeric material and being relatively extensible, a second portion of the wall being formed of a relatively high durometer elastomeric material and being relatively inextensible, extension of the first portion of the wall causing relative movement between the first portion of the wall and an adjacent portion of the second catheter.

2. A catheter assembly according to claim 1 wherein the durometer of the relatively high durometer elastomeric material has a minimum ratio to the durometer of the relatively low durometer elastomeric material of about 1.5 to 1.

3. A catheter assembly according to claim 1 further comprising at least a portion of a control mechanism to grasp a stylet disposed in the lumen and to control relative movement between the stylet and the first portion of the wall and consequent extension of the first portion of the wall.

4. A catheter assembly according to claim 3 wherein the control mechanism includes a lead screw and a nut to produce the relative movement between the stylet and the first portion of the wall, the at least a portion of the control mechanism including at least one of the lead screw and the nut.

5. A catheter assembly according to claim 3 further comprising a hub connecting a proximal end portion of the first catheter to a proximal end portion of the second catheter, the hub including the at least a portion of the control mechanism.

6. A catheter assembly according to claim 5 wherein the hub includes a first portion of a detent device, the first portion of the detent device being engageable with a second portion of the detent device to impede relative movement between the hub and the stylet.

7. A catheter assembly according to claim 1 further comprising a plurality of second catheters and a hub connecting a proximal end portion of the first catheter to a proximal end portion of each of the plurality of second catheters.

8. A catheter assembly according to claim 1 wherein the lumen communicates with an opening formed in a distal end of the first catheter, the opening being closed with an occluding material that is less extensible than the relatively low durometer elastomeric material forming the first portion of the wall, the occluding material being shaped and dimensioned to receive an end of a stylet.

9. A catheter assembly according to claim 8 wherein the occluding material is formed as a plug and is adhesively bonded to the first portion of the wall.

10. A catheter assembly according to claim 1 wherein the wall of the first catheter also has an outer surface, the outer surface of the second portion of the wall including a trough to receive the second catheter.

11. A catheter assembly according to claim 1 wherein the second catheter has a predetermined shape, the predetermined shape being provided by heat forming the second catheter before the second catheter is connected to the wall of the first catheter.

12. A catheter assembly according to claim 1 wherein the second catheter has a predetermined shape, the predetermined shape being provided by heat forming the second catheter after the second catheter is connected to the wall of the first catheter.

13. A catheter assembly according to claim 1 wherein the sheath portion of the first catheter includes the first portion of the wall of the first catheter, the first portion of the wall having an outer surface, the second catheter being at least partially disposed between the inner and outer surfaces of the wall.

14. A catheter assembly according to claim 13 wherein the lumen communicates with an opening formed in a distal end of the first catheter, the opening being closed with an occluding material that is less extensible than the relatively low durometer elastomeric material forming the first portion of the wall, the second catheter projecting out of the sheath portion of the first catheter adjacent to the occluding material.

15. A catheter assembly according to claim 1 wherein the wall of the first catheter has an outer surface, the sheath portion of the first catheter and at least a portion of the second catheter being disposed outward of the outer surface of the wall of the first catheter.

16. A catheter assembly according to claim 1 wherein the second catheter has a predetermined shape, the second catheter being deflected from the predetermined shape when covered by the sheath portion of the first catheter.

17. A catheter assembly according to claim 1 wherein the second catheter projects out of the sheath portion of the first catheter when the first portion of the wall of the first catheter is extended.

18. A catheter assembly comprising:
a first catheter including a wall with an inner surface at least partially defining a lumen extending lengthwise of the first catheter; and
a second catheter at least partially disposed in the wall of the first catheter outward of the inner surface of the wall and extending lengthwise of the first catheter,
a first portion of the wall of the first catheter being made of a relatively low durometer elastomeric material and being relatively extensible, a second portion of the wall being formed of a relatively high durometer elastomeric material and being relatively inextensible, extension of the first portion of the wall causing relative movement between the first portion of the wall and an adjacent portion of the second catheter.

19. A catheter assembly according to claim 18 wherein the durometer of the relatively high durometer elastomeric material has a minimum ratio to the durometer of the relatively low durometer elastomeric material of about 1.5 to 1.

20. A catheter assembly according to claim 18 further comprising at least a portion of a control mechanism to grasp a stylet disposed in the lumen and to control relative movement between the stylet and the first portion of the wall and consequent extension of the first portion of the wall.

21. A catheter assembly according to claim 20 wherein the control mechanism includes a lead screw and a nut to produce the relative movement between the stylet and the first portion of the wall, the at least a portion of the control mechanism including at least one of the lead screw and the nut.

22. A catheter assembly according to claim 20 further comprising a hub connecting a proximal end portion of the first catheter to a proximal end portion of the second catheter, the hub including the at least a portion of the control mechanism.

23. A catheter assembly according to claim 22 wherein the hub includes a first portion of a detent device, the first portion of the detent device being engageable with a second portion of the detent device to impede relative movement between the hub and the stylet.

24. A catheter assembly according to claim 18 further comprising a plurality of second catheters and a hub connecting a proximal end portion of the first catheter to a proximal end portion of each of the plurality of second catheters.

25. A catheter assembly according to claim 18 wherein the lumen communicates with an opening formed in a distal end of the first catheter, the opening being closed with an occluding material that is less extensible than the relatively low durometer elastomeric material forming the first portion of the wall, the occluding material being shaped and dimensioned to receive an end of a stylet.

26. A catheter assembly according to claim 25 wherein the occluding material is formed as a plug and is adhesively bonded to the first portion of the wall.

27. A catheter assembly according to claim 18 wherein the wall of the first catheter also has an outer surface, the lumen communicating with an opening formed in a distal end of the first catheter, the opening being closed with an occluding material that is less extensible than the relatively low durometer elastomeric material forming the first portion of the wall, the second catheter projecting out of the wall through the outer surface of the first catheter adjacent to the occluding material.

28. A catheter assembly according to claim 18 wherein the wall of the first catheter also has an outer surface, the outer surface of the second portion of the wall including a trough to receive the second catheter.

29. A catheter assembly according to claim 18 wherein the second catheter has a predetermined shape, the predetermined shape being provided by heat forming the second catheter before the second catheter is connected to the wall of the first catheter.

30. A catheter assembly according to claim 18 wherein the second catheter has a predetermined shape, the predetermined shape being provided by heat forming the second catheter after the second catheter is connected to the wall of the first catheter.

31. A catheter assembly according to claim 18 wherein the second catheter has a predetermined shape, the second catheter being deflected from the predetermined shape when disposed in the wall of the first catheter.

32. A catheter assembly according to claim 18 wherein the first portion of the wall of the first catheter is longitudinally extensible, the first portion of the wall having a diameter that is reduced when the first portion of the wall is longitudinally extended, the diameter of the first portion of the wall increasing from a reduced condition when the first portion of the wall resiliently returns from a longitudinally extended condition.

33. A catheter assembly comprising:
a first catheter including a wall with an inner surface at least partially defining a first lumen; and
a second catheter including a second lumen, the second catheter being disposed outward of the inner surface of the wall, the first catheter being disposed outside of the second lumen,
a first portion of the wall of the first catheter being made of a relatively low durometer elastomeric material and being relatively extensible, a second portion of the wall being formed of a relatively high durometer elastomeric material and being relatively inextensible, the second catheter being connected to the first portion of the wall of the first catheter, extension of the first portion of the wall causing relative movement between the first portion of the wall and an adjacent, outwardly disposed portion of the second catheter.

34. A catheter assembly according to claim 33 wherein the durometer of the relatively high durometer elastomeric material has a minimum ratio to the durometer of the relatively low durometer elastomeric material of about 1.5 to 1.

35. A catheter assembly according to claim 33 further comprising at least a portion of a control mechanism to grasp a stylet disposed in the first lumen and to control relative movement between the stylet and the first portion of the wall and consequent extension of the first portion of the wall.

36. A catheter assembly according to claim 35 wherein the control mechanism includes a lead screw and a nut to produce the relative movement between the stylet and the first portion of the wall, the at least a portion of the control mechanism including at least one of the lead screw and the nut.

37. A catheter assembly according to claim 35 further comprising a hub connecting a proximal end portion of the first catheter to a proximal end portion of the second catheter, the hub including the at least a portion of the control mechanism.

38. A catheter assembly according to claim 37 wherein the hub includes a first portion of a detent device, the first portion of the detent device being engageable with a second portion of the detent device to impede relative movement between the hub and the stylet.

39. A catheter assembly according to claim 33 further comprising a plurality of second catheters and a hub connecting a proximal end portion of the first catheter to a proximal end portion of each of the plurality of second catheters.

40. A catheter assembly according to claim 33 wherein the first lumen communicates with an opening formed in a distal end of the first catheter, the opening being closed with an occluding material that is less extensible than the relatively low durometer elastomeric material forming the first portion of the wall, the occluding material being shaped and dimensioned to receive an end of a stylet.

41. A catheter assembly according to claim 40 wherein the occluding material is formed as a plug and is adhesively bonded to the first portion of the wall.

42. A catheter assembly according to claim 40 wherein the wall of the first catheter also has an outer surface, the outer surface of the second portion of the wall including a trough to receive the second catheter.

43. A catheter assembly according to claim 33 wherein the wall of the first catheter also has an outer surface, the first lumen communicating with an opening formed in a distal end of the first catheter, the opening being closed with an occluding material that is less extensible than the relatively low durometer elastomeric material forming the first portion of the wall, the second catheter projecting out of the wall through the outer surface of the first catheter adjacent to the occluding material.

44. A catheter assembly according to claim 33 wherein the second catheter has a predetermined shape, the predetermined shape being provided by heat forming the second catheter before the second catheter is connected to the wall of the first catheter.

45. A catheter assembly according to claim 33 wherein the second catheter has a predetermined shape, the predetermined shape being provided by heat forming the second catheter after the second catheter is connected to the wall of the first catheter.

46. A catheter apparatus comprising:
a first catheter including a wall with an inner surface at least partially defining a lumen, a first portion of the wall of the first catheter being made of a relatively low durometer elastomeric material and being relatively extensible, a second portion of the wall being formed of a relatively high durometer elastomeric material and being relatively inextensible;
a second catheter connected to the wall of the first catheter and disposed outward of the inner surface of the wall, the second catheter being at least partially covered by a sheath portion of the first catheter; and
a control mechanism to engage a stylet when disposed in the lumen and to control relative movement between the stylet and the first portion of the wall and consequent extension of the first portion of the wall.

47. A catheter assembly according to claim 46 wherein the durometer of the relatively high durometer elastomeric material has a minimum ratio to the durometer of the relatively low durometer elastomeric material of about 1.5 to 1.

48. A catheter apparatus according to claim 46 further comprising a hub connected to a proximal end portion of the first catheter and to a proximal end portion of the second catheter, the control mechanism engaging the hub and being operable to produce controlled, relative movement between the hub and the stylet.

49. A catheter apparatus according to claim 48 wherein the control mechanism and the hub together include a lead screw and a nut to produce the relative movement between the stylet and the first portion of the wall, the control mechanism including one of the lead screw and the nut, the hub including the other of the lead screw and the nut.

50. A catheter apparatus according to claim 48 wherein the control mechanism includes a first portion of a detent device and the hub includes a second portion of the detent device, the first and second portions of the detent device being engageable with each other to impede relative movement between the hub and the stylet.

51. A catheter apparatus comprising:
a first catheter including a wall with an inner surface at least partially defining a lumen extending lengthwise of the first catheter, a first portion of the wall of the first catheter being made of a relatively low durometer elastomeric material and being relatively extensible, a second portion of the wall being formed of a relatively high durometer elastomeric material and being relatively inextensible;
a second catheter at least partially disposed in the wall of the first catheter outward of the inner surface of the wall and extending lengthwise of the first catheter; and
a control mechanism to engage a stylet when disposed in the lumen and to control relative movement between the stylet and the first portion of the wall and consequent extension of the first portion of the wall.

52. A catheter assembly according to claim 51 wherein the durometer of the relatively high durometer elastomeric material has a minimum ratio to the durometer of the relatively low durometer elastomeric material of about 1.5 to 1.

53. A catheter apparatus according to claim 51 further comprising a hub connected to a proximal end portion of the first catheter and to a proximal end portion of the second catheter, the control mechanism engaging the hub and being operable to produce controlled, relative movement between the hub and the stylet.

54. A catheter apparatus according to claim 53 wherein the control mechanism and the hub together include a lead screw and a nut to produce the relative movement between the stylet and the first portion of the wall, the control mechanism including one of the lead screw and the nut, the hub including the other of the lead screw and the nut.

55. A catheter apparatus according to claim 53 wherein the control mechanism includes a first portion of a detent device and the hub includes a second portion of the detent device, the first and second portions of the detent device being engageable with each other to impede relative movement between the hub and the stylet.

56. A catheter apparatus comprising:
a first catheter including a wall with an inner surface at least partially defining a first lumen, a first portion of the wall of the first catheter being made of a relatively low durometer elastomeric material and being relatively extensible, a second portion of the wall being formed of a relatively high durometer elastomeric material and being relatively inextensible;
a second catheter including a second lumen, the second lumen being disposed outside of the first lumen, the first lumen being disposed outside of the second lumen, the second catheter being connected to the first portion of the wall of the first catheter, extension of the first portion of the wall causing relative movement between the first portion of the wall and an adjacent, outwardly disposed portion of the second catheter; and
a control mechanism to engage a stylet when disposed in the first lumen and to control relative movement between the stylet and the first portion of the wall and consequent extension of the first portion of the wall.

57. A catheter assembly according to claim 56 wherein the durometer of the relatively high durometer elastomeric material has a minimum ratio to the durometer of the relatively low durometer elastomeric material of about 1.5 to 1.

58. A catheter apparatus according to claim 56 further comprising a hub connected to a proximal end portion of the first catheter and to a proximal end portion of the second catheter, the control mechanism engaging the hub and being operable to produce controlled, relative movement between the hub and the stylet.

59. A catheter apparatus according to claim 58 wherein the control mechanism and the hub together include a lead screw and a nut to produce the relative movement between the stylet and the first portion of the wall, the control mechanism including one of the lead screw and the nut, the hub including the other of the lead screw and the nut.

60. A catheter apparatus according to claim 58 wherein the control mechanism includes a first portion of a detent device and the hub includes a second portion of the detent device, the first and second portions of the detent device being engageable with each other to impede relative movement between the hub and the stylet.

61. A catheter assembly comprising:
a first catheter including a wall with an inner surface at least partially defining a lumen; and a second catheter connected to the wall of the first catheter and disposed outward of the inner surface of the wall, the second catheter being at least partially covered by a sheath portion of the first catheter, a first portion of the wall of the first catheter being made of a relatively low durometer elastomeric material and being relatively extensible, a second portion of the wall being formed of a relatively high durometer elastomeric material and being relatively inextensible, extension of the first portion of the wall causing relative movement between the first portion of the wall and an adjacent portion of the second catheter, the relatively low durometer elastomeric material having a Shore A hardness of from about 10 to about 50, the relatively high durometer elastomeric material having a Shore A hardness of from about 80 to about 90.

62. A catheter assembly according to claim 61 further comprising at least a portion of a control mechanism to grasp a stylet disposed in the lumen and to control relative movement between the stylet and the first portion of the wall and consequent extension of the first portion of the wall, the control mechanism including a rack and a pinion to produce the relative movement between the stylet and the first portion of the wall, the at least a portion of the control mechanism including at least one of the rack and the pinion.

63. A catheter assembly according to claim 61 further comprising a tether secured at one end to the first portion of the wall and secured at an opposite end to another portion of the catheter assembly.

64. A catheter assembly comprising:
a first catheter including a wall with an inner surface at least partially defining a lumen;
a plurality of second catheters connected to the wall of the first catheter and disposed outward of the inner surface of the wall, the second catheters being at least partially covered by a sheath portion of the first catheter; and
a hub connecting a proximal end portion of the first catheter to a proximal end portion of each of the plurality of second catheters,
a first portion of the wall of the first catheter being made of a relatively low durometer elastomeric material and being relatively extensible, a second portion of the wall being formed of a relatively high durometer elastomeric material and being relatively inextensible, extension of the first portion of the wall causing relative movement between the first portion of the wall and an adjacent portion of the second catheter,
the second catheters being disposed in a first array surrounding the first portion of the wall of the first catheter, proximal ends of the second catheters being disposed in a second array different from the first array on one side of the hub.

65. A catheter assembly comprising:
a first catheter including a wall with an inner surface at least partially defining a lumen; and
a second catheter connected to the wall of the first catheter and disposed outward of the inner surface of the wall, the second catheter being at least partially covered by a sheath portion of the first catheter,
a first portion of the wall of the first catheter being made of a relatively low durometer elastomeric material and being relatively extensible, a second portion of the wall being formed of a relatively high durometer elastomeric material and being relatively inextensible, extension of the first portion of the wall causing relative movement between the first portion of the wall and an adjacent portion of the second catheter,
the lumen communicating with an opening formed in a distal end of the first catheter, the opening being closed with an occluding material that is less extensible than the relatively low durometer elastomeric material forming the first portion of the wall of the first catheter, the occluding material being shaped and dimensioned to receive an end of a stylet and being a flowable and curable material that is cured in place in the opening.

66. A catheter assembly comprising:
a first catheter including a wall with an inner surface at least partially defining a lumen extending lengthwise of the first catheter; and
a second catheter at least partially disposed in the wall of the first catheter outward of the inner surface of the wall and extending lengthwise of the first catheter,
a first portion of the wall of the first catheter being made of a relatively low durometer elastomeric material and being relatively extensible, a second portion of the wall being formed of a relatively high durometer elastomeric material and being relatively inextensible, extension of the first portion of the wall causing relative movement between the first portion of the wall and an adjacent portion of the second catheter, the relatively low durometer elastomeric material having a Shore A hardness of from about 10 to about 50, the relatively high durometer elastomer having a Shore A hardness of from about 80 to about 90.

67. A catheter assembly according to claim 66 further comprising at least a portion of a control mechanism to grasp a stylet disposed in the lumen and to control relative movement between the stylet and the first portion of the wall and consequent extension of the first portion of the wall, the control mechanism including a rack and a pinion to produce the relative movement between the stylet and the first portion of the wall, the at least a portion of the control mechanism including at least one of the rack and the pinion.

68. A catheter assembly according to claim 66 further comprising a tether secured at one end to the first portion of the wall and secured at an opposite end to another portion of the catheter assembly.

69. A catheter assembly comprising:
a first catheter including a wall with an inner surface at least partially defining a lumen extending lengthwise of the first catheter;
a plurality of second catheters at least partially disposed in the wall of the first catheter outward of the inner surface of the wall and extending lengthwise of the first catheter; and
a hub connecting a proximal end portion of the first catheter to a proximal end portion of each of the plurality of second catheters,
a first portion of the wall of the first catheter being made of a relatively low durometer elastomeric material and being relatively extensible, a second portion of the wall being formed of a relatively high durometer elastomeric material and being relatively inextensible, extension of the first portion of the wall causing relative movement between the first portion of the wall and an adjacent portion of the second catheter,
the second catheters being disposed in a first array surrounding the first portion of the wall, proximal ends of the second catheters being disposed in a second array different from the first array on one side of the hub.

70. A catheter assembly comprising:
a first catheter including a wall with an inner surface at least partially defining a lumen extending lengthwise of the first catheter; and a second catheter at least partially disposed in the wall of the first catheter outward of the inner surface of the wall and extending lengthwise of the first catheter, a first portion of the wall of the first catheter being made of a relatively low durometer elastomeric material and being relatively extensible, a second portion of the wall being formed of a relatively high durometer elastomeric material and being relatively inextensible, extension of the first portion of the wall causing relative movement between the first portion of the wall and an adjacent portion of the second catheter, the lumen communicating with an opening formed in a distal end of the first catheter, the opening being closed with an occluding material that is less extensible than the relatively low durometer elastomeric material forming the first portion of the wall, the occluding material being shaped and dimensioned to receive an end of a stylet and being a flowable and curable material that is cured in place in the opening.

71. A catheter assembly comprising:

a first catheter including a wall with an inner surface at least partially defining a first lumen; and a second catheter including a second lumen, the second catheter being disposed outward of the inner surface of the wall, the first catheter being disposed outside of the second lumen, a first portion of the wall of the first catheter being made of a relatively low durometer elastomeric material and being relatively extensible, a second portion of the wall being formed of a relatively high durometer elastomeric material and being relatively inextensible, the second catheter being connected to the first portion of the wall of the first catheter, extension of the first portion of the wall causing relative movement between the first portion of the wall and an adjacent, outwardly disposed portion of the second catheter, the relatively low durometer elastomeric material having a Shore A hardness of from about 10 to about 50, the relatively high durometer elastomeric material having a Shore A hardness of from about 80 to about 90.

72. A catheter assembly according to claim 71 further comprising at least a portion of a control mechanism to grasp a stylet disposed in the first lumen and to control relative movement between the stylet and the first portion of the wall and consequent extension of the first portion of the wall, the control mechanism including a rack and a pinion to produce the relative movement between the stylet and the first portion of the wall, the at least a portion of the control mechanism including at least one of the rack and the pinion.

73. A catheter assembly according to claim 71 further comprising a tether secured at one end to the first portion of the wall and secured at an opposite end to another portion of the catheter assembly.

74. A catheter assembly comprising:

a first catheter including a wall with an inner surface at least partially defining a first lumen;

a plurality of second catheters, each second catheter including a second lumen, each second catheter also being disposed outward of the inner surface of the wall, the first catheter being disposed outside of the second lumen; and a hub connecting a proximal end portion of the first catheter to a proximal end portion of each of the plurality of second catheters a first portion of the wall of the first catheter being made of a relatively low durometer elastomeric material and being relatively extensible, a second portion of the wall being formed of a relatively high durometer elastomeric material and being relatively inextensible, the second catheters being connected to the first portion of the wall of the first catheter, extension of the first portion of the wall causing relative movement between the first portion of the wall and an adjacent, outwardly disposed portion of a second catheter, the second catheters being disposed in a first array surrounding the first portion of the wall, proximal ends of the second catheters being disposed in a second array different from the first array on one side of the hub.

75. A catheter assembly comprising:

a first catheter including a wall with an inner surface at least partially defining a first lumen; and a second catheter including a second lumen, the second catheter being disposed outward of the inner surface of the wall, the first catheter being disposed outside of the second lumen, a first portion of the wall of the first catheter being made of a relatively low durometer elastomeric material and being relatively extensible, a second portion of the wall being formed of a relatively high durometer elastomeric material and being relatively inextensible, the second catheter being connected to the first portion of the wall of the first catheter, extension of the first portion of the wall causing relative movement between the first portion of the wall and an adjacent, outwardly disposed portion of the second catheter, the first lumen communicating with an opening formed in a distal end of the first catheter, the opening being closed with an occluding material that is less extensible than the relatively low durometer elastomeric material forming the first portion of the wall, the occluding material being shaped and dimensioned to receive an end of a stylet and being a flowable and curable material that is cured in place in the opening.

76. A catheter apparatus comprising:

a first catheter including a wall with an inner surface at least partially defining a lumen, a first portion of the wall of the first catheter being made of a relatively low durometer elastomeric material and being relatively extensible, a second portion of the wall being formed of a relatively high durometer elastomeric material and being relatively inextensible;

a second catheter connected to the wall of the first catheter and disposed outward of the inner surface of the wall, the second catheter being at least partially covered by a sheath portion of the first catheter; and a control mechanism to engage a stylet when disposed in the lumen and to control relative movement between the stylet and the first portion of the wall and consequent extension of the first portion of the wall, the relatively low durometer elastomeric material having a Shore A hardness of from about 10 to about 50, the relatively high durometer elastomeric material having a Shore A hardness of from about 80 to about 90.

77. A catheter apparatus according to claim 76 further comprising a hub connected to a proximal end portion of the first catheter and to a proximal end portion of the second catheter, the control mechanism engaging the hub and being operable to produce controlled, relative movement between the hub and the stylet, the control mechanism and the hub together including a rack and a pinion gear to produce the relative movement between the stylet and the first portion of the wall, the control mechanism including one of the rack and the pinion gear, the hub including the other of the rack and the pinion gear.

78. A catheter apparatus comprising:
a first catheter including a wall with an inner surface at least partially defining a lumen extending lengthwise of the first catheter, a first portion of the wall of the first catheter being made of a relatively low durometer elastomeric material and being relatively extensible, a second portion of the wall being formed of a relatively high durometer elastomeric material and being relatively inextensible;
a second catheter at least partially disposed in the wall of the first catheter outward of the inner surface of the wall and extending lengthwise of the first catheter; and
a control mechanism to engage a stylet when disposed in the lumen and to control relative movement between the stylet and the first portion of the wall and consequent extension of the first portion of the wall,
the relatively low durometer elastomeric material having a Shore A hardness of from about 10 to about 50, the relatively high durometer elastomeric material having a Shore A hardness of from about 80 to about 90.

79. A catheter apparatus according to claim 78 further comprising a hub connected to a proximal end portion of the first catheter and to a proximal end portion of the second catheter, the control mechanism engaging the hub and being operable to produce controlled, relative movement between the hub and the stylet, the control mechanism and the hub together including a rack and a pinion gear to produce the relative movement between the stylet and the first portion of the wall, the control mechanism including one of the rack and the pinion gear, the hub including the other of the rack and the pinion gear.

80. A catheter apparatus comprising:
a first catheter including a wall with an inner surface at least partially defining a first lumen, a first portion of the wall of the first catheter being made of a relatively low durometer elastomeric material and being relatively extensible, a second portion of the wall being formed of a relatively high durometer elastomeric material and being relatively inextensible;
a second catheter including a second lumen, the second lumen being disposed outside of the first lumen, the first lumen being disposed outside of the second lumen, the second catheter being connected to the first portion of the wall of the first catheter, extension of the first portion of the wall causing relative movement between the first portion of the wall and an adjacent, outwardly disposed portion of the second catheter; and
a control mechanism to engage a stylet when disposed in the first lumen and to control relative movement between the stylet and the first portion of the wall and consequent extension of the first portion of the wall,
the relatively low durometer elastomeric material having a Shore A hardness of from about 10 to about 50, the relatively high durometer elastomeric material having a Shore A hardness of from about 80 to about 90.

81. A catheter apparatus according to claim 80 further comprising a hub connected to a proximal end portion of the first catheter and to a proximal end portion of the second catheter, the control mechanism engaging the hub and being operable to produce controlled, relative movement between the hub and the stylet, the control mechanism and the hub together including a rack and a pinion gear to produce the relative movement between the stylet and the first portion of the wall, the control mechanism including one of the rack and the pinion gear, the hub including the other of the rack and the pinion gear.

* * * * *